United States Patent
Okawa et al.

(10) Patent No.: US 8,371,848 B2
(45) Date of Patent: Feb. 12, 2013

(54) DENTAL DIAGNOSTIC AND TREATMENT APPARATUS

(75) Inventors: Shinichi Okawa, Kyoto (JP); Kenji Kino, Kyoto (JP); Kazunari Matoba, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 1982 days.

(21) Appl. No.: 10/582,302

(22) PCT Filed: Dec. 8, 2004

(86) PCT No.: PCT/JP2004/018672
§ 371 (c)(1),
(2), (4) Date: Jun. 8, 2006

(87) PCT Pub. No.: WO2005/053562
PCT Pub. Date: Jun. 16, 2005

(65) Prior Publication Data
US 2007/0121786 A1 May 31, 2007

(30) Foreign Application Priority Data

Dec. 8, 2003 (JP) .................................. 2003-409197
Apr. 30, 2004 (JP) .................................. 2004-135338

(51) Int. Cl.
*A61C 1/00* (2006.01)
(52) U.S. Cl. ......................................................... 433/29
(58) Field of Classification Search ................... 433/29, 433/86, 119, 215, 216, 32; 600/410, 411, 600/476, 477, 589, 590
See application file for complete search history.

(56) References Cited

U.S. PATENT DOCUMENTS 4,479,499 A * 10/1984 Alfano .......................... 600/477
5,306,144 A   4/1994 Hibst et al.
(Continued)

FOREIGN PATENT DOCUMENTS

JP    S46-35916 B     10/1971
JP    5-337142        12/1993
(Continued)

OTHER PUBLICATIONS

Patent Abstracts of Japan, Publication No. 07-275261; Date of Publication: Oct. 24, 1995; in the name of Minoru Imazato.
(Continued)

*Primary Examiner* — Sunil K Singh
(74) *Attorney, Agent, or Firm* — Christie, Parker & Hale, LLP

(57) ABSTRACT

A diagnostic/treatment instrument such as a handpiece equipped with a dental treatment tool, etc. is provided with a light radiating unit that can distinctively detect a dental lesion, to facilitate the treatment of the lesion. A light source for emitting light that can distinctively detect the lesion is mounted near the head of the handpiece to which a diagnostic/treatment tool can be attached. The light emitted from the light source illuminates an area forward of the diagnostic/treatment tool. Alternatively, the light source comprises a plurality of light-emitting devices which are arranged around the periphery of the forward end of the handpiece head in such a manner as to encircle the diagnostic/treatment tool, and radiates light to illuminate the area forward of the diagnostic/treatment tool. When an oral cavity is illuminated with the light, a clinician can observe reflected fluorescent light by using a filtering function that passes the fluorescent light, and thus the clinician can perform the treatment while checking the lesion.

37 Claims, 52 Drawing Sheets

U.S. PATENT DOCUMENTS

| | | |
|---|---|---|
| 6,186,780 B1 | 2/2001 | Hibst et al. |
| 6,607,384 B1 * | 8/2003 | Nakanishi .................. 433/29 |
| 2001/0023057 A1 | 9/2001 | Alexander |
| 2002/0151941 A1 | 10/2002 | Okawa et al. |
| 2003/0156788 A1 | 8/2003 | Henning |
| 2005/0003323 A1 * | 1/2005 | Katsuda et al. ............ 433/29 |

FOREIGN PATENT DOCUMENTS

| | | |
|---|---|---|
| JP | 7-275261 | 10/1995 |
| JP | 9-189659 | 7/1997 |
| JP | 2000-24013 | 1/2000 |
| JP | 2000-316874 | 11/2000 |
| JP | 2001-112779 | 4/2001 |
| JP | 2001-299699 | 10/2001 |
| JP | 2002-306512 | 10/2002 |
| JP | 2004-089239 | 3/2004 |
| WO | WO 02/080803 A1 | 10/2002 |

OTHER PUBLICATIONS

Patent Abstracts of Japan, Publication No. 09-189659; Date of Publication: Jul. 22, 1997; in the name of Dr. Raimund Hibst et al.

International Search Report, dated Mar. 15, 2005, corresponding to PCT/JP2004/018672.

International Preliminary Examination Report, dated Feb. 9, 2006, corresponding to PCT/JP2004/018672.

Patent Abstract of Japan, Publication No. 05337142 A, Published on Dec. 21, 1993, in the name of Hibst, et al.

Patent Abstract of Japan, Publication No. 2000024013 A, Published on Jan. 25, 2000, in the name of Hibst, et al.

Patent Abstract of Japan, Publication No. 2000316874 A, Published on Nov. 21, 2000, in the name of Yamashita, et al.

Patent Abstract of Japan, Publication No. 2001112779 A, Published on Apr. 24, 2001, in the name of Nakanishi.

Patent Abstract of Japan, Publication No. 2002306512 A, Published on Oct. 22, 2002, in the name of Okawa, et al.

Japanese Office action dated Aug. 4, 2009, for priority Japanese application 2004-135338, with English translation, noting Japanese references previously filed in an IDS dated Jun. 8, 2006.

Japanese Office action dated Aug. 4, 2009, for corresponding Japanese application 2004-354675, with English translation, noting references listed in this IDS, as well as Japanese references previously filed in an IDS dated Jun. 8, 2006.

Alfano, R, et al., *Human Teeth With and Without Caries Studied by Laser Scattering, Fluorescence, and Absorption Spectroscopy*, IEEE Journal of Quantum Electronics, vol. QE-20, No. 12, Dec. 1984, pp. 1512-1516.

Supplemental European Search Report for European Patent Application No. 04807031.2, dated Sep. 14, 2010, 5pp.

Office action for corresponding Japanese Patent Application No. 2004-354675, dated Nov. 30, 2010, 3pp.

Office action for corresponding Japanese Patent Application No. 2004-135338, dated Nov. 30, 2010, 4pp.

* cited by examiner

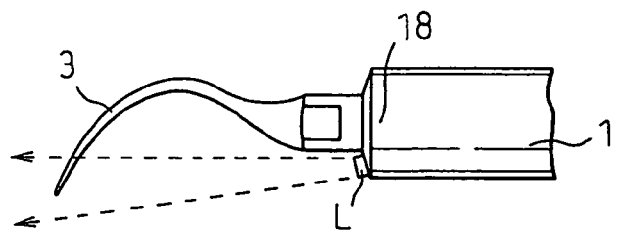
Fig.17A
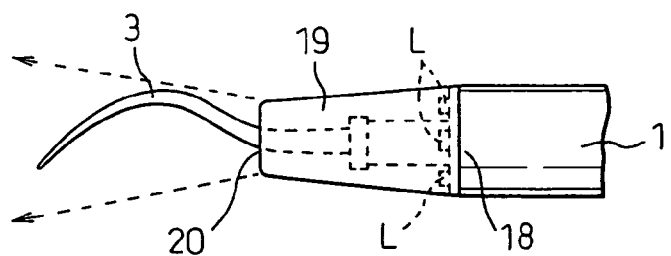
Fig.17B
Fig.18A
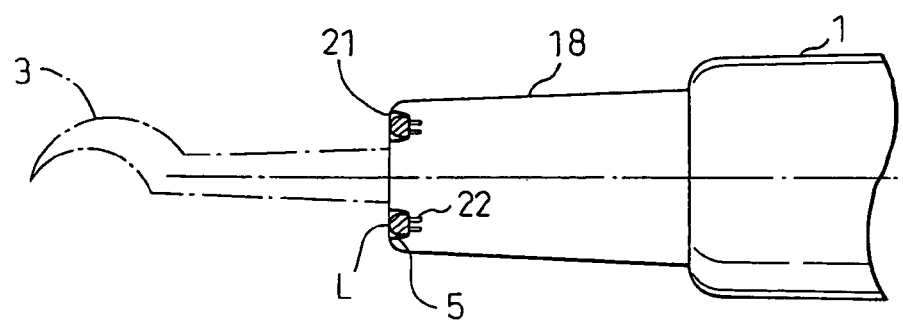
Fig.18B
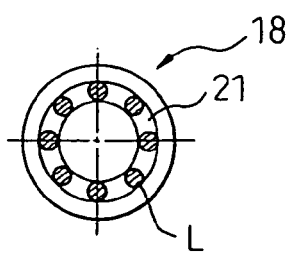

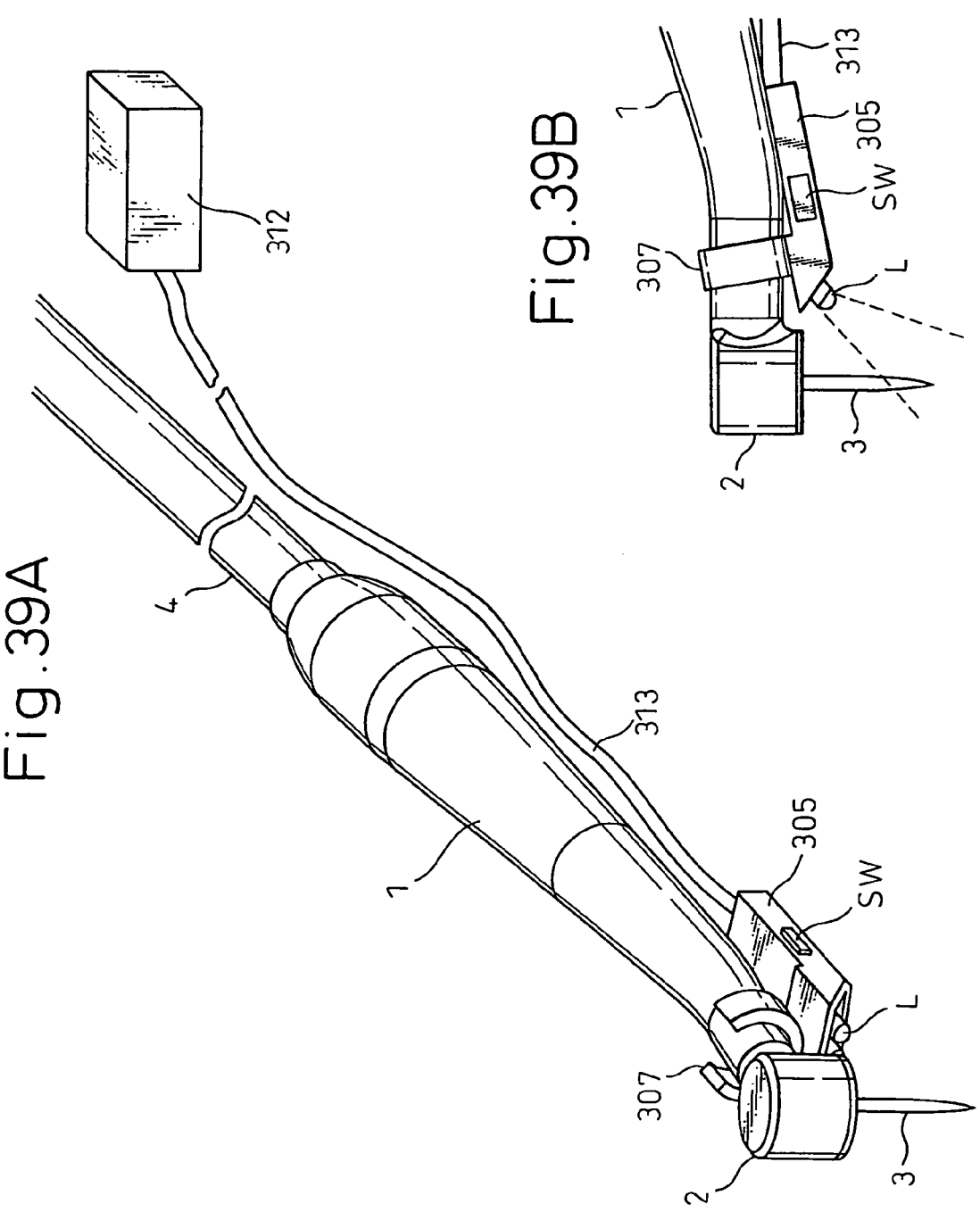

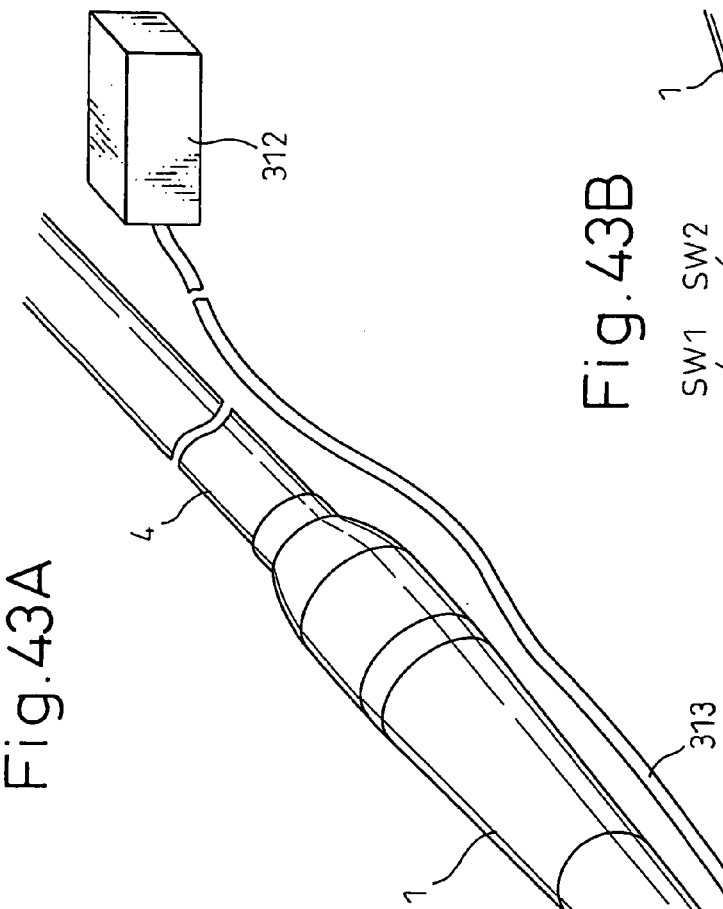
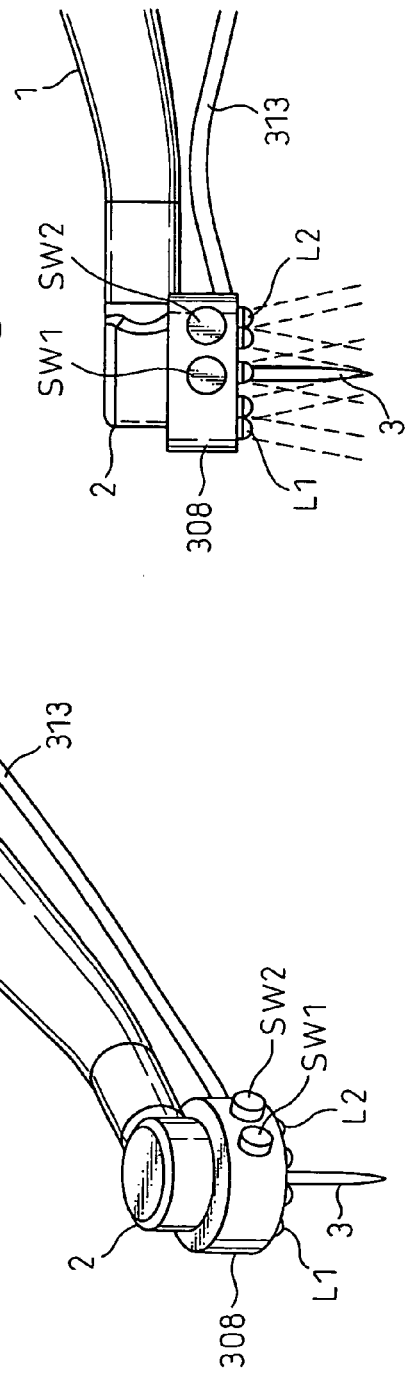
Fig.43A
Fig.43B

DENTAL DIAGNOSTIC AND TREATMENT APPARATUS

CROSS-REFERENCE TO RELATED APPLICATION

This application is a National Phase Patent Application of International Application Number PCT/JP2004/018672, filed on Dec. 8, 2004, which claims priority of Japanese Patent Application Number 2003-409197, filed on Dec. 8, 2003, and Japanese Patent Application Number 2004-135338, filed on Apr. 30, 2004.

TECHNICAL FIELD

The present invention relates to a dental diagnostic and treatment apparatus, and more particularly to a dental diagnostic and treatment apparatus in which a dental diagnostic/treatment instrument such as a handpiece equipped with a treatment tool such as a tool used for the treatment of teeth is provided with a light radiating means having a light source capable of emitting light with which a dental lesion can be distinctively detected, thereby facilitating the treatment of the lesion.

BACKGROUND ART

In dental diagnosis and treatment, dentists make full use of various handpieces (or instruments), such as a dental air turbine handpiece, a dental micromotor handpiece, a dental scaler handpiece, a dental three-way syringe, a dental mirror, a vacuum syringe, a dental photo-polymerization device, a laser handpiece, and a dental tooth cleaning device, equipped with such tools as a dental drilling tool, a dental plaque/tartar removing tool, a treatment area rinsing tool, a drilling debris/saliva evacuation tool, etc. When performing intraoral diagnosis or treatment by using such handpieces, a shadow-free light separately mounted on a dental unit or the like is turned on, and the diagnosis or treatment is performed on the patient while illuminating the patient's oral cavity with the light.

However, depending on the orientation of the patient and the area to be treated or on the direction from which the clinician such as the dentist works, the oral cavity may not be illuminated sufficiently, making it difficult to observe the treatment area; every time this happens, the position of the shadow-free light has to be adjusted, and the efficiency of the treatment work thus suffers.

In view of this, in recent years, a dental handpiece has been developed and commercially implemented that has a light source such as a halogen lamp and a light guide built into the handpiece body and that is designed to illuminate the treatment area such as a tooth by radiating light produced by the light source from the forward end of the handpiece (refer, for example, to Patent Document 1).

This handpiece is a scaler having a tip at the forward end of the handpiece body; in this example, since the shape and length of the tip differ according to the scaler used, and the position of the tip end is therefore not constant, the light exit end of the light guide is arranged in a ring shape on the forward end of the handpiece body so that the emitted light is not concentrated in one particular direction but spreads out with a certain angle. This requires the light guide to be formed in a special shape, resulting in a significant increase in cost. Furthermore, the structure for accommodating the light guide of such shape within the handpiece body becomes complex, and the manufacturing cost increases. There has also been the problem that the mechanism for holding the light exit end portion of the light guide interferes with the fundamental vibration of the scaler, causing an adverse effect on the vibration characteristics of the product.

In view of the above, there is proposed a handpiece in which one or more light-emitting devices are arranged on the forward end of the handpiece body so that the light for illuminating the treatment target area is radiated directly from the light-emitting devices without using a light guide (refer, for example, to Patent Document 2).

Here, light-emitting diodes (LEDs) that emit white light or semiconductor devices that emit laser light are used as the light-emitting devices to be mounted on the handpiece, and the plurality of light-emitting devices are arranged in a ring on the forward end of the handpiece body in such a manner as to encircle the axes of the tool attached thereto, or the plurality of light-emitting devices are combined into a single light-emitting device unit; further, these light-emitting devices are detachably mounted on the handpiece body.

According to the proposed handpiece design, since the light-emitting devices are used as described above, there is no need to use a light guide, avoiding problems associated with the use of the light guide, such as increased cost, increased complexity of structure, and attenuation of light, while also eliminating the need for cooling the light source; as a result, a dental instrument having desired performance can be achieved at a relatively low cost.

In the above-described dental handpieces, the light from the light source is radiated to illuminate the treatment target area in order to facilitate the observation of that area. On the other hand, it is normal practice to radiate light of a particular wavelength to the treatment target area in order to distinguish whether it is dental caries, plaque, tartar, or the like (Refer, for example, to Patent Documents 3 and 4).

The apparatus disclosed in the above-cited Patent Documents is a recognition apparatus for recognizing the condition of a tooth to detect caries, plaque, infection of the tooth by bacteria, etc. with high accuracy and high reliability. The recognition apparatus comprises a light source for generating excitation radiation which is directed to the tooth to be examined and excites fluorescent radiation at that tooth, a detection device for detecting the fluorescent radiation from that tooth, and a spectral filter which is mounted at the front of the detection device, and the wavelength of the excitation radiation to be emitted from the light source is set within a range of 600 nm to 670 nm. With this arrangement, when an increase in the intensity difference between the fluorescence spectrum of the caries region and the fluorescence spectrum of a healthy tooth portion is detected, it is recognized that dental caries is present in the tooth illuminated with the radiation.

On the other hand, various illumination devices have been developed in recent years, aiming to prevent the efficiency of diagnosis or treatment work from dropping due to insufficient intraoral illumination. Many of such illumination devices are designed to be able to illuminate the oral cavity during diagnosis or treatment with a light source mounted on the forward end of the handpiece.

For example, in a contra-angle dental/medical handpiece, a plurality of light-emitting diodes (LEDs) are arranged to encircle a tool mounted in a tool mounting portion so that the area being diagnosed or treated is brightly illuminated over a wide range of 360 degrees around the tool (refer, for example to Patent Document 5). In this handpiece, the power for lighting the plurality of LEDs is supplied via flexible lead wires or a flexible wiring substrate disposed within the handpiece body. However, with the technique disclosed in Patent Document 5, intraoral lesions cannot be detected, because the wavelength of the light emitted from the LEDs is not for detecting lesions; instead, the LEDs are used for simply illuminating the oral cavity.

On the other hand, it is known to provide a dental handpiece which has a built-in light source that emits excitation light capable of detecting lesions; in this handpiece, a laser diode and a light guide are mounted within the handpiece such as a dental scaler, and the oral cavity is illuminated with the light radiated from the forward end of the handpiece and the resulting emission of fluorescence is detected by a photodiode for evaluation (refer, for example, to Patent Document 6). It is claimed that, using this handpiece, the treatment for dental caries, plaque, bacteria infection, calculus, tartar, etc. can be easily performed while detecting such lesions and evaluating them.

With this handpiece, diagnosis or treatment can be done while detecting and evaluating the condition of an intraoral lesion, but it has only been possible to detect and evaluate the presence of caries in the spot area illuminated with the excitation light from the laser diode, and it has not been possible to identify the extent of the caries. Furthermore, the handpiece is not of the type that can be attached to existing dental instruments that dentists use for treatment.

There has also been developed a handpiece of the type in which a light guide and a light source are mounted within the handpiece body so that illumination light for illuminating the oral cavity can be radiated from the forward end of the handpiece, but this type of handpiece is designed to radiate illumination light, not excitation light. Further, in the handpiece proposed in the previously mentioned Patent Document 2, one or more light-emitting devices are arranged on the forward end of the handpiece body so that the light for illuminating the target area to be diagnosed or treated is radiated directly from the light-emitting devices without using a light guide.

LEDs that emit white light or semiconductor laser devices (LDs) that emit laser light are used as the light-emitting devices to be mounted in the above handpiece; on the other hand, there has been developed a dental handpiece that is designed so that a light-emitting device module constructed by integrating a plurality of bare chips each forming an LED can be incorporated as an illumination device for illuminating the intraoral area to be diagnosed or treated (refer, for example, to Patent Document 7). This light-emitting module is provided with electrode pins and, by connecting the electrode pins to a socket provided in the forward end of the handpiece, power for driving the LEDs is supplied via a power cord connected to the rear end of the handpiece.

However, in Patent Documents 2 and 7 also, the light emitted from the light source is illumination light, not excitation light for detecting a lesion, and furthermore, the handpiece is not of the type that can be attached to existing dental instruments that dentists use for treatment. On the other hand, in recent years, the power of LEDs and semiconductor lasers has increased, and it has become possible to observe lesions with the naked eye.

Patent Document 1: Japanese Unexamined Patent Document No. H07-275261

Patent Document 2: Japanese Unexamined Patent Document No. 2000-316874

Patent Document 3: Japanese Unexamined Patent Document No. H05-337142

Patent Document 4: Japanese Unexamined Patent Document No. H09-189659

Patent Document 5: Japanese Unexamined Patent Document No. 2001-112779

Patent Document 6: Japanese Unexamined Patent Document No. 2001-299699

Patent Document 7: Japanese Unexamined Patent Document No. 2002-306512

DISCLOSURE OF THE INVENTION

Problems to be Solved by the Invention

However, in any of the above-proposed dental handpieces, general-purpose LED devices are directly used for dental applications. Since the dental handpiece needs to provide a sufficient amount of illumination for intraoral diagnosis or treatment, it becomes necessary to use an LED having large output power and hence a large size, or to increase the number of LEDs. In either case, the dental handpiece increases in size, which is impractical.

Usually, caries detection is done with the naked eye, but on the other hand, in the previously described recognition apparatus for recognizing the condition of a tooth, excitation light for exciting fluorescent radiation is radiated onto the target area to detect, for example, the presence or absence of caries in that area. Accordingly, when treating caries, first the teeth in the mouse are illuminated and observed using a detection probe and, when a tooth that appears affected by caries is found, then the recognition apparatus is used to determine whether the tooth is a carious tooth. If it is determined that the tooth is a carious tooth, the tooth is treated using a handpiece mounted, for example, with a drilling tool.

In this way, for the treatment of caries, for example, several kinds of handpieces designed for different purposes are used, and the treatment is performed while confirming the position of the caries, making the treatment work complex. As a result, it has been difficult to accurately locate the position of the caries during the treatment, and furthermore, it has been difficult to confirm how far the caries has been treated. In particular, the drawback has been that it is difficult to confirm whether the caries has been completely removed or not after each drilling operation. Furthermore, the prior art techniques have lacked the technical concept of capturing an image of a lesion when performing treatment using a treatment instrument in combination with the handpiece.

Usually, when treating a carious tooth, the dentist detects the carious lesion with the naked eye by illuminating the patient's oral cavity with a shadow-free lamp or a handpiece equipped with an illumination function. With this caries detection method relying on the naked eye, advanced caries visible to the eye can be detected, but caries not so advanced as to be visible to the naked eye cannot be detected. When using an excitation light radiating handpiece which emits excitation light for exciting fluorescence to detect a lesion, the presence or absence of caries is detected by checking the fluorescence of the tooth illuminated with the light. The carious tooth can thus be identified. However, the fluorescence is weak light, and when viewing only the fluorescence, normal tissue appears so dark that only its contour can be seen.

In this way, for the treatment of caries, for example, several kinds of handpieces designed for different purposes are used, and the treatment is performed while confirming the position of the caries, making the treatment work complex. As a result, it has been difficult to accurately locate the position of the caries during the diagnosis or treatment, and furthermore, it has been difficult to confirm how far the caries has been treated. In particular, it has been difficult to confirm whether the caries has been completely removed or not after each drilling operation.

Accordingly, it will be convenient if not only diagnostic or treatment tools but also excitation light emitting light sources or the like can be detachably mounted on various kinds of existing handpieces so that all of the various kinds of handpieces designed for different purposes can be used as handpieces capable of detecting lesions such as dental caries. Furthermore, if the handpiece is equipped with a function that can radiate illumination light for illuminating the oral cavity as well as the excitation light for detecting lesions such as dental caries, then not only lesions such as dental caries but also normal tissue around them can be made clearly visible; as a result, the usefulness of the handpiece is enhanced, and the diagnosis or treatment can be performed reliably and efficiently.

With the dental handpieces disclosed in the above-cited Patent Documents 2 and 5, the area around the tool mounted in the tool mounting portion can be illuminated; for example, even when a tooth is being drilled by the tool, the tooth can be brightly illuminated. However, even if the tooth can be illuminated during the drilling operation, it is difficult to check the extent of the dental caries not easily visible to the naked eye, especially, incipient caries, etc. Furthermore, it is not easy to detect tartar or plaque.

On the other hand, with the dental handpiece disclosed in the above-cited Patent Document 6, in which the laser diode or photodiode and the light guide are built into the handpiece body, it is possible to detect the intensity of fluorescence at the point illuminated with the excitation light, that is, the intensity of the fluorescence occurring due to the illumination of the light emitted from the forward end of the handpiece, and the treatment can be started after determining how far the lesion extends by taking measurements at several points. However, it has not been possible to observe the extent of the lesion at a glance. Furthermore, it has not been possible to illuminate the oral cavity at the same time.

Further, in the dental handpiece disclosed in the above-cited Patent Document 7 and to which tools can be attached, the light-emitting device module is built into the handpiece body, and also, the light it can emit is limited to white light and blue light, that is, the light source is not of the type that emits light of a specific wavelength that can detect dental caries or tartar.

In this way, in the case of the previously developed handpieces, the intraoral diagnostic or treatment function, the intraoral illumination function, and the intraoral lesion detection function have been incorporated in separate handpieces, and handpieces equipped with all of these functions have not been available. Accordingly, clinicians have had to prepare various handpieces having various functions and choose an appropriate one for each purpose during diagnosis or treatment, which is troublesome. If these functions are to be incorporated into a single handpiece, the handpiece must be newly developed, which would lead to the problem that the price of the handpiece would increase.

Accordingly, it is an object of the present invention to provide a dental diagnostic and treatment apparatus equipped with a light-emitting device that can achieve small size and high output and that emits light of wavelength capable of distinctively detecting intraoral lesions such as dental caries and tartar. When an intraoral lesion such as dental caries or tartar is illuminated with the excitation light emitted from the light-emitting device, the lesion emits fluorescence, and the clinician performs diagnosis or treatment while observing the fluorescence. In particular, since infrared radiation has excellent straightness, the lesion near the surface of a tooth can be clearly identified by observing the radiation through a filter.

It is another object of the present invention to provide a dental diagnostic and treatment apparatus equipped with an intraoral illumination device, wherein provisions are made so that an adapter capable of radiating excitation light or illumination light emitted from a light source onto an intraoral lesion can be detachably mounted on a handpiece used to diagnose or treat the lesion, thereby enabling an additional function to be easily incorporated into the existing handpiece.

Means for Solving the Problems

To solve the above problems, the present invention provides a dental diagnostic and treatment apparatus comprising: an instrument having a forward end equipped with or capable of being equipped with a diagnostic/treatment tool for diagnosing or treating a lesion in an oral cavity; and light radiating unit having a light source disposed at or near the forward end, wherein excitation light for exciting light for distinctively detecting the lesion is radiated from the light source toward the lesion.

The wavelength of the excitation light is selected from within a near ultraviolet region of 405±50 nm, a blue region of 470±30 nm, a red region of 700±100 nm, an infrared region, or a near infrared region.

The light radiating unit includes a light source for emitting the excitation light and a light source for emitting illumination light into the oral cavity, and is capable of simultaneously radiating the excitation light and the illumination light; alternatively, the light radiating unit is capable of selectively or simultaneously radiating the excitation light and the illumination light. Further, white light is radiated as the illumination light.

The light source includes a light-emitting device constructed from an LED or a semiconductor laser diode, and the light source further includes a light-emitting device for emitting the white light.

The light radiating unit includes a light source for emitting the excitation light and a light source for emitting illumination light into the oral cavity, and is capable of simultaneously radiating the excitation light and the illumination light; further, the light radiating means variably adjusts the light emission level of the light source.

The light radiating unit includes a plurality of light sources for emitting light in different wavelength regions, and is capable of radiating light in one wavelength region by switching between the plurality of light sources or is capable of variably adjusting the light emission level of at least one of the light sources.

The light radiating unit includes an excitation light source for emitting the excitation light and a white light source for emitting white light, and is capable of radiating either the excitation light or the white light by switching between the excitation light source and the white light source or variably adjusts the light emission level of at least one of the light sources.

The light radiating unit includes a plurality of light sources for emitting excitation light in different wavelength regions, and is capable of radiating excitation light in one wavelength region by switching between the plurality of light sources or variably adjusts the excitation light emission level of at least one of the light sources.

The light radiating unit includes excitation light sources for emitting excitation light in different wavelength regions and a white light source for emitting white light, and is capable of radiating the excitation light and the white light by switching between the plurality of excitation light sources and the white light source or variably adjusts the light emission level of at least one light source selected from among the plurality of excitation light sources and the white light source.

The light source includes a light-emitting device selected from among a halogen lamp, a xenon lamp, a sodium lamp, a metal halide lamp, a mercury lamp, and a blacklight lamp; further, the light radiating means includes an optical filter for selecting light of a designated wavelength from the light emitted from the light source, and the light of the designated wavelength is selected by replacing another filter with the filter having a different characteristic.

The light radiating unit includes a plurality of light sources for emitting light at different wavelengths, and selects the light to be emitted by sequentially switching between the plurality of light sources, thereby sequentially radiating the light at the different wavelengths in a time-division fashion.

The radiating part is disposed in the diagnostic/treatment tool or near the mounting portion of the diagnostic/treatment tool, and the excitation light is radiated from an area surrounding the diagnostic/treatment tool toward the lesion.

The light source is mounted on a detachable member formed so as to be detachable from the forward end, and the detachable member includes a connecting member which is capable of detachably engaging with the forward end and which, when placed into engagement with the forward end, supplies power to the light source.

The diagnostic/treatment tool which radiates treatment laser light is attached to the forward end, and the light source of the light radiating means is disposed on the forward end; further, the light radiating unit radiates the excitation light and the treatment laser light onto the lesion in a time-division fashion.

The radiating part is provided in an adapter having a mounting member capable of being detachably mounted on the forward end of the instrument, and the light source includes a plurality of light-emitting devices, wherein the plurality of light-emitting devices are arranged side by side in an end face portion of the adapter.

The adapter has a ring-shaped structure which is detachably fitted onto the forward end of the instrument, and the adapter is equipped with an operating part for operating the light source and further equipped with a power supply for driving the light source, wherein the power supply is a primary cell or a secondary cell.

The power supply for driving the light source is provided separately from the adapter, and the power supply is detachably mounted on the body of the instrument.

The operating part for operating the light source is detachably mounted on the body of the instrument, and the mounting member elastically holds the adapter on the forward end of the instrument.

The adapter is equipped with a filter plate having a plane surface perpendicular to the axis direction of the body of the instrument, the plane surface spreading so as to encircle the body.

When the instrument is equipped with an illuminating unit for illuminating the oral cavity, the adapter is mounted at a position that interrupts the illumination light emitted from the illuminating unit.

The instrument is a laser handpiece capable of radiating treatment laser light into the oral cavity together with guide light that serves as a guide in locating an area being illuminated with the treatment laser light, wherein the excitation light is contained in the guide light.

The radiating part includes the light-emitting device mounted near the mounting portion of the diagnostic/treatment tool, wherein the light-emitting device is mounted in such a manner as to encircle the diagnostic/treatment tool; further, the light-emitting device is accommodated in a position near the mounting portion of the diagnostic/treatment tool.

The light radiating unit includes a plurality of light sources for emitting light at different wavelengths, and an operating part capable of switching selection between the plurality of light sources or capable of variably adjusting the light emission level of at least one of the light sources is mounted on the instrument.

Effect of the Invention

According to the present invention described above, since the light radiating unit including the light source for radiating the light for distinctively detecting a lesion onto the target area is provided near the diagnostic/treatment tool of the dental diagnostic and treatment apparatus, the clinician who is performing diagnosis or treatment using this dental diagnostic and treatment apparatus can clearly observe intraoral lesions such as caries, sclerotic dentin, tartar, plaque, biofilm, teeth chipping, cracking, etc. by visual examination using a filter or the like for detecting the reflected light or the fluorescence occurring due to excitation by the radiated light, and can thus confirm the extent and degree of the treatment while performing the diagnosis or treatment.

Further, by also installing a plurality of light emitting devices of different wavelengths or an illumination light source such as a white light source, it becomes possible to detect different kinds of lesions by switching the lesion detection function manually or in a time division fashion, or to illuminate lesions for visual examination. Since the clinician does not need to change the handpiece according to the kind of the lesion or the purpose of the diagnosis or treatment, the work efficiency increases.

Furthermore, since the light radiating unit for illuminating the target area can also be mounted near the diagnostic/treatment tool of the dental diagnostic and treatment apparatus, the clinician can perform the diagnosis or treatment by switching between the illumination device and the diagnostic/treatment device, and the work efficiency thus increases.

As described above, according to the present invention, when the intraoral illumination device of the invention is mounted on an existing handpiece having an illumination function, the function that can detect an intraoral lesion can be easily implemented on the handpiece in addition to the intraoral illumination function; on the other hand, when the intraoral illumination device of the invention is mounted on a dental handpiece that does not have an illumination function, the handpiece can be easily converted into a handpiece having a function that can detect an intraoral lesion and, when the ordinary illumination function is added to it, not only the intraoral lesion but also the living tissue around the lesion becomes easier to observe than when using a shadow-free lamp attached to a dental unit, and the treatment work is thus facilitated.

As described above, when the intraoral illumination device of the invention is mounted on various dental handpieces that do not have a function for radiating excitation light for detecting a lesion, and the excitation light is radiated, the diagnosis or treatment can be performed based on the extent of the lesion while observing the fluorescence excited at the lesion inside the oral cavity; accordingly, the lesion as the area to be treated can be clearly recognized in the form of surface image information, and only the lesion can be selectively treated.

Furthermore, by virtue of the function whereby the illumination light for illuminating the oral cavity and the excitation light capable of detecting a lesion such as caries can be simultaneously radiated, not only the lesion such as caries but also the normal living tissue around the lesion can be clearly recognized; as a result, the usefulness of the handpiece increases, and the diagnosis or treatment can be performed reliably and efficiently.

Since the intraoral illumination device according to the invention can radiate one or more kinds of light, selected from among white light, monochromatic light, infrared light, and ultraviolet light, as the light of the wavelength for detecting and/or illuminating the lesion, illumination light and optimum excitation light capable of detecting various lesions can be used in combination. Furthermore, since the intensity of the light to be emitted from the light source can be adjusted, the excitation light and the illumination light can be adjusted to light output levels that facilitate visual recognition of the lesion.

According to the present invention, since the light source is constructed from a light-emitting diode or a semiconductor laser light-emitting device, the size of the product can be easily reduced and, because they are available on the market, the cost of the product can also be reduced. Further, the light source includes one kind of lamp selected from among a halogen lamp, a xenon lamp, a sodium lamp, a metal halide lamp, and a mercury lamp; since such lamps emit light over a wide wavelength range, the light can also be used as the illumination light. Here, if an optical filter is provided to select, from the wide wavelength range of the lamp light, a specific wavelength for detecting a lesion so that the light of the selected wavelength is projected, excitation lights of various wavelengths can be generated. If such a filter is made detachable, the light of the lamp light source can be used not only as the illumination light but also as the excitation light.

Since the wavelength for detecting the lesion is selected from within the near ultraviolet region of 405±50 nm, the blue region of 470±30 nm, the red region of 700±100 nm, the infrared region, or the near infrared region, the presence or absence of tartar, caries, filler, fine cracks, etc. can be identified. Further, the light emitted from the light source contains light of a wavelength suitable for curing a photo-polymerizable resin, a carious or cracked portion can be immediately treated by filling it with a photo-polymerizable resin.

According to the present invention, the light source can emit light at a plurality of wavelengths, and the light to be emitted from the light source can be switched from one wavelength to another; for example, known wavelength-switchable light-emitting diodes or semiconductor lasers can be used, and the plurality of excitation lights can be selected for use.

Since the intraoral illumination device of the present invention is equipped with a light-emitting device that can emit a plurality of wavelengths and that can be switched to a selected one of the wavelengths, the illumination function and the lesion detection function, for example, can be added to an existing handpiece, and the lesion detection function can be switched between the plurality of wavelengths. Accordingly, in the treatment of dental caries, the caries should be removed by making full use of the illumination function and the lesion detection function, until the fluorescence being emitted from the caries becomes no longer visible; this provides a guide as to the removal of the lesion. Further, by radiating excitation light of an optimum wavelength for each different lesion such as caries, tartar, etc., the visibility of the lesion can be enhanced.

Furthermore, according to the present invention, when the light source includes one of the above-mentioned lamps, lights of different wavelengths can be selected from the light emitted from the lamp by changing the optical filters; that is, by changing the optical filters, both the illumination function and the lesion detection function can be provided, and further, the lesion detection function optimized for each different lesion can be achieved.

According to the present invention, the light source includes a plurality of light-emitting devices, and the plurality of light-emitting devices are arranged side by side at one end of the adapter, achieving efficient radiation. The adapter has a ring-shaped structure which is detachably fitted onto the forward end of the dental instrument, and the light can therefore be radiated from any angle, so that the dental instrument can be used without forming shadows around it. Likewise, since the plurality of light-emitting devices forming the light source are mounted in a ring at one end of the adapter, the dental instrument can be used without forming shadows around it.

Further, according to the present invention, since the operating part for operating the light source is provided on the adapter, the operation such as the on-off operation of the light source can be performed by just operating the switch, etc. mounted on the adapter. Furthermore, since the power supply is provided in the adapter, the overall size of the device can be reduced by using a small-sized cell such as a button cell as the power supply. The power supply comprises a primary cell or a secondary cell which is easily detachable and replaceable.

According to the present invention, the light source is driven by a power supply provided separately from the adapter; here, since the relatively heavy and large power supply can be placed at a location remote from the light source, the presence of the power supply does not interfere with the operation of the instrument.

As described above, according to the intraoral illumination device of the present invention, since the power supply is built into or connected to the adapter, the light-emitting devices provided on the adapter can be driven for operation even if the existing instrument is not equipped with a power supply, and the illumination function or the lesion detection function can thus be accomplished. On the other hand, when the construction is such that power is supplied to the existing instrument, a connection structure for supplying power to the intraoral illumination device need not be specifically provided, avoiding an increase in cost.

According to the present invention, since the power supply is detachably mounted on the body of the dental instrument, the power supply can be held firmly and can be replaced easily, compared with the case where it is not mounted on the body. Furthermore, the operating part for operating the light source is detachably mounted on the body of the dental instrument, enhancing the operability of the instrument.

Further, according to the present invention, the mounting member is constructed to elastically hold the adapter on the body of the dental instrument so that the adapter can be easily attached and detached with respect to the body. In the intraoral illumination device of the present invention, since the mounting member for mounting on the handpiece is constructed from an elastically holding member such as a coil, not from a rigid member having a fixed shape, the intraoral illumination device can be mounted on the forward end of the handpiece whether it be an air turbine handpiece, a micromotor handpiece, a scaler handpiece, or the like, and thus a low-cost handpiece can be constructed.

According to the present invention, since the light emitted from a remote light source is guided through a light guide member to the adapter, the light source can be placed at a suitable distance away from the light exit end of the light guide member, which serves to enhance the operability of the instrument and ensures good visibility.

According to the present invention, since the adapter is provided with a filter plate having a plane surface perpendicular to the axis direction of the dental instrument body, the clinician can easily recognize the lesion by observing only the fluorescence passed through the filter plate. In this way, since the intraoral illumination device of the present invention can be used in combination with the filter plate that rejects only the excitation light or that passes fluorescence, there is no need to use eyeglasses or goggles equipped with such a filtering function as in the prior art; in particular, when selectively using a plurality of wavelengths, low-cost filter plates that match the respective wavelengths are be prepared from which a suitable one is selected for use.

Further, according to the present invention, when the dental instrument is equipped with an illuminating means for illuminating the lesion, the adapter is mounted at a position that interrupts the illumination light emitted from the illuminating unit, or more specifically, in the case of the existing handpiece equipped with an illumination light radiating function, at a position that faces the exit end from which the light emerges; accordingly, the clinician can use the handpiece without substantially changing the radiating angle and position of the existing illumination light.

According to the present invention, the dental instrument is one selected from among a dental air turbine handpiece, a dental micromotor handpiece, a dental scaler handpiece, a dental three-way syringe, a dental mirror, a vacuum syringe, a dental photo-polymerization device, a laser handpiece, and a dental tooth cleaning device, and with any of these instruments, lesions can be easily detected.

For example, since light of a wavelength near 400 nm is used as the excitation light, the fluorescence characteristic of dental caries, tartar, or plaque can be efficiently excited. The excitation light thus provides illumination light most suitable for use with a dental instrument, such as a dental air turbine handpiece, a dental micromotor handpiece, a dental scaler handpiece, a laser handpiece, or a dental tooth cleaning device, that is designed to remove such lesions. The wavelength near 400 nm can be easily obtained from an LED or a semiconductor laser such as an LD. In particular, light of 405-nm wavelength can be obtained from a semiconductor device for DVD. Further, in the case of a laser handpiece, the excitation light or the illumination light can be used as a guide beam.

Furthermore, if intraoral illumination devices are constructed each having a shape specifically designed for use, for example, with an air turbine handpiece or a scaler handpiece, the adapter light source specifically designed for each kind of handpiece needs only to be attached to the handpiece each time it is used; rather than preparing one handpiece equipped with lighting for each purpose, preparing one handpiece with no lighting for each purpose and one intraoral illumination device of the present invention for each handpiece is advantageous in terms of cost.

Since the intraoral illumination device of the present invention can also be mounted on a dental three-way syringe and a vacuum syringe, a dentist treating a tooth using a drilling instrument can clearly observe the dental lesion without the operability of the drilling instrument being degraded because of the use of the illumination device. This is because the dental three-way syringe and the vacuum syringe are instruments usually used by hygienists, the three-way syringe for spraying water and air to the treatment area and the vacuum syringe for evacuating fluids and debris from the treatment area, and both instruments are used with their forward ends pointed toward the treatment area. Accordingly, if the excitation light source is mounted on these instruments, the excitation light source need not be mounted on the drilling instrument that the dentist uses, and therefore the operability is not degraded.

BRIEF DESCRIPTION OF THE DRAWINGS

FIGS. 17A and 17B are diagrams for explaining the basic structure according to a third embodiment in which the present invention is applied to a scaler handpiece.

FIGS. 18A and 18B are diagrams for explaining a 13th specific example relating to the mounting of the light radiating unit at the forward end of the handpiece according to the third embodiment.

FIGS. 39A and 39B are diagrams for explaining a 28th specific example in which a power supply separated type intraoral illumination device according to a 10th embodiment of the present invention is mounted on a handpiece body.

FIGS. 43A and 43B are diagrams for explaining a 32nd specific example in which the intraoral illumination device of the 26th specific example is converted to a power supply separated type.

BEST MODE FOR CARRYING OUT THE INVENTION

Before describing the embodiments of a dental diagnostic and treatment apparatus according to the present invention, the principle of how intraoral lesions can be distinctively detected will be described with reference to FIGS. 59 to 61.

Figure 59:
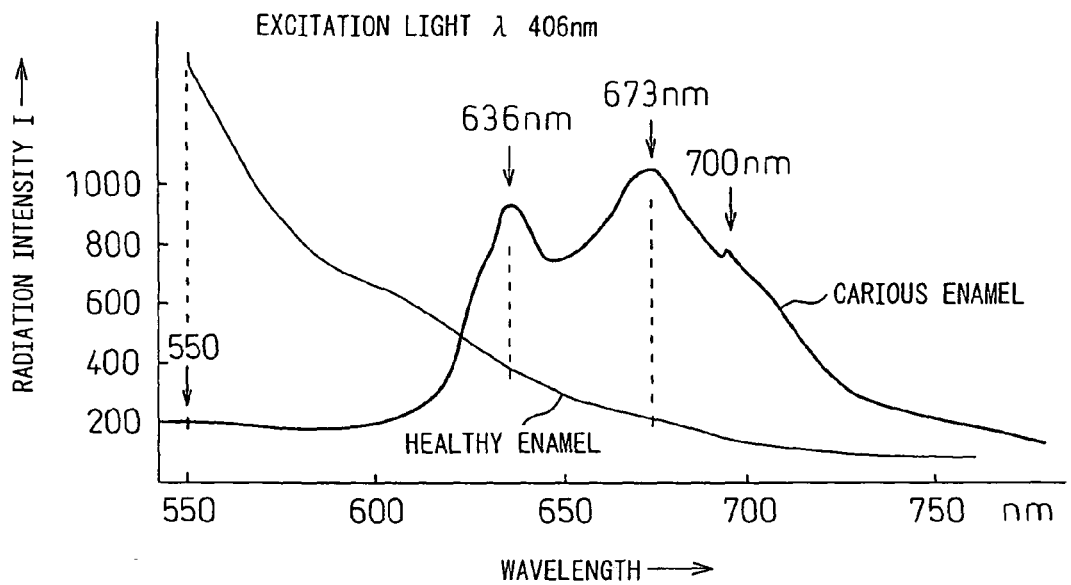
FIG. 59 is a graph for explaining the fluorescing characteristics of healthy enamel and carious enamel with respect to the radiation of excitation light.

FIG. 59 shows a graph for explaining the fluorescing characteristics of healthy enamel and carious enamel with respect to the radiation of excitation light. The graph shows how the fluorescence emission from a tooth changes depending on the condition of the tooth when the tooth is illuminated with excitation light having a specific wavelength. Here, radiation intensity I expressed in terms of a relative value of the radiation reflected by a tooth for the wavelength expressed in nm is plotted for the enamel of a carious tooth for comparison with the enamel of a healthy tooth. Incident radiation, i.e., the excitation light, has a wavelength of 406 nm.

As can be seen from the graph of FIG. 59, the two curves differ from each other. In particular, the curve of the radiation intensity for the enamel of the carious tooth shows three distinct peaks at 636 nm, 673 nm, and 700 nm, respectively. Noting the difference in fluorescence behavior between the enamel of the healthy tooth and the enamel of the carious tooth, it is seen that the reflections at 636 nm, 673 nm, and 700 nm, are noticeable, that is, these red components of fluorescence are enhanced; therefore, by observing these red components, the presence or absence of caries and the approximate degree of progression of the caries can be determined.

Figure 60:
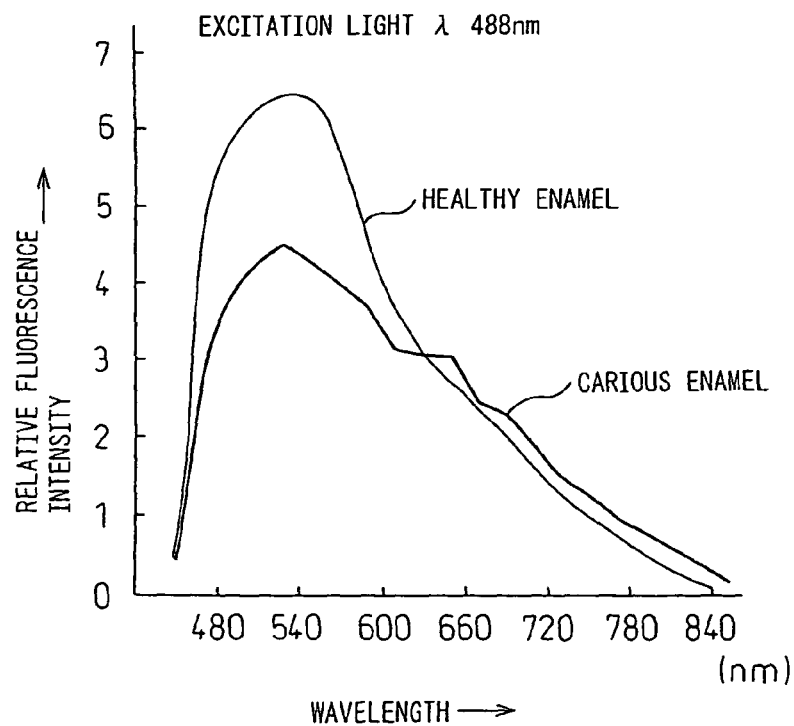
FIG. 60 is a graph for explaining another example relating to the fluorescing characteristics of healthy enamel and carious enamel with respect to the radiation of excitation light.

FIG. 60 shows a graph for explaining another example relating to the fluorescing characteristics of healthy enamel and carious enamel with respect to the radiation of excitation light. The graph shows how the fluorescence emission from a tooth changes depending on the condition of the tooth when the tooth is illuminated with excitation light having a specific wavelength. In FIG. 60, radiation intensity expressed in terms of a relative value of the radiation reflected by a tooth for the wavelength expressed in nm is plotted for the enamel of a carious tooth for comparison with the enamel of a healthy tooth. In this example, the incident radiation, i.e., the excitation light, has a wavelength of 488 nm.

As can be seen from the graph of the fluorescing characteristics shown in FIG. 60, the two curves differ from each other, but the way they differ is different from the graph of the fluorescing characteristics shown in FIG. 59. The radiation intensity curves for the healthy enamel and the carious enamel both exhibit peaks near the wavelength of the excitation light, but the heights of their peaks are different. Accordingly, utilizing the difference in fluorescence reflection intensity between the enamel of the healthy tooth and the enamel of the carious tooth, the presence or absence of caries and the approximate degree of progression of the caries can be determined.

In this way, by utilizing the difference in fluorescent behavior or the difference in reflection intensity arising between the healthy enamel and the carious enamel when illuminated with the radiation, a determination can be made as to whether the tooth under examination is a healthy tooth or a carious tooth.

Figure 61:
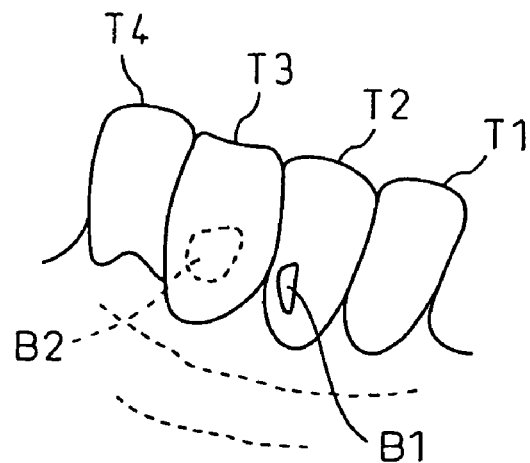
FIG. 61 is a diagram for explaining dental lesions in an oral cavity.
Figure 62:
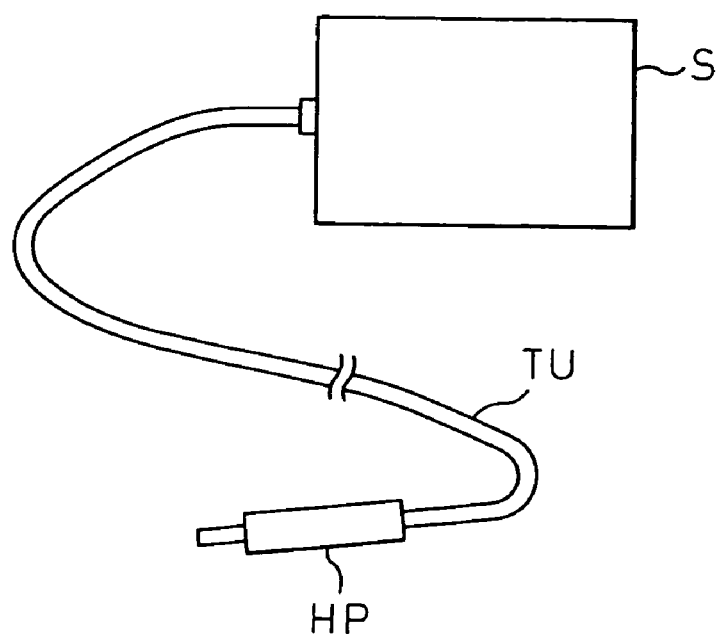
FIG. 62 is a diagram for explaining the basic configuration of an intraoral treatment apparatus equipped with a handpiece.

FIG. 61 illustrates how a dental lesion, for example, a carious tooth, or a tooth coated with tartar or plaque, shows when illuminated with excitation light. In the figure, a row of teeth in an oral cavity is shown by way of example; more particularly, a row of teeth consisting of teeth T1 to T4 is shown as a representative example. In the example shown in FIG. 61, carious portions B1 and B2 are present in the teeth T2 and T3, respectively. The carious portion B1 represents the case of advanced caries forming a cavity in the tooth (indicated by a solid line), while the carious portion B2 shows the case of caries formed inside the tooth (indicated by a dashed line).

Here, when excitation light of a specific wavelength is radiated, fluorescence is emitted from the teeth. In this case, since the fluorescence reflection intensity differs between the healthy portion and the carious portion as shown by the graphs of FIGS. 59 and 60, if the clinician visually inspects the portions by wearing eyeglasses or goggles having a filtering function capable of detecting the fluorescence or by using a protective plate attached to the handpiece and equipped with such a filtering function, the clinician can visually recognize the carious portions B1 and B2 by distinguishing them from the healthy portions. The filtering function here need only to have a characteristic that simply cuts off the wavelength of the excitation light. For example, in the case of the excitation light of 405 nm, the filtering function can be accomplished by a filter that passes only wavelengths longer than 440 nm.

The fluorescence intensity of the carious portion B2 appears weaker than that of the carious portion B1. Accordingly, by continuing to radiate the excitation light during the treatment, the clinician can detect the presence of the carious portions B1 and B2 and can easily determine which of the carious portions should be treated first. Furthermore, even after starting the treatment, the clinician can locate the treatment target area and keep track of the progression of the treatment, eliminating the possibility of a portion of the caries being left untreated or the tooth being drilled more than necessary. The efficiency of the treatment work also increases because the clinician does not need to change the treatment instrument as the treatment progresses. Since a carious portion shows a fluorescent color different from the color of the normal portion, basically the portion emitting that different color is treated. This is also true of a portion coated with tartar or plaque.

Example of dental lesions include caries, sclerotic dentin, tartar, plaque, biofilm, teeth chipping, and cracking; the light having a specific wavelength that exhibits a difference in fluorescence behavior or reflection intensity when radiated to such lesions is, for example, light in the near ultraviolet region of 405±50 nm, the blue region of 470±30 nm, the red region of 700±100 nm, the infrared region, or the near infrared region, but the wavelength is not limited to any one of these wavelengths. Here, light in the infrared region or the near infrared region may be used as the excitation light, but it is also possible to observe reflections of infrared radiation itself. The above are only examples, and the present invention is not limited to any particular example.

These lights can be easily generated using light-emitting devices such as light-emitting diodes (LEDs) or semiconductor laser devices including laser diodes (LDs), and these devices can be formed into a device module having a lens and used as a compact light source. White LEDs may be used as the LED devices. Further, other than the above devices, white light extracted from a lamp light source, for example, a halogen lamp, can also be used. This can be accomplished by combining the light source with an optical filter that can extract the desired wavelength.

For caries detection, the excitation light having, for example, the specific wavelength of 405 nm can be used, and the carious lesion can be detected by detecting the fluorescence emission from it; sclerotic dentin also can be detected by detecting the fluorescence emission occurring due to the radiation of the above excitation light. Tartar, plaque, and biofilm also can be detected by radiating the excitation light and detecting the resulting fluorescence. For tartar and plaque, if infrared light that can show details is radiated, the state of their formation becomes clearly visible and the presence of tartar or plaque can thus be recognized.

For the detection of tartar, plaque, and biofilm, when light of 400±30 nm, preferably 405 nm or 375 nm, is radiated, such lesions can be clearly identified, and therefore, the light of this wavelength is best suited as the light to be emitted from the light radiating means of a handpiece such as a scaler. In this case, if the target area is observed through an optical filter that passes wavelengths longer than 450 nm, the observation can be done with enhanced clearness because the excitation light emitted at 400±30 nm, preferably at 405 nm or 375 nm, is cut off. This cutoff wavelength is only one example, and the present invention is not limited to this particular example.

Further, if green or greenish light is radiated, lesions such as teeth chipping and cracking can be observed with enhanced clearness. Furthermore, since the intensity of reflected light and the degree of absorption differ depending on the portion illuminated with the light, the presence of a lesion can also be identified by radiating light of a wavelength that exhibits a clear difference in reflection or absorption and by detecting the difference.

It has earlier been described that when checking the presence of a lesion, the clinician visually inspects the target area by wearing eyeglasses or goggles having a filtering function capable of detecting the fluorescence occurring due to the excitation light or by using a protective plate attached to the instrument and equipped with such a filtering function; in this case, only the fluorescence is detected and, to the eye of the clinician, the lesion area appears floating while the surrounding area appears dark. As a result, while the lesion can be clearly identified, the condition of healthy portions cannot be detected, and also, the position of the lesion cannot be accurately determined.

However, if the wavelength of the excitation light for illuminating the lesion is within the visible region, then without specifically using an instrument having a filtering function for detecting the fluorescence, the clinician can observe the lesion showing a color different from the color of its surroundings and can also recognize the condition around the lesion in accordance with the color of the excitation light.

Further, by performing visual observation using eyeglasses or goggles equipped with a filtering function that blocks the transmission of the excitation light or a protective plate attached to the instrument and equipped with such a filtering function, the clinician can recognize the condition of the lesion by the fluorescence from the lesion; furthermore, when only the excitation light is radiated, the clinician can view the condition around the lesion by the ambient light entering the oral cavity, without interference by the radiation of the excitation light. On the other hand, when the white light for illumination is radiated simultaneously with the excitation light, it becomes possible to accurately grasp not only the condition of the lesion but also the condition of the tissue around the lesion, and further, since the area surrounding the lesion is brightly illuminated, it becomes easier to recognize the condition around the lesion. The color of the tissue around it can also be rendered faithfully.

Further, only one light-emitting device that emits light of a designated wavelength may be provided, but if a plurality of light-emitting devices that emit lights of different wavelengths are provided, various radiation patterns such as selective radiation of only the excitation light of specific wavelength, switching of the radiation to excitation light of different wavelength, and switching of the radiation between the illumination light and the excitation light can be achieved by controlling the driving of the light-emitting devices by operating a selector switch. In the case of switching the radiation between the illumination light and the excitation light, the illumination of the oral cavity and the detection of the lesion can be performed simultaneously by controlling the radiation of the illumination light and the excitation light in a time-division fashion.

Next, a first mode of the dental diagnostic and treatment apparatus for intraoral treatment according to the present invention will be described below with reference to first to seventh embodiments relating to examples in which the present invention is applied to a handpiece equipped with a light radiating means that can radiate the light capable of distinctively detecting intraoral lesions as described above.

In the present invention, the light radiating means is a means for radiating light and includes at least a light source for emitting excitation light, and may comprise only the light source or may comprise, in addition to the light source, a radiating part from which the excitation light emitted from the light source is radiated toward the lesion.

The radiating part is, for example, a light exit face of a light guide member for guiding the light emitted from the light source and for radiating the light toward the lesion, or the forward end of an optical fiber (or if an optically transmissive member to which the light is guided through the light guide member or the optical fiber, and from which the light is radiated toward the lesion, is provided, then the optically transmissive member), or a filter for extracting light of a designated wavelength from the light emitted from the light source and for radiating the extracted light toward the lesion.

The light source is, for example, a light-emitting device, and may comprise a single light-emitting device or a plurality of light-emitting devices.

Embodiment 1

Figure 1A:
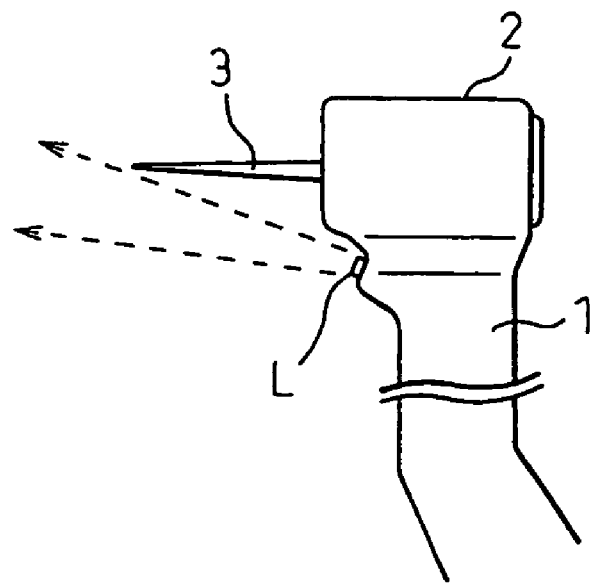
FIGS. 1A and 1B are diagrams for explaining the basic structure according to a first embodiment in which the present invention is applied to an air turbine handpiece.
Figure 1B:
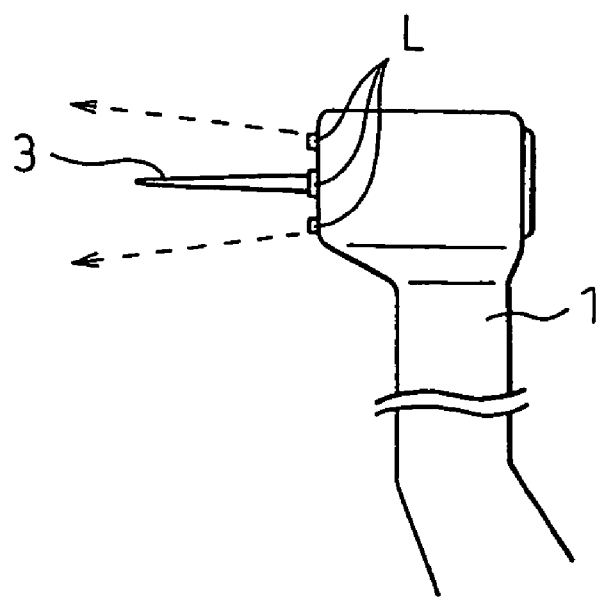

The first embodiment concerns the case where the light radiating means according to the present mode is applied to an air turbine handpiece; FIGS. 1A and 1B show the basic structure of the air turbine handpiece with the light radiating means mounted in its head.

In FIGS. 1A and 1B, reference numeral 1 is the handpiece body, 2 is the handpiece head, and 3 is a treatment tool such as a bar (one example of a diagnostic/treatment tool). In FIGS. 1A and 1B, a portion of the handpiece at the forward end thereof is shown, and for simplicity of explanation, the other portions are not shown here, but actually the handpiece is provided, at the end opposite from the head 2, with a joint which is detachable from the handpiece 1 and which is connected via a tube to a supply device such as an air supply device.

In FIG. 1A, the light radiating means comprises a light-emitting device L constructed from an LED or a semiconductor laser; here, the light-emitting device L is mounted exposed in one specific position near the handpiece head 2 to which the treatment tool 3 is attached. The mounting position of the light-emitting device L is tilted by a certain angle relative to the axis of the treatment tool 3 so that, when the treatment tool 3 is attached, the light emitted from the light-emitting device L as shown by dashed lines in the figure illuminates the area forward of the treatment tool 3 in the axial direction thereof. The light-emitting device L may be covered with an optically transmissive protective cover. Here, only one light-emitting device L may be provided if its light output is sufficient, but if the light output is not sufficient, a plurality of light-emitting devices L may be used in order to provide the necessary output. Further, when using a plurality of light-emitting devices L, light-emitting devices of different wavelengths may be combined for use. It is also possible to use a single light-emitting device that can emit light at different wavelengths.

On the other hand, FIG. 1B shows an example in which the light radiating means comprises a plurality of light-emitting devices L; here, the light-emitting devices L are mounted around the periphery of the forward end of the handpiece head 2 in such a manner as to encircle the axis of the treatment tool 3, with the light emitting direction of each light-emitting device L oriented substantially parallel to the tool axis. In the case of FIG. 1A, a shadow of the treatment tool 3 may be formed, depending on the mounting angle of the light-emitting device L, but in the case of FIG. 1B, since the plurality of light-emitting devices L are arranged so as to encircle the treatment tool 3, the light is directly projected from each light-emitting device L to illuminate the area forward of the treatment tool 3 as shown by a dashed line in the figure, so that a shadow of the treatment tool 3 is not formed.

Figure 2:
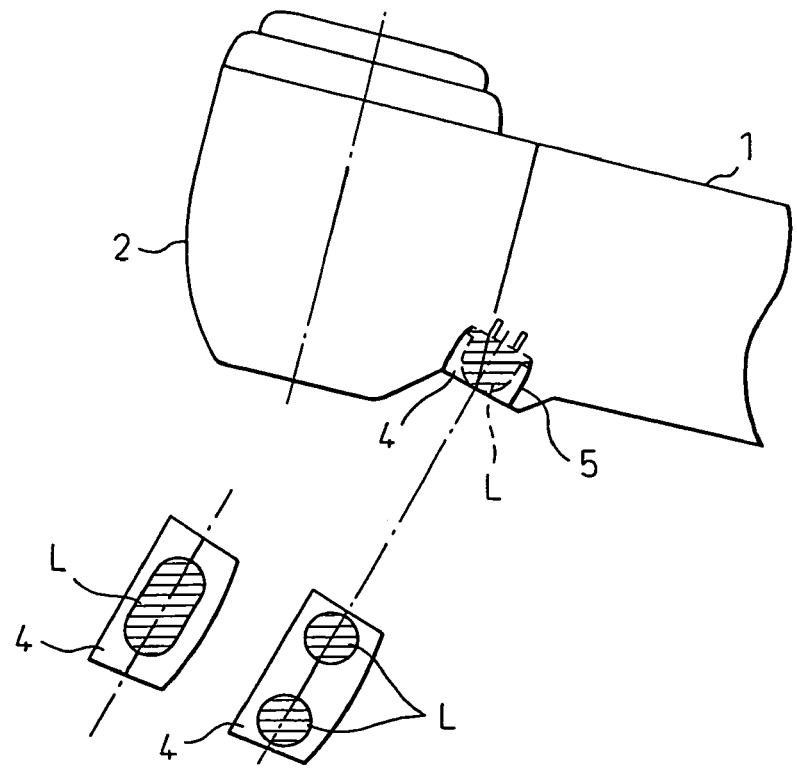
FIG. 2 is a diagram for explaining a first specific example relating to the mounting of a light radiating unit at the forward end of the handpiece according to the first embodiment.

Next, FIG. 2 shows a first specific example in which the light-emitting device L as the light radiating means of the handpiece is mounted in one specific position shown in FIG. 1A. In FIG. 2 also, the portion centering around the handpiece head 2 is shown.

As shown in FIG. 2, a recessed portion 4 which is open to the same side as the treatment tool mounting side is provided in a position near the joining portion between the handpiece body 1 and the handpiece head 2. The recessed portion 4 is chosen to have a size that can just accommodate the light-emitting device L, and the inner wall surfaces of the recessed portion 4 are coated with a reflective material 5 by plating or like means. Here, the opening of the recessed portion 4 may be covered with a transparent protective member.

The terminals of the light-emitting device L mounted inside the recessed portion 4 are connected to power supply wiring lines, not shown, which extend through the interior of the handpiece body 1. The wiring lines are routed to the supply device through the tube connected to the joint of the handpiece, and the on/off operation of the light-emitting device L is controlled by operating, for example, a switch mounted on the handpiece body 1. Alternatively, the on/off control may be performed using a separately provided switch.

The light-emitting device L to be mounted inside the recessed portion 4 is constructed from an LED or a semiconductor laser that emits light in the near ultraviolet region of 405±50 nm, the blue region of 470±30 nm, the red region of 700±100 nm, the infrared region, or the near infrared region, as previously described. Here, only one such light-emitting device L may be provided, but if the light output is not sufficient, one large light-emitting device may be mounted as shown in the front view of the light-emitting device in FIG. 2. Alternatively, a plurality of light-emitting devices that emit light of the same wavelength or of different wavelengths may be mounted as shown in the front view of an alternative example of the light-emitting device in FIG. 2.

When mounting the plurality of light-emitting devices L inside the recessed portion 4, the light-emitting devices may be chosen to emit light at respectively different wavelengths. In that case, the handpiece can be conveniently used to treat different kinds of lesions by operating a switch provided in the wiring path. Further, some of the plurality of light-emitting devices may be used only for illuminating purposes. In that case, the light-emitting devices L for illuminating purposes are turned on to observe the oral cavity, and when an area that appears to be a lesioned area is found, the lighting can be immediately switched to the excitation light, which is convenient.

Figure 3:
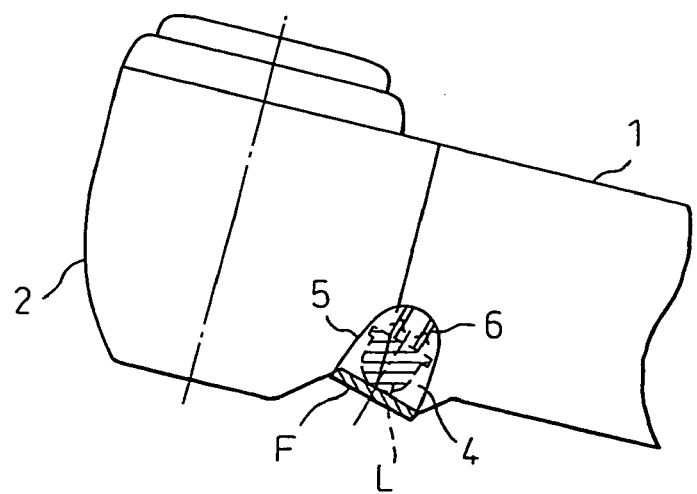
FIG. 3 is a diagram for explaining a second specific example relating to the mounting of the light radiating unit at the forward end of the handpiece according to the first embodiment.

In the first specific example shown in FIG. 2, an LED or a semiconductor laser light-emitting device is used as the light-emitting device L; on the other hand, FIG. 3 shows a second specific example in which a lamp light source such as a halogen lamp is used as the light-emitting device L. The handpiece shown in FIG. 3 is essentially the same in structure as the handpiece shown in FIG. 2, but differs in that the light-emitting device L mounted in the recessed portion 4 is, for example, a halogen lamp.

The connecting terminals 6 of the halogen lamp are connected to connecting terminals (unnumbered) provided in the handpiece 1, and the lamp is thus held fixed in place. Then, a detachable optical filter F for extracting desired excitation light from the light produced by the halogen lamp is mounted in the opening of the recessed portion 4 of the handpiece 1. If the optical filter F is replaced by a different optical filter F that selects a different wavelength, excitation light of that different wavelength can be radiated. If the optical filter F is replaced by a protective member formed merely from transparent glass or the like, the lamp can be used as a generally used illumination device.

In the first and second specific examples described above, the light-emitting device L as the light illuminating means is fixedly mounted, but there are cases where the light illuminating means is not needed, or where it is desired to change the kind of the excitation light to be emitted from the light-emitting device L, or there are even cases where it is desired to install merely an illumination device. To address these situations, FIGS. 4A and 4B show a third specific example in which the light illuminating means is made detachable from the handpiece head.

The structure of the handpiece of the third specific example is essentially the same as that shown in the first and second specific examples, but in the third specific example, the forward end portion of the handpiece head 2, including the recessed portion 4 in which the light-emitting device L is mounted, is constructed as a head detachable member 9 which is detachable from the head. An engaging member 11 which engages with an engaging portion formed on the head 2 is integrally formed with the head detachable member 9, and a screw hole 10 for securing the member 9 to the handpiece body 1 is also formed.

Figure 4A:
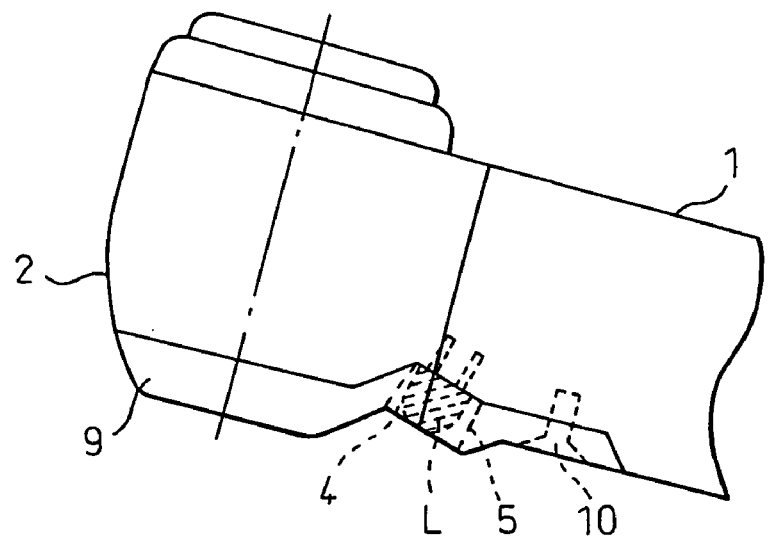
FIGS. 4A and 4B are diagrams for explaining a third specific example relating to the mounting of the light radiating unit at the forward end of the handpiece according to the first embodiment.
Figure 4B:
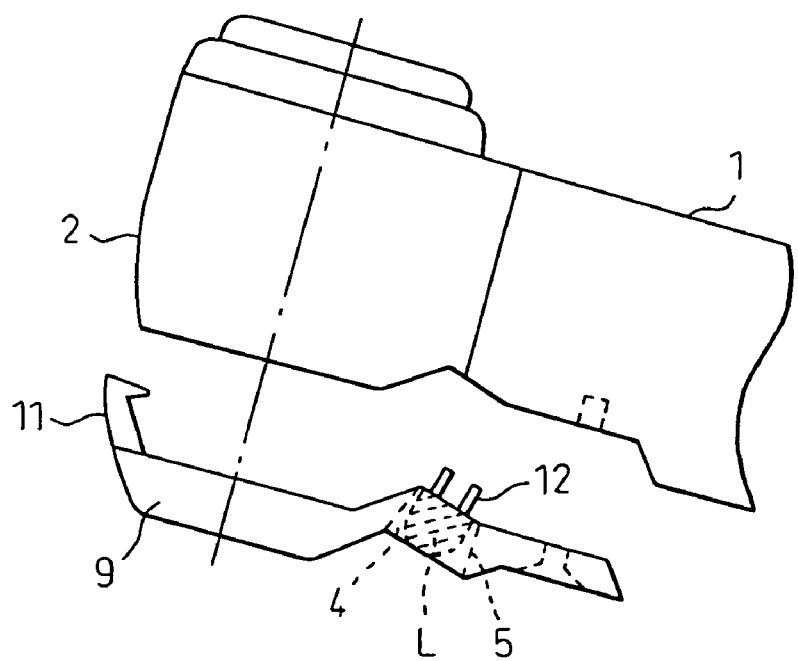

FIG. 4A shows the condition in which the head detachable member 9 is secured to the handpiece head 2, while FIG. 4B shows the condition in which the head detachable member 9 is removed from the handpiece head 2. The light-emitting device L is mounted inside the recessed portion 4 formed in the head detachable member 9, and is provided with connecting terminals 12 through which power is supplied to the light-emitting device L when the head detachable member 9 is secured to the handpiece head 2.

When the light illuminating means is not needed, the head detachable member 9 is replaced by a head detachable member in which the light-emitting device L is not mounted, or by a head detachable member in which the recessed portion 4 is not formed. On the other hand, when it is desired to change the kind of the excitation light to be emitted from the light-emitting device L, the head detachable member 9 is replaced by a head detachable member mounted with a light-emitting device for emitting a different kind of excitation light. Further, when it is desired to install merely an illumination device, the head detachable member 9 is replaced by a head detachable member in which a light-emitting device for emitting white light is mounted. Furthermore, if a head detachable member is constructed that is equipped with light-emitting devices such as LEDs for emitting excitation light of different wavelengths and a light-emitting device such as an LED for emitting white light, then it becomes possible to select a desired one of the light-emitting devices by operating a switch.

The first to third specific examples shown in FIGS. 2 to 4 above are each concerned with the case where the light-emitting device L is mounted in one specific position near the handpiece head 2 to which the treatment tool 3 is attached; next, referring to FIGS. 5 to 7, specific examples will be described below for the case where, as shown in FIG. 1B, a plurality of light-emitting devices L are mounted in such a manner as to encircle the axis of the treatment tool 3, with the light emitting direction of each light-emitting device L oriented substantially parallel to the tool axis.

Figure 5:
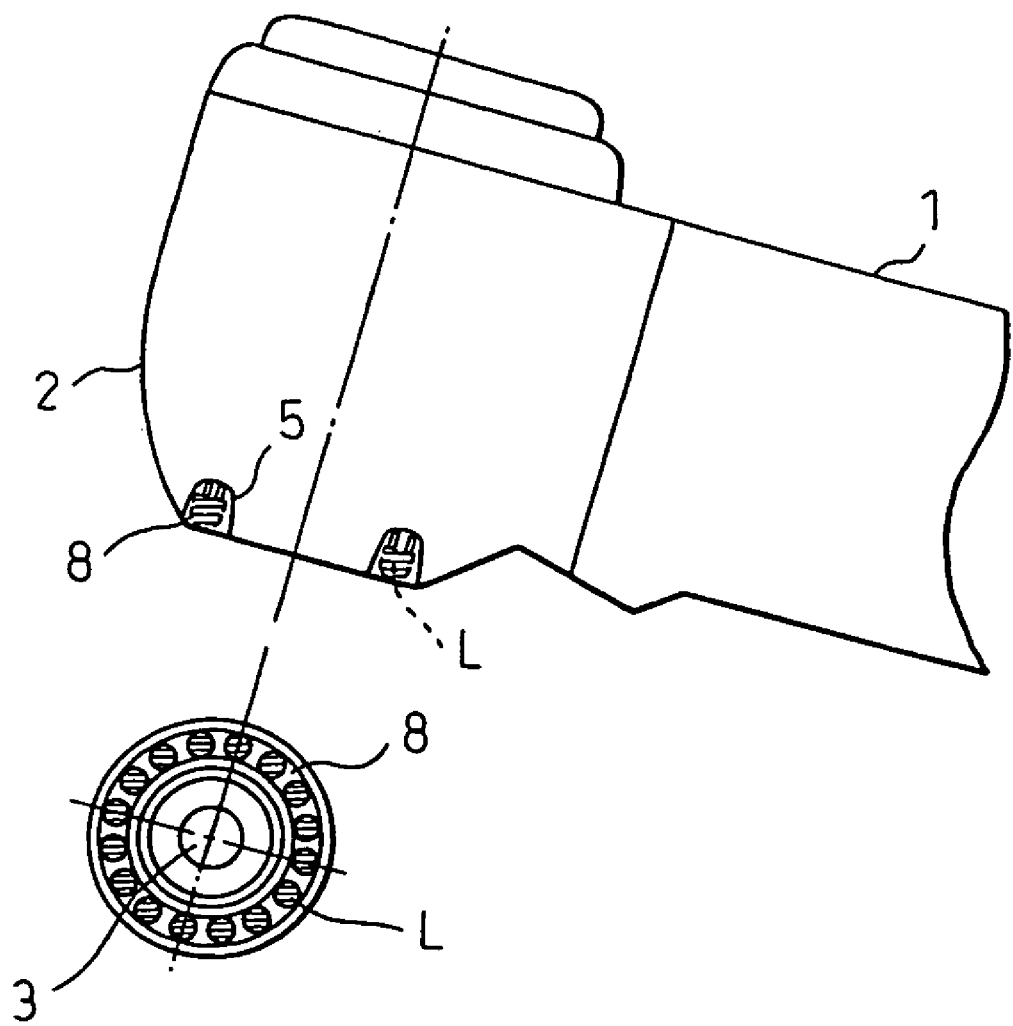
FIG. 5 is a diagram for explaining a fourth specific example relating to the mounting of the light radiating unit at the forward end of the handpiece according to the first embodiment.

FIG. 5 shows a fourth specific example; in FIG. 5, the handpiece is illustrated in the same way as that shown in FIG. 2. In the third specific example, the plurality of light-emitting devices L are mounted in a groove 8 formed around the periphery of the forward end of the handpiece head 2 in such a manner as to encircle the treatment tool 3, as shown in FIG. 5. The forward end of the handpiece head 2 as viewed from the position facing the tip of the treatment tool 3 is shown in FIG. 5. A plurality of recessed portions may be provided instead of the groove 8.

In the fourth specific example also, the open groove 8 is chosen to have a depth and width that can just accommodate the light-emitting devices L, and the inner wall surfaces of the groove 8 are coated with a reflective material 5 by plating or like means. Here, the opening of the groove 8 may be covered with a transparent protective member.

The terminals of the light-emitting devices L mounted inside the groove 8 are connected to power supply wiring lines, not shown, which extend through the interior of the handpiece body 1. The wiring lines are routed to the supply device through the tube connected to the joint of the handpiece, and the on/off operation of the light-emitting devices L is controlled by operating, for example, a switch mounted on the handpiece body 1. Alternatively, the on/off control may be performed using a separately provided switch.

The light-emitting devices L to be mounted inside the groove 8 are each constructed from an LED or a semiconductor laser that emits light in the near ultraviolet region of 405±50 nm, the blue region of 470±30 nm, the red region of 700±100 nm, the infrared region, or the near infrared region, as previously described. All of the plurality of light-emitting devices L may be constructed to emit light of the same wavelength, but alternatively, the plurality of light-emitting devices L may be constructed to emit light of different wavelengths. In the latter case, the handpiece can be conveniently used to treat different kinds of lesions by operating a switch provided in the wiring path. Further, some of the plurality of light-emitting devices may be used only for illuminating purposes. In that case, the light-emitting devices L for illuminating purposes are turned on to observe the oral cavity, and when an area that appears to be a lesioned area is found, the lighting can be immediately switched to the excitation light, which is convenient. Switching between the light-emitting devices may be performed automatically in a time-division fashion or manually by using a selector switch or the like.

Figure 6A:
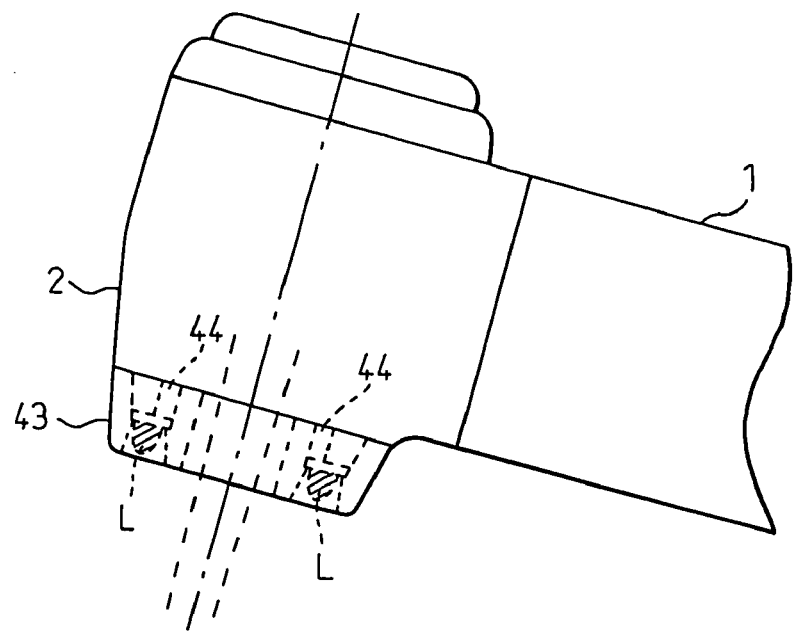
FIGS. 6A and 6B are diagrams for explaining a fifth specific example relating to the mounting of the light radiating means at the forward end of the handpiece according to the first embodiment.
Figure 6B:
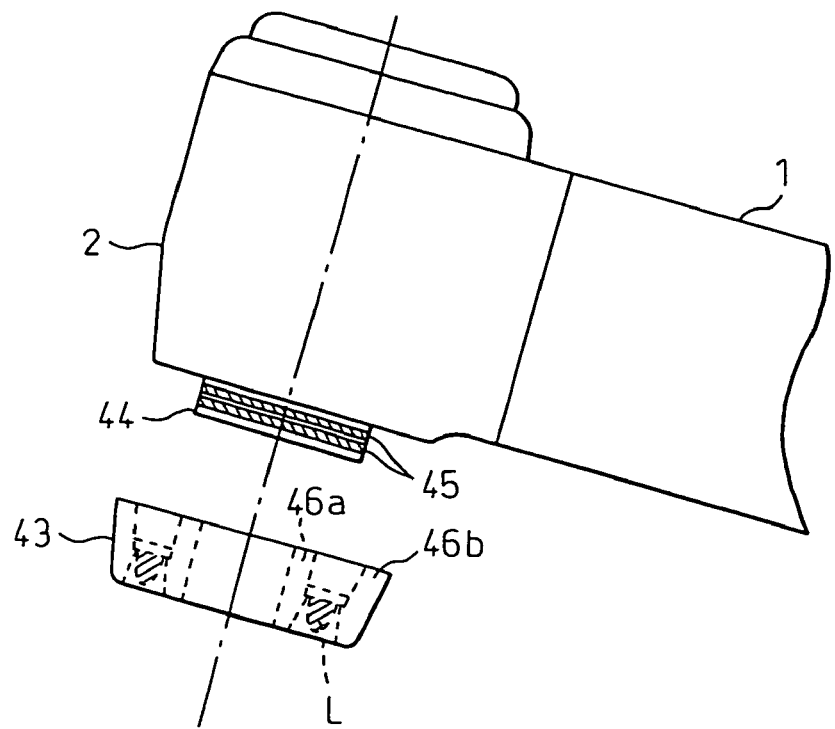
Figure 7:
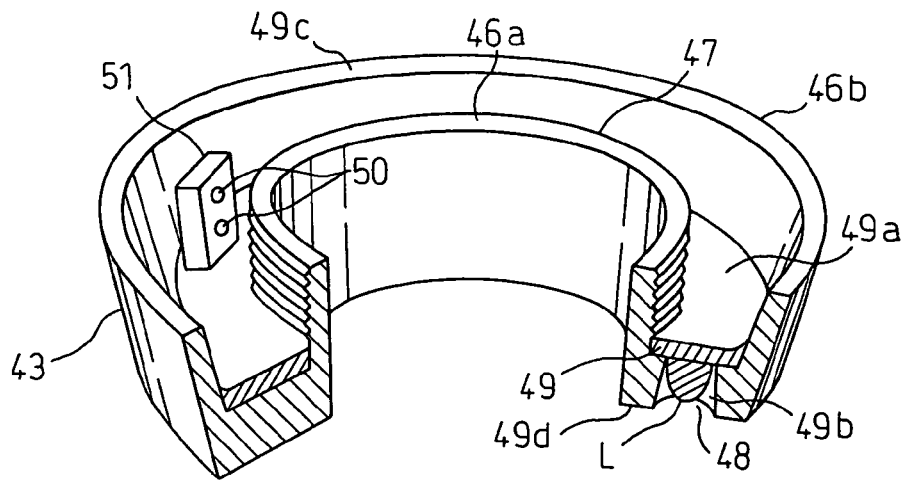
FIG. 7 is a perspective view for explaining the details of the light source section of the light radiating unit in the fifth specific example.

In the fourth specific example shown in FIG. 5, the light-emitting devices L as the light radiating means are fixedly mounted near the mounting position of the treatment tool, but there are cases where the light radiating means is not needed, or where it is desired to change the kind of the excitation light to be emitted from the light-emitting device L, or there are even cases where it is desired to install merely an illumination device; to address these situations, FIGS. 6A, 6B, and 7 show a fifth specific example in which the light radiating means is made detachable from the handpiece head.

In the handpiece structure according to the fifth specific example, a head detachable member 43 in which the light-emitting devices are mounted is constructed so that it can be detachably mounted on the head 2 by screwing in order to make the light radiating means replaceable and detachable with respect to the handpiece head 2. For example, as shown in FIG. 7, the plurality of light-emitting devices L are mounted on an annular wiring substrate 49 formed to conform with the shape of the forward end of the handpiece head 2. The wiring substrate 49 is attached to the forward end of the handpiece head 2 by using the head detachable member 43, and the light-emitting devices L are thus connected to power supply wiring lines (not shown).

FIG. 7 is a perspective view, with portions broken away, of the structure shown in FIG. 6A in the fifth specific example. The head detachable member 43 is an annular member having a hollow space in its center through which to accommodate the treatment tool 3, and has an outer diameter approximately equal to that of the bottom of the handpiece head 2. A face 49c of the head detachable member 43, which faces the handpiece head 2 when mounted, is provided with an annular groove 49a conforming with the annular shape of the head detachable member 43, and the wiring substrate 49 is fitted into the annular groove 49a. A through hole 49b is formed in the bottom of the annular groove 49a at a position corresponding to the position where each light-emitting device L is mounted on the wiring substrate 49. The through hole 49*b* is formed in the bottom of the annular groove 49*a* through to an opposite face 49*d* of the head detachable member 43, i.e., the face on the side opposite from the open side of the annular groove 49*a*.

With the provision of the annular groove 49*a* in the head detachable member 43, a portion of the head detachable member 43 is formed as a head detachable inner wall member 46*a* along the inner circumference of the annular groove 49*a*, and a portion of the head detachable member 43 is formed as a head detachable outer wall member 46*b* along the outer circumference of the annular groove 49*a*. A threaded portion 47 for detachably screwing onto a head-side engaging portion 44 protruding from the bottom of the handpiece head 2 shown in FIGS. 6A and 6B is formed around the outer circumference of the head detachable inner wall member 46*a*. When mounting the head detachable member 43 on the handpiece head 2, the wiring substrate 49 with the light-emitting devices L facing the bottom side is fitted into the annular groove 49*a*, and the threaded portion 47 is screwed onto the head-side engaging portion 44.

The wiring substrate 49 is provided with a contact member 51 having contacts 50 which, when the head detachable member 43 is attached to the handpiece head 2, contact two ring-shaped connecting terminals 45 each formed from an electrically conductive strip member formed around the outer circumference of the head-side engaging member 44 shown in FIG. 6B. The contacts 50 are positioned so that when the head detachable member 43 is attached to the handpiece head 2, the contacts 50 contact the ring-shaped connecting terminals 45 at arbitrary positions along the outer circumference thereof to enable power to be supplied via the contacts. The contact member 51 may be provided on the wiring substrate 49, but alternatively, it may be provided on the head detachable member 43 and connected to the wiring substrate 49 so that power is supplied via the contacts.

Here, the plurality of light-emitting devices L are arranged in a ring so as to encircle the axis of the treatment tool 3, with each light-emitting device L being slightly tilted inwardly as shown in FIG. 6B so that the light emitted from the light-emitting device L is directed toward the tip of the treatment tool 3 when the treatment tool 3 is mounted. The light-emitting devices L mounted here are the same as those in the fourth specific example shown in FIG. 5.

According to the structure of the fifth specific example, since the light radiating means can be constructed to form part of the handpiece head 2, not only can the space for the light radiating means be reduced, but because of the use of the LEDs or semiconductor laser light-emitting devices, the cooling mechanism for the light source can be eliminated; as a result, the illuminating function can be added without increasing the size of the instrument such as a handpiece, and thus a compact, light-weight, and easy-to-use dental handpiece can be achieved.

While the earlier described fourth specific example shows the construction in which the light-emitting devices L are fixedly mounted in the handpiece head, the fifth specific example depicted in FIG. 7 above shows one example of the construction in which the light radiating means including the light-emitting devices is made detachable from the handpiece head.

Figure 8A:
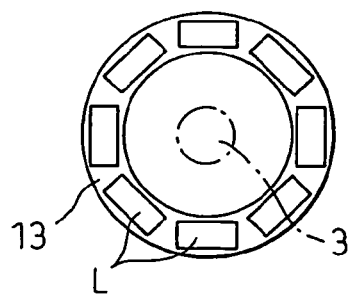
FIGS. 8A and 8B are diagrams for explaining a sixth specific example relating to the mounting of the light radiating unit at the forward end of the handpiece according to the first embodiment.
Figure 8B:
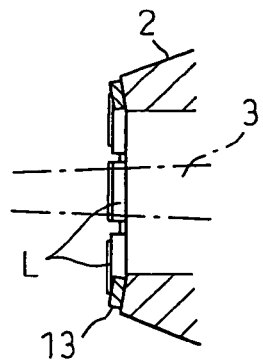

Next, FIGS. 8A and 8B show a sixth specific example in which the plurality of light-emitting devices L are mounted directly around the periphery of the forward end of the head in such a manner as to be exposed outside the head. The sixth specific example modifies the method of mounting the light-emitting devices in the fourth specific example and, as shown in FIG. 8A, for example, eight light-emitting devices are mounted on an annular wiring substrate 13 formed to conform with the shape of the forward end of the scaler handpiece head 2. The wiring substrate 13 is attached to the forward end of the handpiece head 2, and the light-emitting devices L are thus connected to the power supply wiring lines.

Here, the eight light-emitting devices L are arranged in a ring so as to encircle the axis of the treatment tool 3, with each light-emitting device L being slightly tilted inwardly as shown in the cross-sectional view of FIG. 8B so that the light emitted from the light-emitting device L is directed toward the tip of the treatment tool 3. The light-emitting devices L mounted here are the same as those in the fourth specific example shown in FIG. 5.

According to the structure of the sixth specific example, not only can the space for the light radiating means be reduced, but because of the use of the LEDs or semiconductor laser light-emitting devices, the cooling mechanism for the light source can be eliminated; as a result, the illuminating function can be added without increasing the size of the instrument such as a handpiece, and thus a compact, light-weight, and easy-to-use dental handpiece can be achieved.

The sixth specific example described above, like the earlier described fourth specific example, shows the construction in which the light-emitting devices L are fixedly mounted in the handpiece head; on the other hand, the fifth specific example depicted in FIG. 7 shows the construction in which the light radiating means including the light-emitting devices is made detachable. The fifth specific example shown in FIG. 7 is one example in which the light radiating means is made detachable based on the structure of the fourth specific example.

Figure 9A:
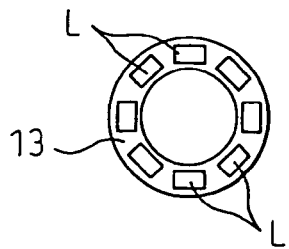
FIGS. 9A and 9B are diagrams for explaining a seventh specific example relating to the mounting of the light radiating unit at the forward end of the handpiece according to the first embodiment.
Figure 9B:
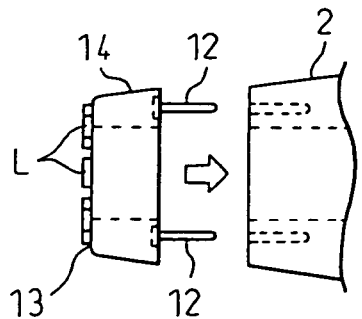

FIGS. 9A and 9B show a seventh specific example which is similar in structure to the sixth specific example shown in FIG. 8A, but differs in that the light radiating means is made detachable based on the structure of the sixth specific example. As shown in FIG. 9B, the forward end of the scaler handpiece head 2 is constructed as a head detachable member 14, and the wiring substrate 13 with the plurality of light-emitting devices L mounted thereon is attached to the forward end of the head detachable member 14. Connecting terminals 12 for supplying power to the light-emitting devices L are provided in such a manner as to protrude from the periphery of the opposite side of the head detachable member 14 from the side to which the wiring substrate 13 is attached.

Two connecting terminals 12 are shown in FIG. 9B, but actually a plurality of pairs of such connecting terminals are provided to match the number of light-emitting devices L mounted, and are inserted in the sockets formed in the handpiece head 2. By inserting the connecting terminals 12 into the sockets, the head detachable member 14 is mounted and held fixed in place. The method of selecting the kinds of the light-emitting devices L to be mounted on the head detachable member 14 is the same as that described in the third specific example shown in FIGS. 4A and 4B. When the light illuminating means is not needed, only the light-emitting devices L should be removed from the head detachable member 14 while leaving the connecting terminals 12 attached to it.

The first to seventh specific examples described above show the construction in which each light-emitting device L as the light radiating means is mounted so as to directly illuminate the area forward of the treatment tool 3. As opposed to these specific examples, the specific examples described below with reference to FIGS. 10 to 13 relate to the construction in which the light source as the light radiating means is mounted inside the handpiece body and the light emitted from the light source is guided through a light guiding member such as a fiber optic bundle up to the light exit face of the handpiece head.

Figure 10:
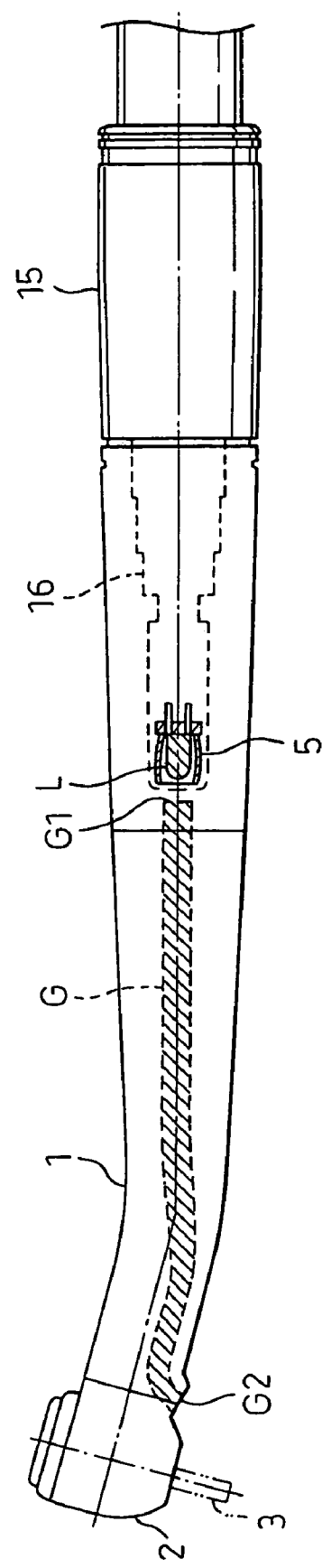
FIG. 10 is a diagram for explaining an eighth specific example relating to the mounting of the light radiating unit at the forward end of the handpiece according to the first embodiment.

In the eighth specific example shown in FIG. 10, the light-emitting device L is mounted at the center of the forward end of a base 16 which is detachably attached to the air turbine handpiece body 1 by means of a quick disconnect joint 15, i.e., a universal joint. A light entrance face G1 of the light guide member G installed within the handpiece body 1 is disposed in close proximity to the light-emitting device L. The light emitted from the light-emitting device L and falling on the light entrance face G1 is guided through the light guide member G to the handpiece head 2. The light exit face G2 of the light guide member G is disposed near the handpiece head 2, as in the case of the structure shown in FIG. 1A, and the light emerging from the light exit face G2 is projected toward the area forward of the treatment tool 3. Preferably, a diffuser is provided on the light exit face G2 in order to adjust the spreading of the light being projected forward. The diffuser may be formed from a lens-like member or by suitably shaping the forward end of the fiber optic bundle. It is also possible to cover it with an optically transmissive member having a roughened surface.

Figure 11:
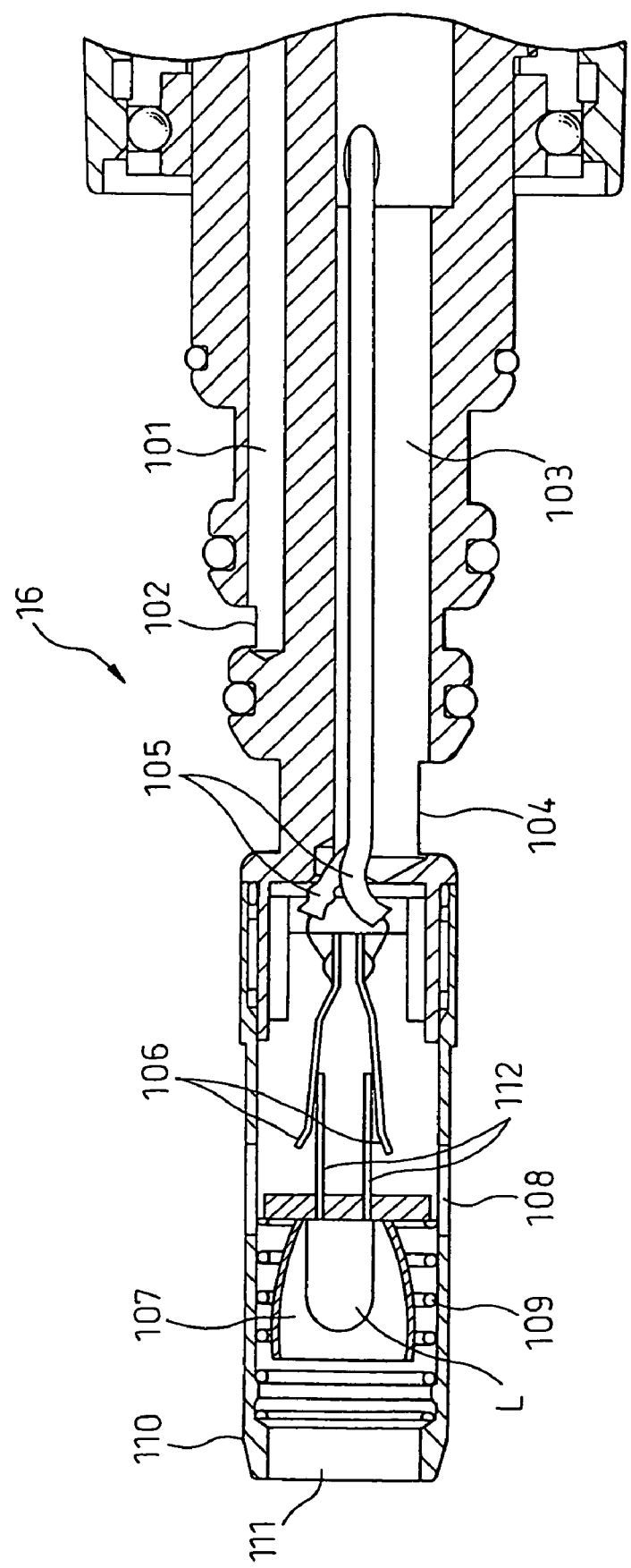
FIG. 11 is a diagram for explaining the details of the light source section of the light radiating unit in the eighth specific example.

FIG. 11 shows in detail how the light-emitting device L is mounted in the base 12 shown in the eighth specific example of FIG. 10. A cross-sectional view of an essential portion of the base 16 is shown in FIG. 11. A removable cap 110 is attached to the forward end of the base 16, and the light-emitting device L is mounted inside it. The light-emitting device L is provided with a reflective surface 107 which corresponds to the reflective member 5 shown in FIG. 10. The light-emitting device L is held in position by a spring 109 inside the cap 110, and the terminals 112 of the light-emitting device L are connected to electrical terminals 106. The electrical terminals 106 are connected via electrical lines 105 to an external power supply in the supply device which thus supplies power to the light-emitting device L.

An air conduit 103 for carrying supply air and cooling air and a water conduit 101 for carrying water are formed inside the base 16, and air and water are supplied through openings 104 and 102 into the handpiece body not shown. The cap 110 is formed with an air hole 108 through which the air flowing from the air conduit 103 and passing around the light-emitting device L is introduced to cool the light-emitting device L. The light from the light-emitting device L passes through the through hole 111 formed in the forward end of the cap 110 and falls on the light entrance face of the light guide in the handpiece body not shown.

When the light-emitting device L mounted in the forward end of the base 16 is an LED or a semiconductor laser, the method of selecting the light-emitting device is the same as that in the first specific example shown in FIG. 2, and therefore the description will not be repeated here. On the other hand, when a lamp light source such as a halogen lamp is used as the light-emitting device L, the construction of the light radiating means itself is the same as when the light-emitting device such as an LED is used, but an optical filter is mounted in the through hole at the forward end of the cap 110 in order to produce excitation light having a designated wavelength. When the light-emitting device is used to simply produce illumination light, the optical filter is not needed.

Figure 12:
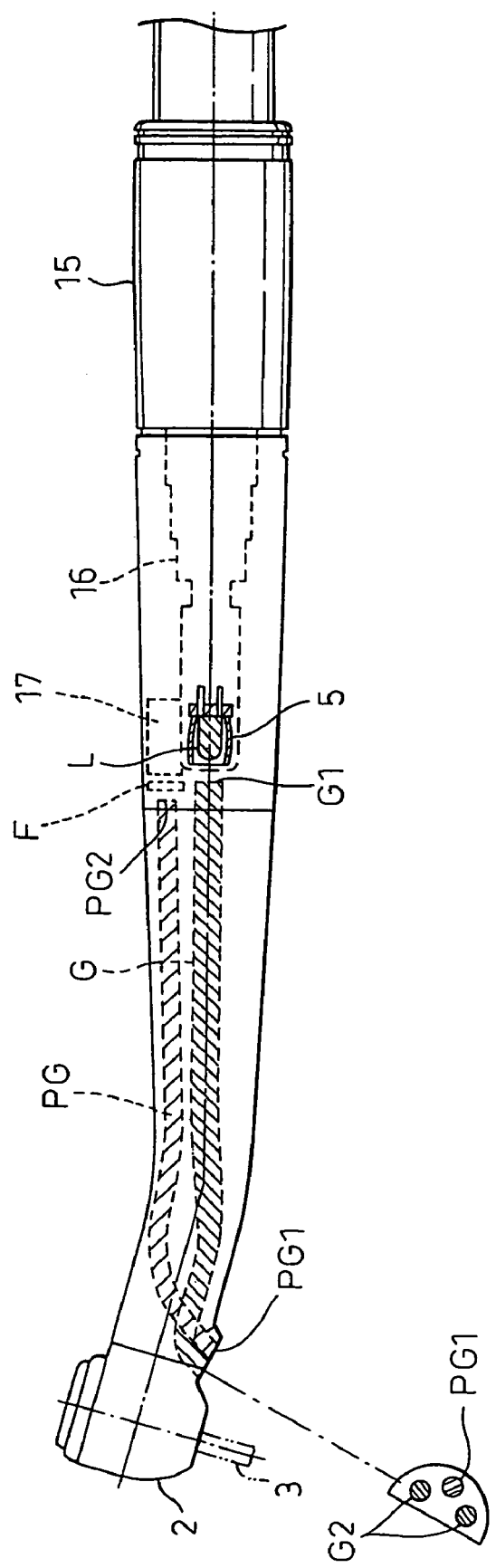
FIG. 12 is a diagram for explaining a ninth specific example relating to the mounting of the light radiating unit according to the first embodiment.

Next, as an application example of the eighth specific example shown in FIG. 10, a ninth specific example is shown in FIG. 12 in which an image capturing means is built into the handpiece body. The construction of the light radiating means of the ninth specific example is basically the same as that shown in the eighth specific example, except that an image capturing means that can capture an image of the area forward of the treatment tool is mounted in an empty space inside the handpiece body.

As shown in FIG. 12, an imaging device 17 such as a CCD is mounted inside the handpiece body 1 of the air turbine handpiece. An image guide member PG is provided extending parallel to the light guide member G provided for the light radiating means, and the light entrance face PG1 of the image guide member PG is positioned near the light radiating face G2 of the light radiating means, and receives fluorescence or reflected light coming from the area forward of the treatment tool 3. The light exit face PG2 of the image guide member PG is disposed facing the imaging device 17 so that the received fluorescence passed through an optical filter F enters the imaging device 17 which thus captures the fluorescent image of the area forward of the treatment tool 3. By displaying this fluorescence image on a monitor located remotely from the handpiece, the clinician can observe the condition of the intraoral lesion located forward of the treatment tool 3. When observing the reflected light, the optical filter F is not needed.

In the ninth specific example shown in FIG. 12, the light emitted from the light-emitting device L is radiated from the two light exit faces G2 near the handpiece head 2 to illuminate the area forward of the treatment tool 3, and the reflected light from that forward area is received at the light entrance face PG1 located between the two light exit faces G2. The location of the entrance face PG1 shown in FIG. 12 is only one example, and is not limited to this particular example.

Further, the mounting position of the imaging device 17 is not limited to the position shown in the ninth specific example, but the imaging device 17 may be mounted directly, for example, in a position near the handpiece head 2, where the imaging device 17 can be easily pointed toward the area forward of the treatment tool 3, without using the image guide member PG. In this case also, the optical filter F must be provided.

According to the structure of the ninth specific example, since the condition of the lesion can be observed on the monitor by radiating excitation light and viewing an image of the reflection of the excitation light captured by the imaging device 17, the lesion such as caries can be diagnosed or treated while observing the condition of the lesion.

Embodiment 2

While the first embodiment has been described with reference to the first to ninth specific examples in connection with the case where the light radiating means according to the present mode is applied primarily to an air turbine handpiece (FIGS. 8 and 9 show examples in which it is applied to a scaler), the second embodiment described hereinafter relates to the case where the light radiating means according to the present mode is applied to a micromotor handpiece.

There are two types of micromotor handpiece: the contra-angle handpiece in which the axis of rotation of the treatment tool (diagnostic tool) 3 is substantially at right angles to the axis of the grip of the micromotor, and the straight handpiece in which the axis of rotation of the treatment tool (diagnostic tool) 3 coincides with the axis of the grip of the micromotor. The former type is shown as a 10th specific example in FIG. 13, and the latter type is shown as an 11th specific example in FIG. 14.

Figure 13:
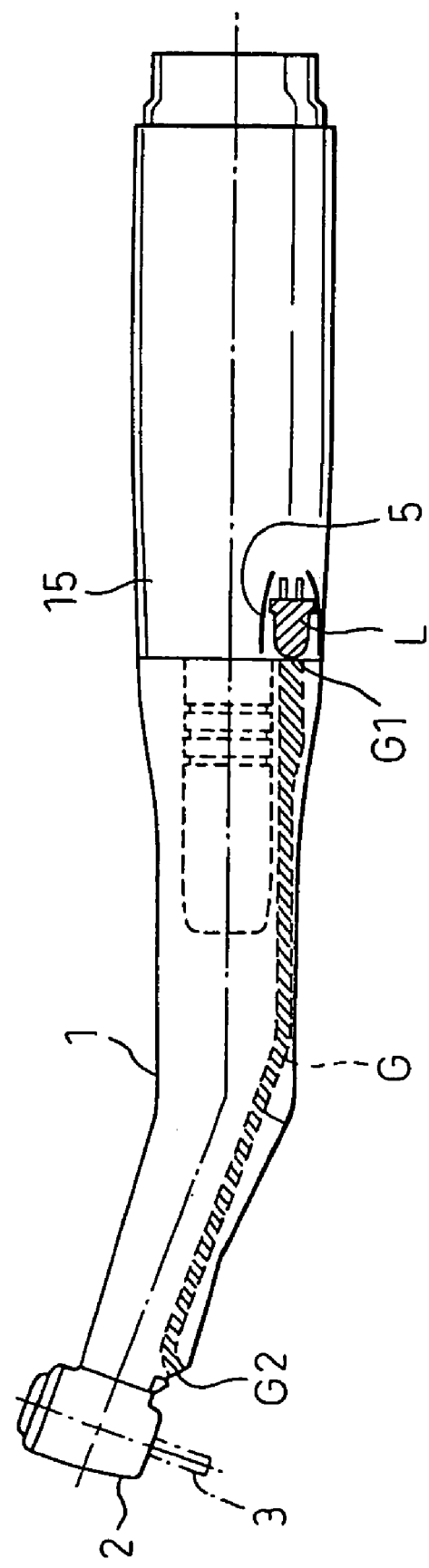
FIG. 13 is a diagram for explaining a 10th specific example relating to the mounting of the light radiating unit at the forward end of the handpiece according to a second embodiment in which the present invention is applied to a micromotor handpiece.

When mounting the light radiating means on the micromotor handpiece of the type according to the 10th specific example shown in FIG. 13, the light-emitting device as the light radiating means can be directly mounted in a position near the mounting portion of the treatment tool 3 at the forward end of the handpiece by directly employing the light-emitting device mounting method shown in the first to fifth specific examples of the foregoing first embodiment. In the 11th specific example shown in FIG. 14, the light-emitting device mounting method shown in the sixth and seventh specific examples of the foregoing first embodiment can be directly applied.

However, in the case of the micromotor handpiece, the axis of the grip of the micromotor passes through the center axis of the base 16 in the handpiece body 1. As a result, the light-emitting device L cannot be mounted at the forward end of the base 16 as illustrated in the eighth or ninth specific example of the foregoing first embodiment shown in FIG. 10 or 12, and hence, in the case of the micromotor handpiece, the light guide member G cannot be installed in the same manner as illustrated in the eighth or ninth specific example.

Figure 14:
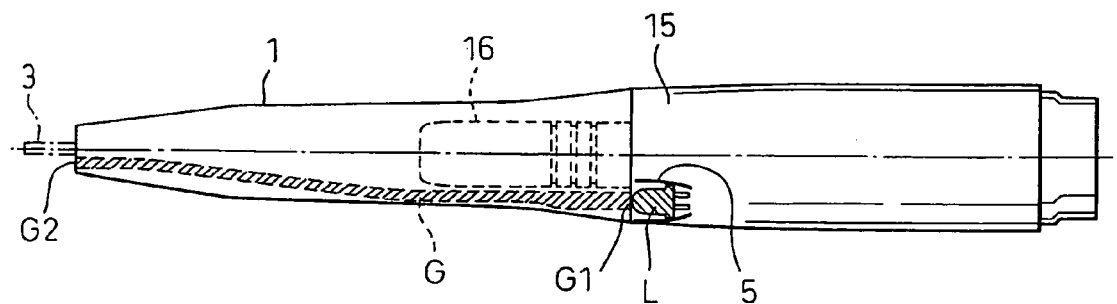
FIG. 14 is a diagram for explaining an 11th specific example relating to the mounting of the light radiating unit at the forward end of the handpiece according to the second embodiment.

Therefore, as shown in FIGS. 13 and 14, the light-emitting device L is mounted on the joint 15 at a position outside the position of the base 16. Then, with the light entrance face G1 of the light guide member G disposed facing the light-emitting device L, the light guide member G is installed in such a manner as to extend in parallel to the axis of rotation, and the light exit face G2, i.e., the other end of the light guide member G, is exposed at the forward end of the handpiece.

In the 10th specific example, as in the eighth specific example, the light exit face G2 is disposed near the handpiece head 2. On the other hand, in the 12th specific example, since there is no handpiece head, the light exit face G2 is disposed at the forward end of the handpiece body 1 so that the light can be projected in a direction substantially parallel to the treatment tool 3.

Here, in the case of the 11th specific example shown in FIG. 14, the light exit face G2 is arranged in one specific position at the forward end of the handpiece body 1, but when the light guide member D is formed, for example, from a fiber optic bundle, the light exit face G2 may be arranged around the periphery of the forward end face of the handpiece body 1 in such a manner as to encircle the treatment tool 3. By arranging the light exit face G2 in such an encircling shape, spot-like illumination can be converted into wide spreading illumination.

Figure 15:
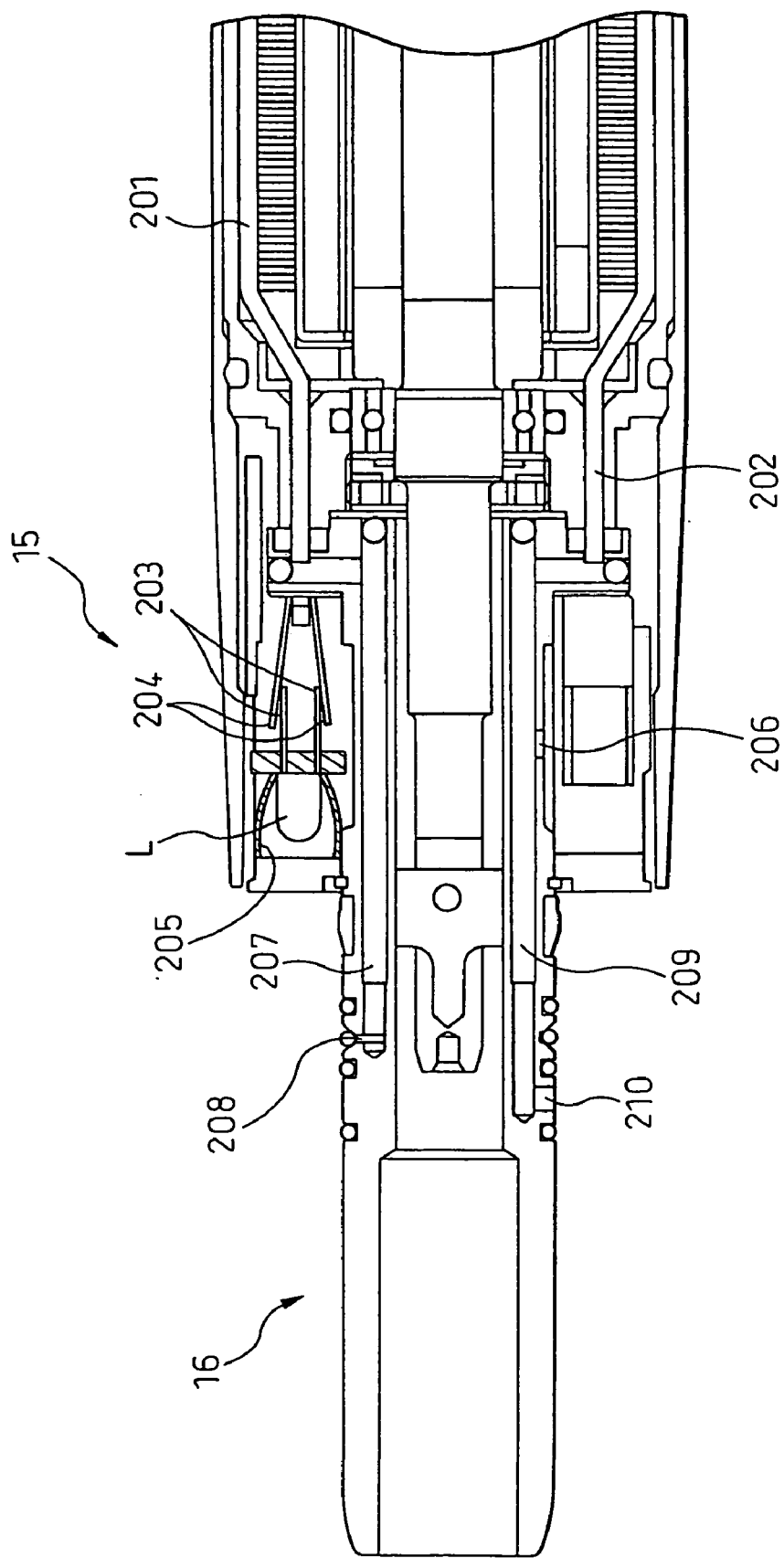
FIG. 15 is a diagram for explaining the details of the light source section of the light radiating unit in the 11th specific example.

FIG. 15 shows a cross-sectional view of an essential portion of the joint 15, including the base 16, for explaining how the light-emitting device is mounted in the 10th and 11th specific examples. The center portion of the base 16 protrudes from the forward end thereof. The light-emitting device L is mounted in a portion of the area surrounding the protruding center portion. The terminals 204 of the light-emitting device L are connected to electrical terminals 203 so that power is supplied to it. Air conduits 202 and 209 for carrying supply air and cooling air and water conduits 201 and 207 for carrying water are formed inside the base 16, and air and water are supplied through openings 208 and 210 into the handpiece body not shown. The air conduit 209 is provided with an air hole 206 so that the air supplied through the air conduit 209 flows through the area surrounding the light-emitting device L which is thus cooled. The light-emitting device L is provided with a reflective member 205. The light-emitting device L is disposed facing the light entrance face G2 of the light guide member G through which the light emitted from the light-emitting device L is transmitted to the forward end of the handpiece body not shown.

Figure 16A:
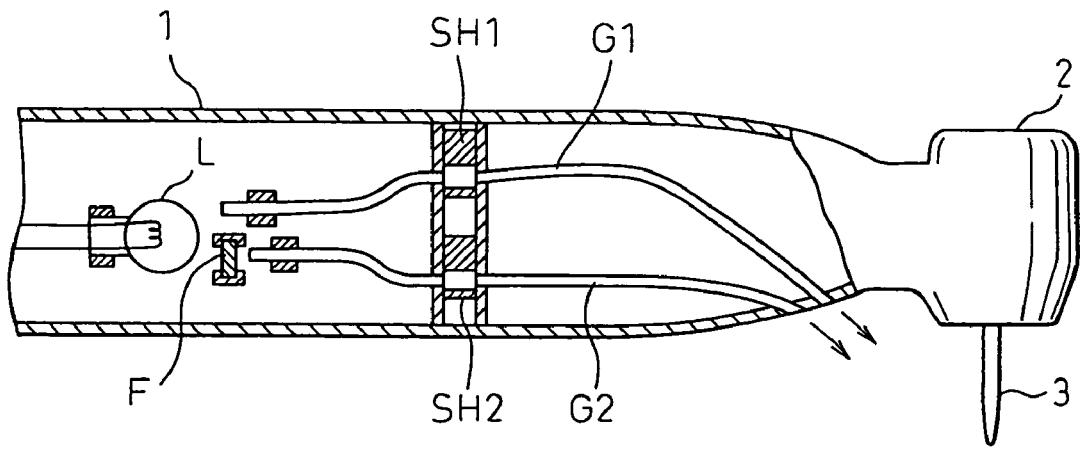
FIGS. 16A and 16B are diagrams for explaining a 12th specific example, and a modified example thereof, which concerns the mounting of the light radiating unit at the forward end of the handpiece according to the first embodiment.
Figure 16B:
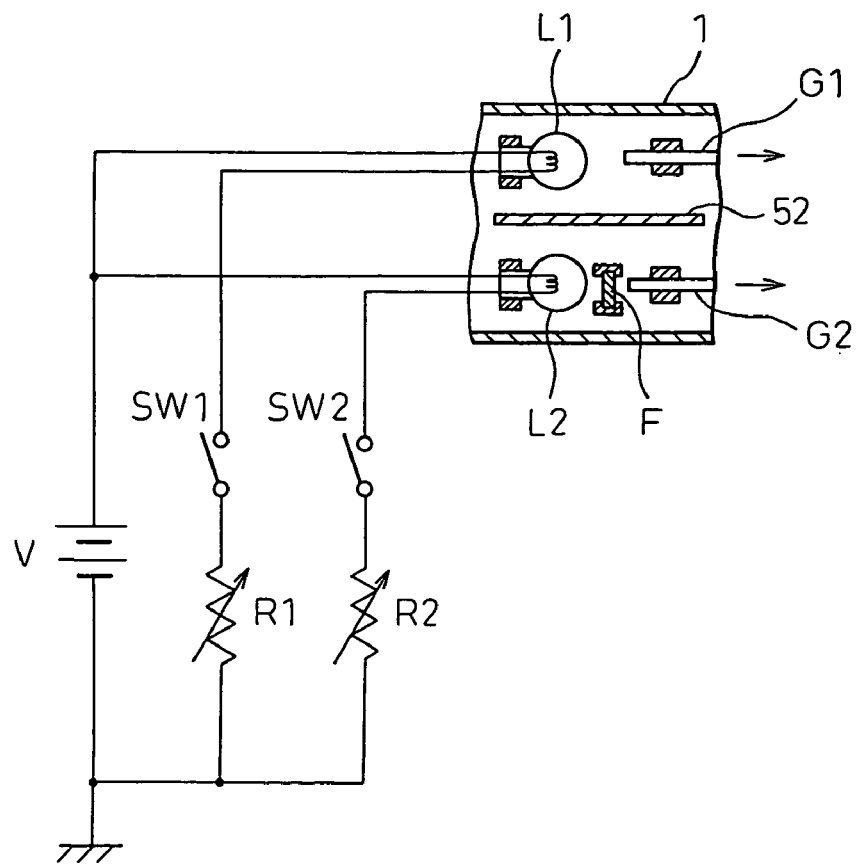

The 10th and 11th specific examples of the second embodiment described above relate to the case where a light source such as an LED or a semiconductor laser is used as the light-emitting device L; next, FIGS. 16A and 16B show a 12th specific example in which a lamp light source is employed as the light-emitting device L. The lamp light source can be selected from among a halogen lamp, a xenon lamp, a sodium lamp, a metal halide lamp, a mercury lamp, a blacklight lamp, etc. When radiating illumination light, the light as it is emitted from the lamp light source is directly guided through a light guide member, and when radiating light having a specific wavelength, the light is guided through the light guide member by passing through an optical filter.

In FIG. 16A, internal components other than the light radiating means are omitted for clarity. The figure shows a view, with a portion of the handpiece body 1 broken away, of the construction in which the light radiating means comprising a lamp light source is built into a micromotor handpiece similar to the one shown in the 10th specific example. The lamp light source L is mounted within the handpiece body 1, and the light emitted from the lamp light source L is guided through light guide members G1 and G2 up to a portion near the handpiece head 2 and is directed toward the tip of the treatment tool 3.

A light shutter member SH1 for blocking the light being guided through the light guide member G1 and a light shutter member SH2 for blocking the light being guided through the light guide member G2 are installed at intermediate positions along the respective light guide members G1 and G2 in such a manner as to be movable in a direction perpendicular to the direction in which the light is guided. Each light guide member is installed with its light entrance face facing the lamp light source L, and an optical filer for allowing a selected wavelength to pass through is provided on either one or both of the light guide members G1 and G2. In the example of FIG. 16A, the optical filter F is provided on the light guide member G2. When providing optical filters F on both of the light guide members, the optical filters F may be chosen to transmit different wavelengths.

By suitably moving the light shutter members SH1 and SH2, only the white illumination light passed through the light guide member G1 or only the excitation light passed through the light guide member G2 can be radiated, or both the illumination light and the excitation light can be radiated. The light shutter members SH1 and SH2 may be constructed so that they can be moved independently of each other or so that they move together as a unit.

FIG. 16B shows a modified example of the 12th specific example shown in FIG. 16A; in this modified example, two lamp light sources L1 and L2 are used, with provisions made to be able to adjust the amount of illumination light and the amount of excitation light individually. This modified example requires the use of two lamp light sources in order to adjust the respective light amounts independently of each other. In the modified example of FIG. 16B, the illumination light from the lamp light source L1 enters the light guide member G1, while the excitation light from the lamp light source L2 enters the light guide member G2. A shield plate 52 is provided between the lamp light sources L1 and L2 to prevent the light from one light source from interfering with the other.

Power for operating the lamp light sources L1 and L2 is supplied from a power supply V, and the lamp light source L1 is turned on and off using a switch SW1, while the lamp light source L2 is turned on and off using a switch SW2. A variable resistor R1 is inserted between the switch SW1 and ground, and likewise, a variable resistor R2 is inserted between the switch SW2 and ground; by adjusting these variable resistors R1 and R2, the light emission levels of the respective lamp light sources L1 and L2 are adjusted independently of each other. This light output level adjusting method can also be applied to other specific examples described above when the light source of the light radiating means is a lamp light source and when the lamp light source is mounted inside the handpiece body.

Embodiment 3

Next, referring to FIGS. 17 to 21, the third embodiment will be described which concerns the case where the light radiating means according to the present mode is applied to a scaler handpiece. FIGS. 17A and 17B show the basic structure of the light radiating means according to the present mode as applied to the scaler handpiece; in particular, the portion centering around the forward end of the handpiece body 1 is shown in FIGS. 17A and 17B.

In FIG. 17A, the light-emitting device L is mounted exposed in one specific position near the portion of the forward end 18 to which the treatment tool (diagnostic tool) 3 is attached. The mounting position is slightly tilted, the tilt angle being chosen according to the shape of the treatment tool 3, i.e., the scaler, so that the optical axis of the light-emitting device, when mounted, is directed toward the tip of the scaler, as shown by dashed lines. Here, the light-emitting device L may be covered with an optically transmissive protective cover or the like.

For the mounting of the light-emitting device L, the same mounting method and the same method of selecting the number of light-emitting devices to be mounted, etc. as those employed in the first and second specific examples of the previously described first embodiment can be directly applied here. However, it is to be noted that since the scaler treatment tool is usually mounted in place by screwing, the orientation of the scaler when mounted is not always the same.

Accordingly, if the light-emitting device L is fixedly mounted in one specific position as shown in FIG. 17A, the tip of the scaler when mounted may point in a direction different than that shown in the figure; if this happens, the light emitted from the light-emitting device L illuminates an area other than the scaler tip. This causes a problem when observing tartar, etc. during treatment.

To avoid this problem, a plurality of light-emitting devices L may be arranged around the periphery of the forward end of the handpiece body 1, as shown in FIG. 17B. This arrangement offers the additional advantage that, when the output of the single light-emitting device L is not sufficient, the necessary output can be obtained by arranging the necessary number of light-emitting devices; furthermore, the plurality of light-emitting devices L can be made to emit different kinds of light. In FIG. 17B, a light guide adapter 19, to be described in detail later, is attached to the forward end 18 of the handpiece body 1 so that the light is radiated through a light exit portion 20 of the forward end of the adapter. The light guide adapter 19 is formed, for example, by molding an optically transmissive, heat resistant synthetic resin, but in some cases, a fiber optic bundle can be used.

FIGS. 18A and 18B show a 13th specific example concerning the construction shown in FIG. 17B. In the 13th specific example, the same mounting method and the same method of selecting the number and the kinds of light-emitting devices to be mounted, etc. as those employed in the fourth specific example of the previously described first embodiment shown in FIG. 5 are directly applied for the light-emitting devices; that is, the plurality of light-emitting devices L are mounted in a groove 21 formed near the mounting portion of the treatment tool 3 at the forward end 18 of the handpiece body 1, and the inside surface of the groove 21 is coated with a reflective material 5.

In the 13th specific example shown in FIGS. 18A and 18B, the plurality of light-emitting devices L are mounted in the groove 21, or in a plurality of recessed portions, formed at the forward end 18, but instead, the plurality of light-emitting devices L may be mounted on an annular wiring substrate, as in the sixth specific example of the first embodiment.

Figure 19:
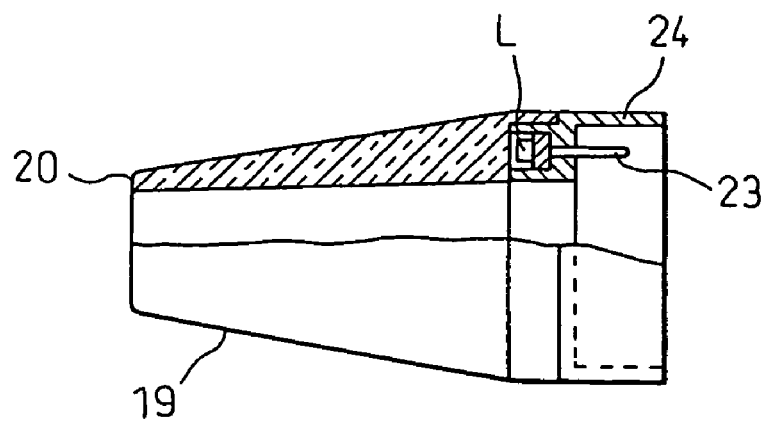
FIG. 19 is a diagram for explaining a 14th specific example relating to the mounting of the light radiating unit at the forward end of the handpiece according to the third embodiment.

Next, FIG. 19 is a diagram for explaining a 14th specific example, in which the light radiating means is constructed so that it can be detachably mounted by using the light guide adapter 19 shown in FIG. 19. Here, the light radiating means is not directly mounted on the forward end 18 of the handpiece body 1, but a detachable structure such as shown in the sixth specific example of the previously described first embodiment is employed, and a unit is constructed that has an annular head detachable member 24 engageable with the tip of the forward end 18.

The connecting terminals 23 of the plurality of light-emitting devices L are integrally molded in the head detachable member 24. The light guide adapter 19 is fixedly fastened to it in such a manner as to shroud the light-emitting devices L. The light guide adapter 19 is generally cylindrical in shape with a hollow interior space through which the leg of the scaler is inserted. The light emitted from each light-emitting device L is guided through the light guide adapter 19 to the forward end 20 thereof.

The thus constructed unit is attached to the handpiece body 1 by being fitted onto the forward end 18; at this time, the connecting terminals 23 are inserted into the sockets formed in the forward end 18 so that power can be supplied to the light-emitting devices L. In this unit, the light-emitting devices L are hermetically sealed within the light guide adapter 19 and protected against the outside air, while also preventing the infiltration of vapor and heat; in this way, since the light-emitting devices L are fully protected, autoclaving can be performed, for example, while leaving the unit attached to the handpiece body.

The light guide adapter in the 14th specific example shown in FIG. 19 has an elongated protruding shape, but the length of the adapter can be chosen as needed; furthermore, the light guide adapter may be formed in a lens-like structure. This light guide adapter can also be applied to the sixth specific example of the first embodiment.

Figure 20A:
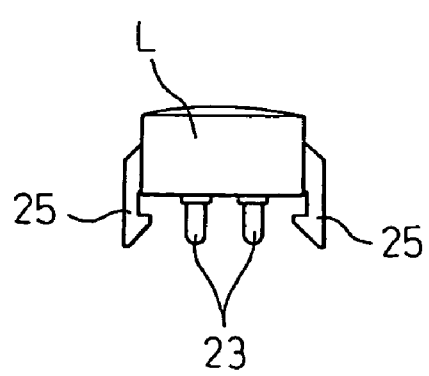
FIGS. 20A and 20B are diagrams for explaining a 15th specific example relating to the mounting of the light radiating unit at the forward end of the handpiece according to the third embodiment.
Figure 20B:
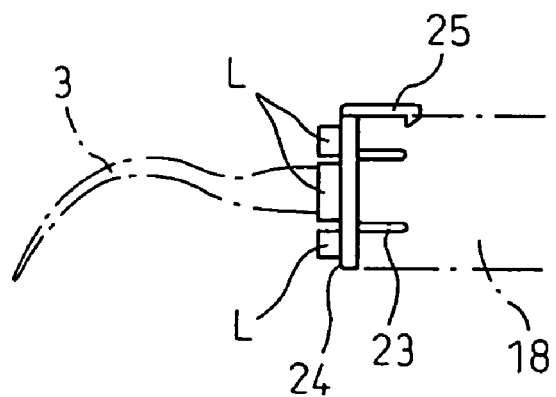

Next, FIGS. 20A and 20B show a 15th specific example in which the light-emitting devices L as the light radiating means can be detachably mounted on the handpiece body. In the above-described 14th specific example, the unit, when mounted, is held in place primarily by locking the connecting terminals into the sockets, but in the 15th specific example, an engaging member having a hooked end is used to hold the unit in place.

In the case of FIG. 20A, the module of each individual light-emitting device L is provided with two engaging members 25 having hooked ends, and the connecting terminals 23 are installed in such a manner as to protrude from the base of the module. With these engaging members, the light-emitting device module can be mounted in a desired position. On the other hand, in the case of FIG. 20B, the light-emitting devices L are arranged into a unit to form a head detachable member 24, and this head detachable member 24 is provided with an engaging member 25 having a hooked end by means of which the unit is mounted onto the forward end 18 of the handpiece body.

Figure 21:
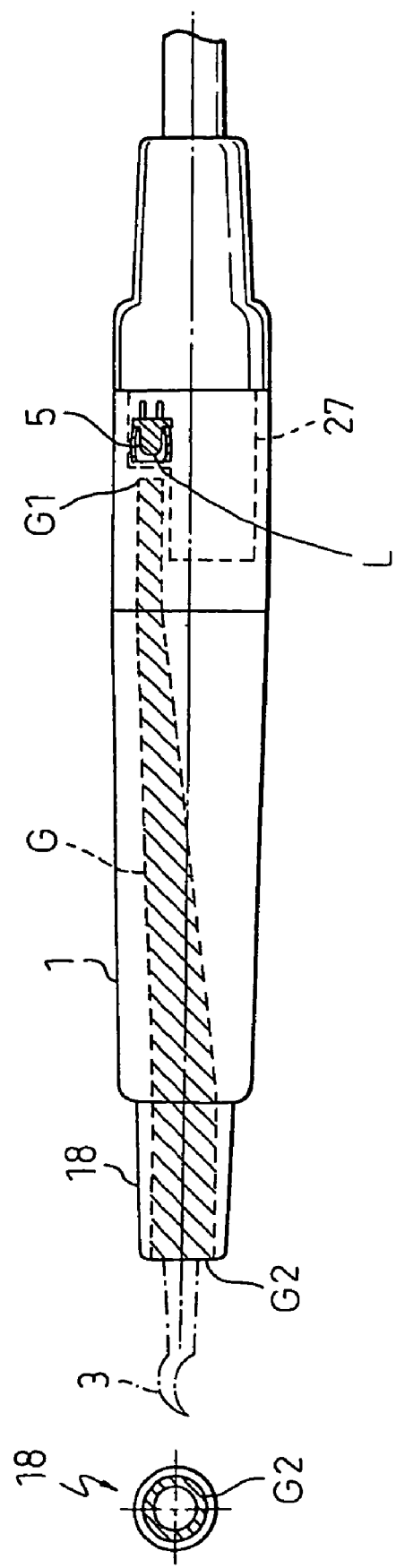
FIG. 21 is a diagram for explaining a 16th specific example relating to the mounting of the light radiating unit at the forward end of the handpiece according to the third embodiment.

The 13th to 15th specific examples according to the third embodiment so far described primarily concern the case where the plurality of light-emitting devices are mounted directly on the forward end of the scaler handpiece so that the light from each light-emitting device is directed toward the tip of the scaler; by contrast, FIG. 21 shows a 16th specific example in which the light-emitting device is built into the handpiece body and the light emitted from the light-emitting device is guided to the forward end of the handpiece.

In the 16th specific example, the light radiating means shown in the 11th specific example of the previously described second embodiment can be directly employed. As in the 11th specific example, the light-emitting device L is mounted on a side portion of the base 27 of the scaler handpiece, and the light guide member G is installed with its light entrance face G1 facing the light-emitting device L. The light emitted from the light-emitting device L enters the light guide member G through its light entrance face G1 and is guided up to the light exit face G2, and the light emerging from the light exit face G2 illuminates the area forward of the scaler 3. The light exit face G2 is located near the mounting portion of the treatment tool 3.

However, if the light radiating means shown in the 11th specific example is directly employed in the 16th specific example, the structure corresponds to the structure shown in FIG. 17A in which the light is radiated from one specific position. Therefore, in the 16th specific example shown in FIG. 21, in order that the light can always be directed toward the tip of the scaler, regardless of the mounting orientation of the scaler 3, as described with reference to FIG. 17B, the light guide member G is formed in a cylindrical shape so that its light exit face G2 is annular in shape when viewed from the front of the forward end portion 18. By constructing the light radiating means in this way, the light can be radiated over a wide range so as not to form a shadow forwardly of the scaler tip, regardless of the mounting orientation of the scaler.

Embodiment 4

Figure 22:
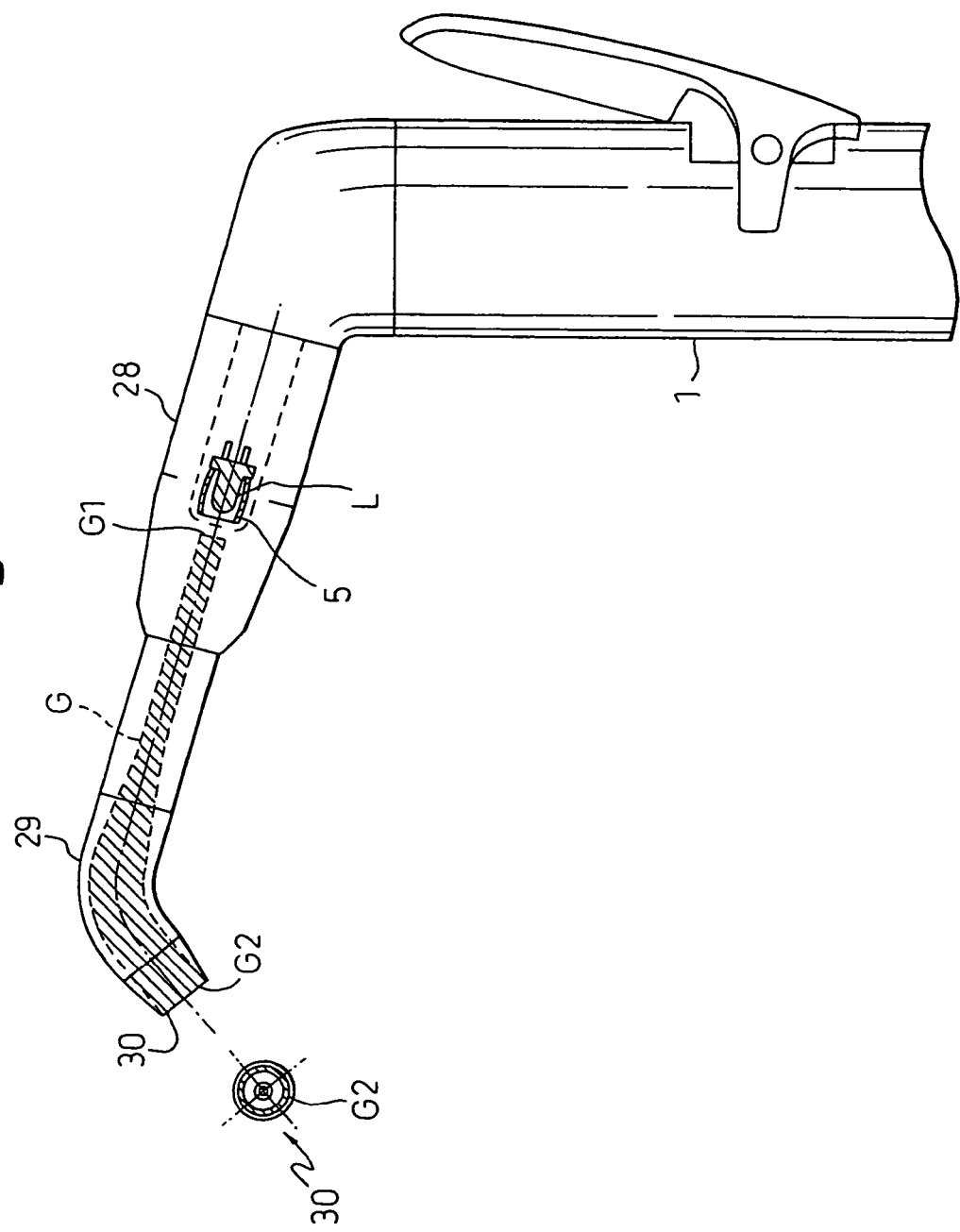
FIG. 22 is a diagram for explaining a 17th specific example relating to the mounting of the light radiating unit according to a fourth embodiment in which the present invention is applied to a three-way syringe.

The fourth embodiment concerns the case where the light radiating means according to the present mode is applied to a three-way syringe. In the 17th specific example shown in FIG. 22, the three-way syringe is equipped with a light-emitting device L which is built into the syringe body 28, and the light emitted from the light-emitting device L is guided through a light guide member G up to a forward end (diagnostic/treatment tool) 30 through which to spray atomized water, and is radiated in the same direction as the spraying direction. The light exit face G2 of the light guide member G is formed in an annular shape in such a manner as to encircle the air and water spray hole in the center, as shown in the front view of the forward end in FIG. 22. The light-emitting device L is provided with a reflective member 5.

The method of mounting the light-emitting device L of the light radiating means and the method of selecting the kind of the light-emitting device L in the 17th specific example are the same as those employed in the eighth specific example of the previously described first embodiment, and therefore the description will not be repeated here.

Figure 23:
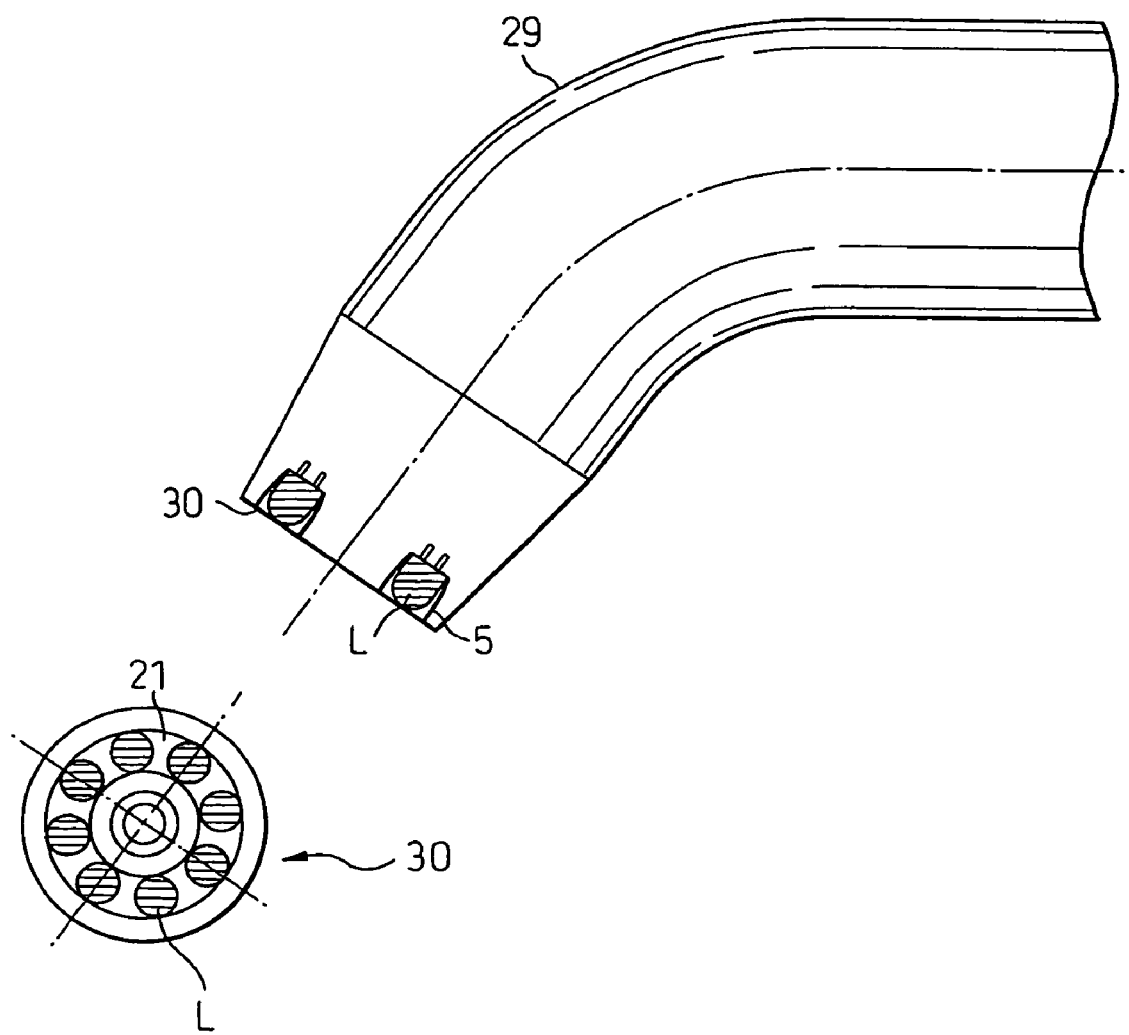
FIG. 23 is a diagram for explaining an 18th specific example relating to the mounting of the light radiating unit at the forward end of the handpiece according to the fourth embodiment.

Next, FIG. 23 shows an 18th specific example which is an example of a three-way syringe in which the light guide member employed in the 17th specific example is eliminated. A plurality of light-emitting devices L are arranged inside a groove 21 formed in the forward end 30. The method of mounting the light-emitting devices L in the three-way syringe shown in FIG. 23 is the same as that employed in the 13th specific example of the previously described third embodiment shown in FIG. 18B. The inner wall surfaces of the groove 21 are coated with a reflective material 5. Further, the opening of the groove 21 may be covered with a transparent protective member.

Instead of mounting the plurality of light-emitting devices L inside the groove formed in the forward end 30, the plurality of light-emitting devices L may be mounted on an annular wiring substrate, as shown in the sixth and seventh specific examples of the first embodiment.

Embodiment 5

Figure 24:
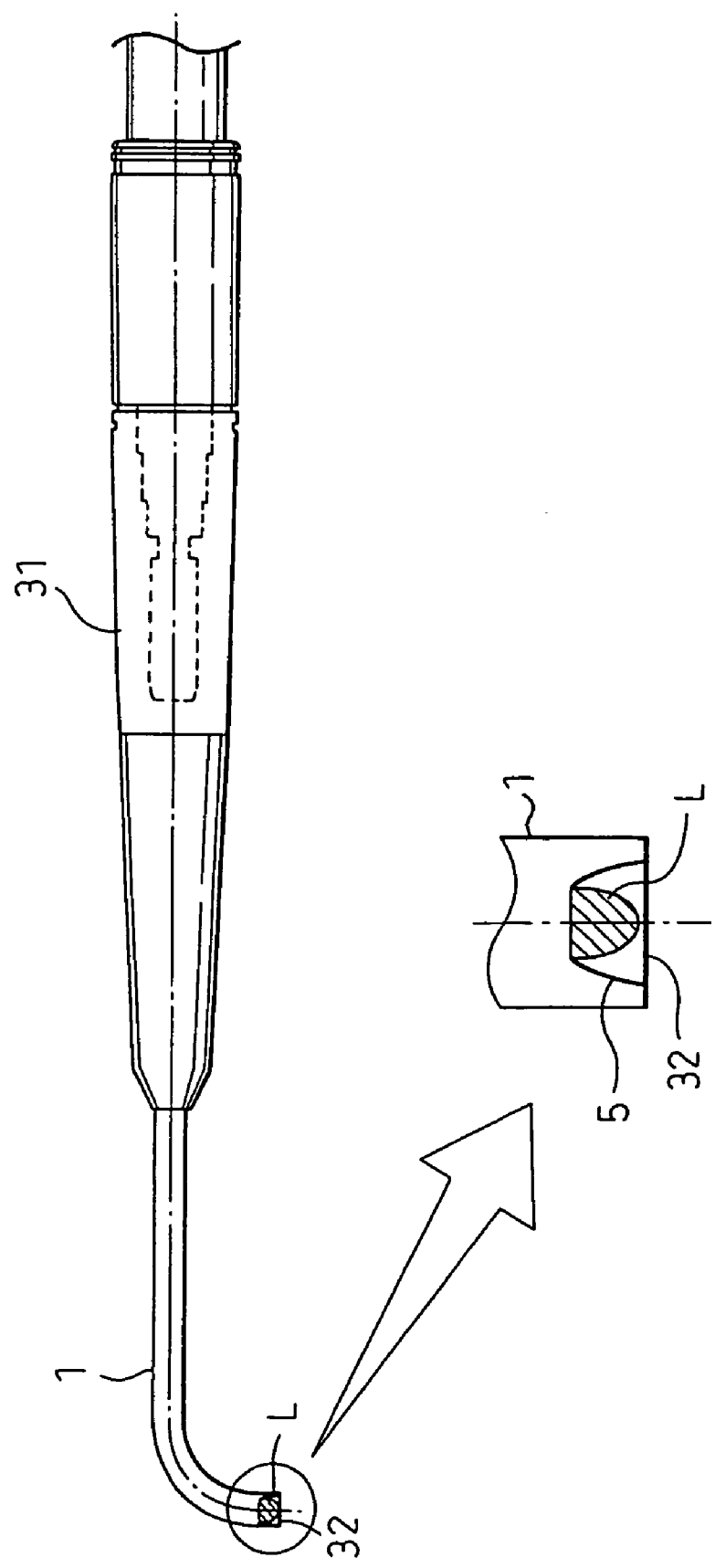
FIG. 24 is a diagram for explaining a 19th specific example relating to the mounting of the light radiating unit according to a fifth embodiment in which the present invention is applied to a light probe.

The fifth embodiment concerns the case where the light radiating means according to the present mode is applied to a light probe, and FIG. 24 shows a 19th specific example in which the light-emitting device L is mounted at a forward end 32 which is the light exit end of the light probe body 31. The method of mounting the light-emitting device L at the forward end here is the same as that employed in the first specific example of the previously described first embodiment, that is, the light-emitting device L is mounted in a recessed portion formed in the forward end (diagnostic/treatment tool) 32. In use, the light probe body 1 is attached to a joint 31. The method of supplying power to the light-emitting device L is the same as that employed in other specific examples.

Figure 25:
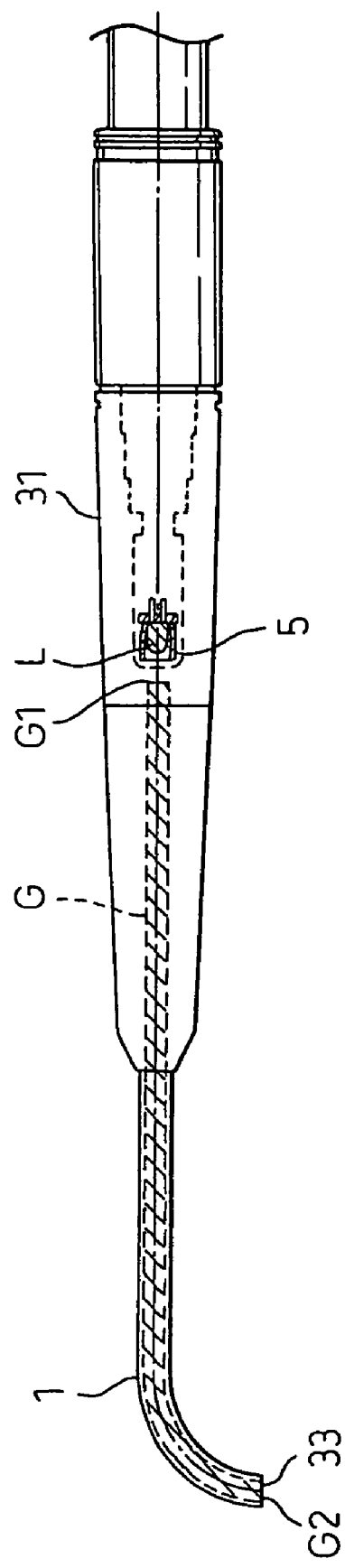
FIG. 25 is a diagram for explaining a 20th specific example relating to the mounting of the light radiating unit at the forward end of the handpiece according to the fifth embodiment.

FIG. 25 shows a 20th specific example in which the light-emitting device L is mounted inside the light probe body 31, and the light emitted from the light-emitting device L is guided through a light guide member G and radiated from the forward end (diagnostic/treatment tool) 33 of the light probe body 31. The light-emitting device L is provided with a reflective member 5. The light radiating means employed in the 20th specific example is the same as that employed in the eighth specific example of the previously described first embodiment, that is, the light enters through the light entrance face G1 disposed facing the light-emitting device L and is guided to the light exit face G2 at the forward end 33, and the light emerging from the light exit face G2 is radiated forward.

In the 20th specific example also, as in the ninth specific example of the first embodiment, an imaging device such as a CCD may be built into the light probe body 31 along with a separately installed light guide member so that the fluorescence reflected from a target area illuminated with the excitation light radiated from the light exit face G2 can be observed as an image.

Embodiment 6

Figure 26:
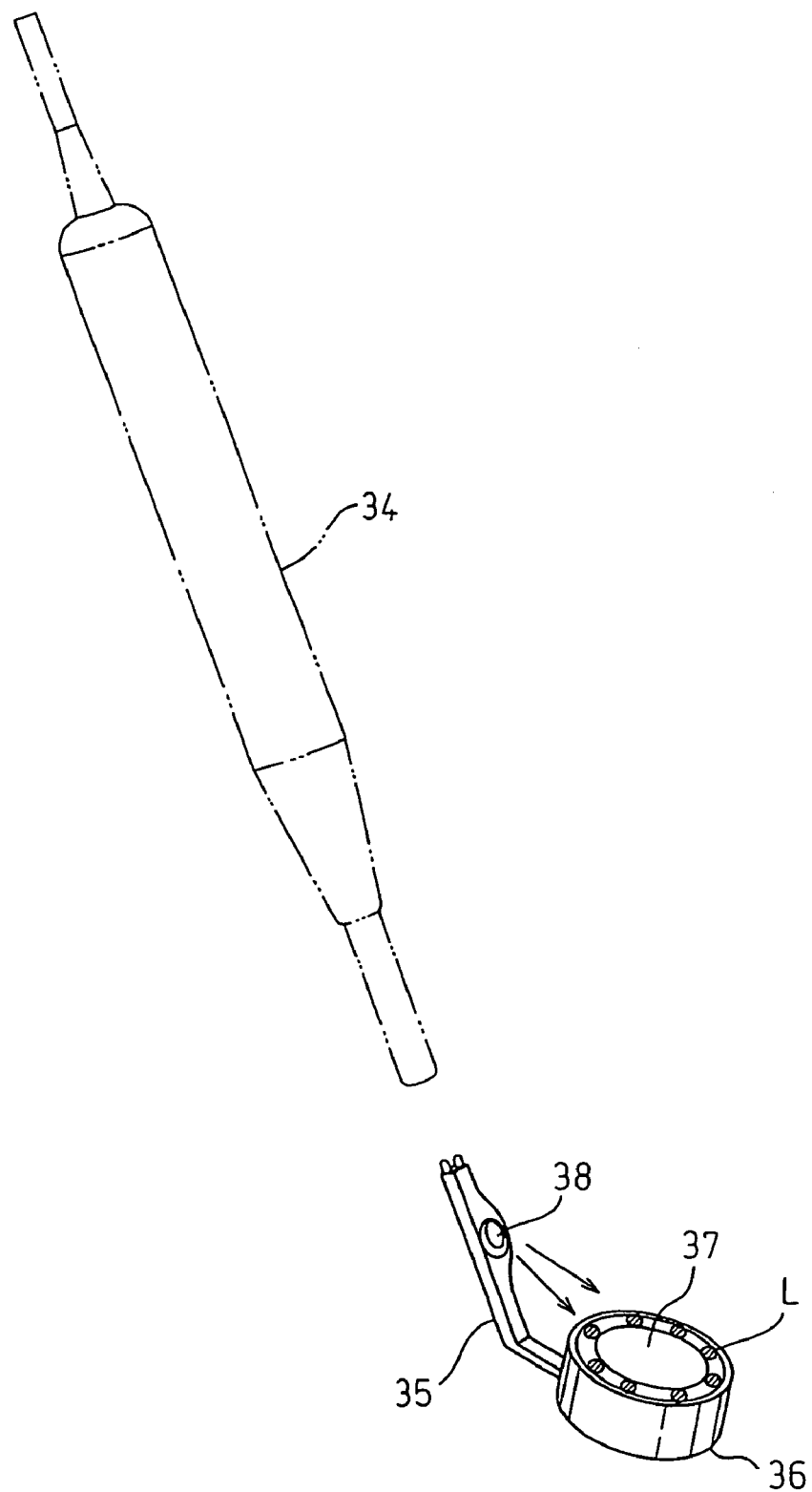
FIG. 26 is a diagram for explaining the structure relating to the mounting of the light radiating unit according to a sixth embodiment in which the present invention is applied to a dental mirror.

The sixth embodiment concerns the case where the light radiating means according to the present mode is applied to a dental mirror with lighting, one specific example of which is shown in FIG. 26.

The dental mirror has a forward end portion 35 which is detachable from an instrument body 34, and a mirror holding member 36 is attached to the opposite end of the forward end portion 35. An illuminating means 38 is mounted in the shaft of the forward end portion 35. The illuminating means 38 radiates illumination light toward the mirror (diagnostic tool/treatment) 37, as shown by arrows. A plurality of light-emitting devices L are arranged along the periphery of the mirror holding member 36 in such a manner as to completely or partially encircle the mirror. The same method of mounting and arranging the light-emitting devices L as employed for the construction of the light radiating means in the fourth specific example of the previously described first embodiment can be employed here.

A filter formed in the shape of a cap can be detachably mounted on the surface of the mirror 37. This cap-like filter is provided so that only a specific wavelength which differs according to the purpose is reflected from the mirror 37. The specific wavelength here is, for example, a wavelength in the near ultraviolet region of 405±50 nm, the blue region of 470±30 nm, the red region of 700±100 nm, the infrared region, or the near infrared region, but is not limited to any one of these wavelengths.

The cap-like filter is mounted in such a manner as to be superimposed on the surface of the mirror, and the portion facing each light-emitting device L is a transparent glass or space so that the light from the light-emitting device L is directly radiated onto the lesion. The illuminating means 38 may be omitted. Further, the dental mirror may be constructed as a battery-operated cordless instrument by building a battery into the instrument body 34 or the mirror holding member 36.

According to the thus constructed dental mirror with lighting, when an area that appears to be a lesioned area is found while observing the oral cavity with the illumination light, the area can be easily checked to determine whether it is a lesioned area or not by projecting the excitation light from the light-emitting device L onto that area and by observing its reflected light with eyeglasses or the like having an optical filtering function. If the optical filter is mounted on the mirror surface, the lesion can be observed with the naked eye. Further, if a plurality of optical filters for reflecting only the above-mentioned different specific wavelengths are prepared and constructed so as to be detachable with respect to the mirror surface, then different kinds of lesions can be observed by changing the optical filters. Alternatively, the optical filter may be formed integrally with the mirror, for example, by applying a coating on the mirror surface, and the mirror with the optical filter may be constructed so as to be detachable with respect to the mirror holding member 36.

Embodiment 7

Figure 27A:
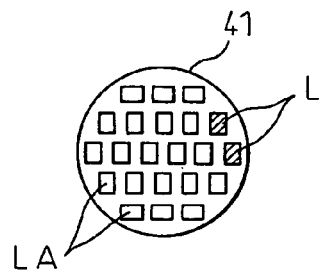
FIGS. 27A and 27B are diagrams for explaining the structure relating to the mounting of the light radiating unit according to a seventh embodiment in which the present invention is applied to a dental photo-polymerization device.
Figure 27B:
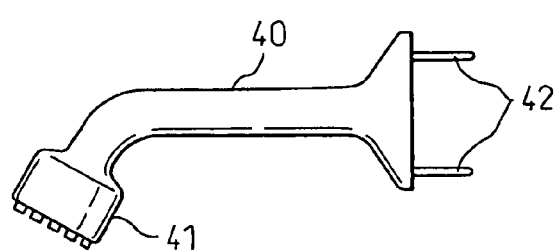

The seventh embodiment concerns the case where the light radiating means according to the present mode is applied to a dental photo-polymerization device, the forward end of which is shown in FIGS. 27A and 27B. The photo-polymerization device comprises a photo-polymerization device body 40 and a photo-polymerization device head (diagnostic/treatment tool) 41, and a plurality of light-emitting devices LA, each constructed from a light-emitting diode for radiating blue light that aids polymerization, and light-emitting devices L for radiating excitation light are mounted on the front face of the photo-polymerization device head 41. Connecting terminals 42 for supplying power to the light-emitting devices are provided in such a manner as to protrude from the photo-polymerization device body 40. With the connecting terminals 42 inserted in the sockets formed in the handpiece body (not shown), the photo-polymerization device body 40 is held fixed on the handpiece body, and power is supplied to the light-emitting devices. In the illustrated example, the light-emitting devices are operated from power supplied via the connecting terminals 42 inserted in the sockets formed in the handpiece body (not shown), but a battery for operating the photo-polymerization light source and the light-emitting devices may be built into the handpiece body, or the photo-polymerization device body 40 may be constructed integrally with the handpiece body and not separable from it.

The illustrated construction in which the photo-polymerization device is detachable from the handpiece body has the advantage that the handpiece body can be used as the photo-polymerization device, as well as for other treatment purposes, and the apparatus installation cost can be reduced correspondingly. When using it as the photo-polymerization device, since other treatment tools are not used, the photo-polymerization device body 40 can be formed in a curved shape suitable for the purpose; furthermore, since there is no need to provide a hole passing through the body along the longitudinal direction thereof, the body can be made in an elongated structure containing only power supply lead lines to the light-emitting devices 3.

Moreover, since the light-emitting devices for radiating the excitation light can be mounted in the same manner as the polymerization light emitting devices, not only does the construction becomes simple, but the excitation light can also be radiated simultaneously with the polymerization light; accordingly, while performing the polymerization treatment, the lesion can be easily detected by observing the reflected light with eyeglasses or the like having an optical filtering function.

In the above description, the diagnostic/treatment instrument refers to an air turbine handpiece, a micromotor handpiece, a scaler, a three-way syringe, a vacuum syringe, a laser handpiece, a dental mirror, or a dental photo-polymerization device. The handpiece refers to that portion of the diagnostic/treatment instrument which the clinician holds in his hand when performing diagnosis or treatment. In the embodiments shown in FIGS. 22, 23, 24, 25, 26, 27, and 62, treatment tools (diagnostic tools) such as drilling tools are not attached, but since the diagnostic/treatment instrument is equipped with lighting for diagnosis/treatment and a fluid spray hole, such diagnostic/treatment tools are also included as one kind of diagnostic/treatment tool.

Embodiment 8

An eighth embodiment concerns the case where the light radiating means according to the present mode is applied to a dental laser treatment instrument. A 21st specific example is shown in FIGS. 29A and 29B. Conventionally, the dental laser treatment instrument has been used in intraoral treatment for such purposes as evaporation and incision of living tissue, coagulation and hemostasis, and warming and pain easing, and even for tooth drilling, and the laser light used for such purposes is generated by a laser light source provided in a drive control apparatus S shown in FIG. 62, and is guided through a light guide member, such as an optical fiber passed through a tube TU, up to the forward end (diagnostic/treatment tool) of the handpiece HP.

A semiconductor laser, a $CO_2$ laser, an Er:YAG laser, an Nd:YAG laser, an Ho:YAG laser, or the like is used as the laser light source. When the intensity of the laser light is high, and high output power is needed, the laser light source has to be installed inside the drive control apparatus S as shown, but when the laser intensity is relatively small, the laser light source can be mounted within the handpiece HP, in which case the light generated by the laser light source can be guided through a light guide member to the forward end of the handpiece HP.

Figure 28A:
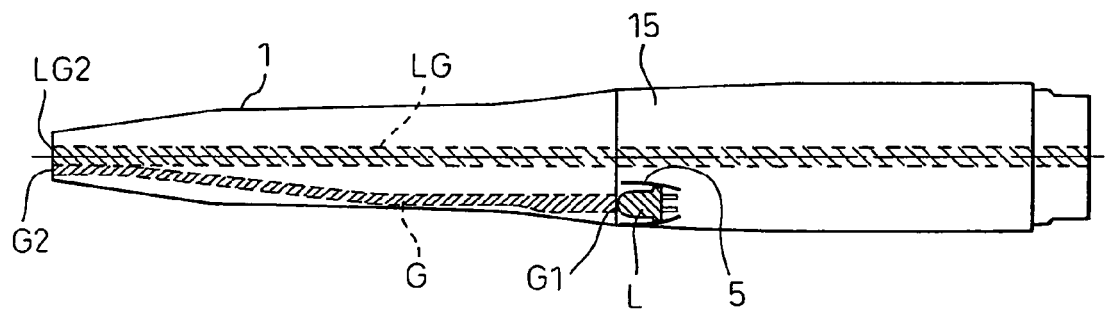
FIGS. 28A and 28B are diagrams for explaining a 21st specific example relating to the mounting of the light radiating unit according to an eighth embodiment in which the present invention is applied to a dental laser treatment instrument.

When the light guide member LG for guiding the treatment laser light is installed passing approximately through the center of the handpiece in the dental laser treatment instrument as shown in FIG. 28A, the light radiating means according to the present mode can be incorporated in the same manner as the light radiating means in the 12th specific example of the second embodiment shown in FIG. 15.

In the example shown in FIG. 28A, the light-emitting device L is mounted on the joint 15 at a position that does not interfere with the position through which the light guide member LG passes. Then, the light guide member G for the light radiating means, with its light entrance face G1 disposed facing the light-emitting device L, is installed in such a manner as to extend in parallel to the light guide member LG, and the other end of the light guide member G, i.e., the light exit face G2, is exposed at the forward end of the handpiece.

Since the dental laser treatment instrument shown in FIG. 28A does not have a handpiece head, the light exit face G2 is disposed in the same plane as the light exit face LG2 of the light guide member LG at the forward end of the handpiece body 1 so that the light can be radiated substantially in parallel with the laser light.

In the case of the dental laser treatment instrument shown in FIG. 28A, the light exit face G2 is arranged in one specific position at the forward end of the handpiece body 1, but when the light guide member G is formed, for example, from a fiber optic bundle, the light exit face G2 may be arranged around the periphery of the forward end face of the handpiece body 1 so as to encircle the light exit face LG2, in a manner similar to the 16th specific example shown in FIG. 21. By arranging the light exit face G2 in such an encircling shape, spot-like illumination can be converted to wide spreading illumination.

Figure 28B:
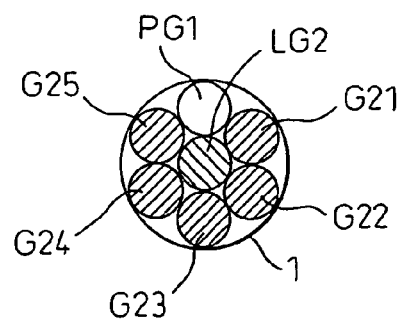

Further, in the case of the dental laser treatment instrument shown in FIG. 28A, the light radiating means is constructed to emit light at one specific wavelength, but when it is desired to emit light at a plurality of specific wavelengths, a plurality of light-emitting devices L can be arranged on the joint 15 in such a manner as to encircle the light guide member LG; in this case, a plurality of light guide members G corresponding to the respective light-emitting devices L should be installed. As shown in FIG. 28B, the light exit faces G21 to G25 of the plurality of light guide members G are arranged around the light exit face LG2 of the light guide member LG.

In the example of FIG. 28B, the condition of the lesion can be observed on the monitor by radiating light of the specific wavelength and viewing an image of the reflection of the light captured by an imaging device, so that the lesion such as caries can be diagnosed or treated while observing the condition of the lesion. Though not shown in FIG. 28A, an imaging device such as that employed in the ninth specific example of the first embodiment shown in FIG. 12 can be mounted on the joint 15. The light entrance face PG1 of the image guide member PG for guiding the reflected light to the imaging device is located at the forward end of the handpiece body 1. This imaging device may be mounted within the drive control apparatus for the dental laser treatment instrument.

Figure 54:
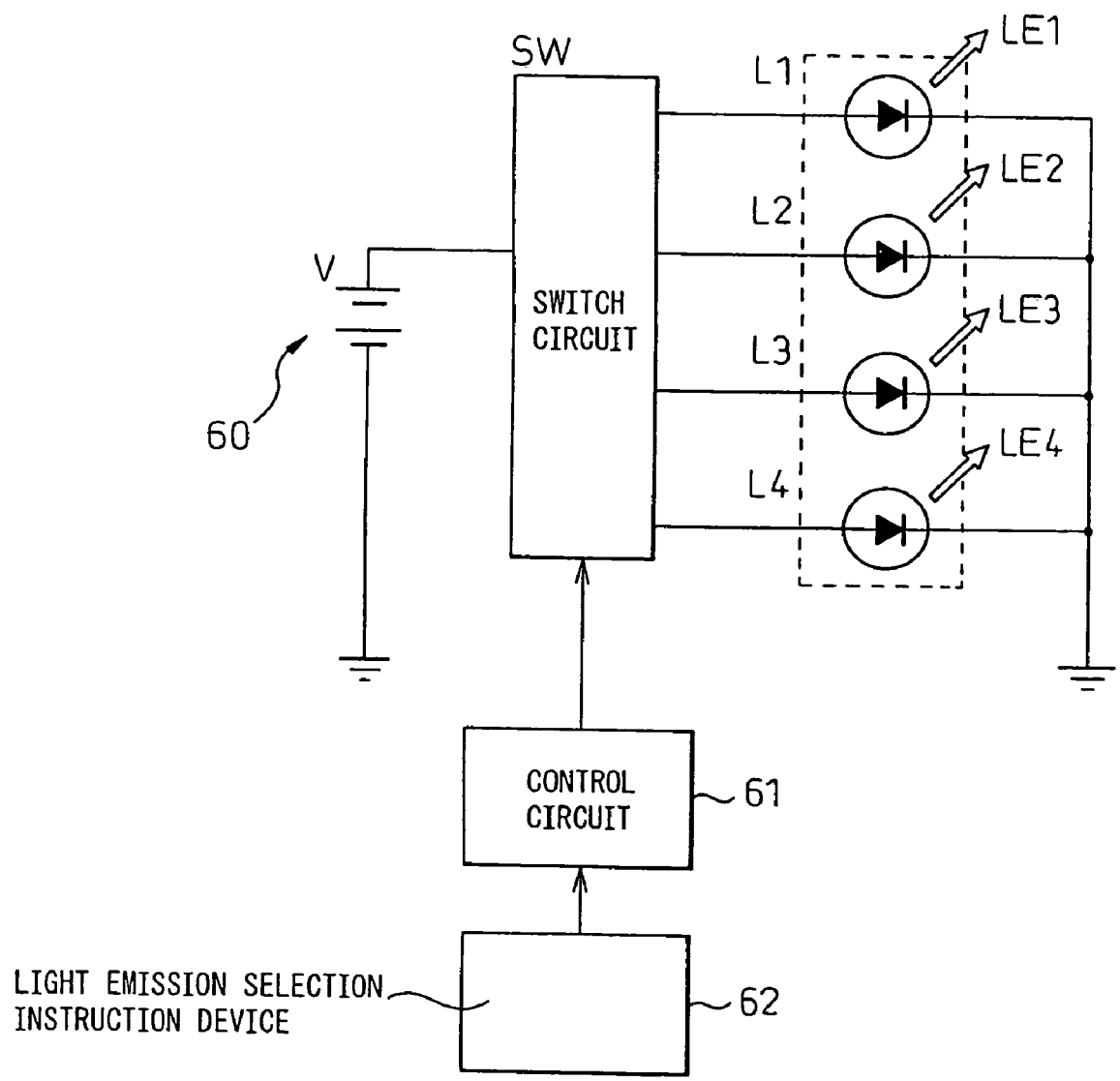
FIG. 54 is a diagram for explaining a driving circuit for controlling the on/off operation of a plurality of light-emitting devices.
Figure 55:
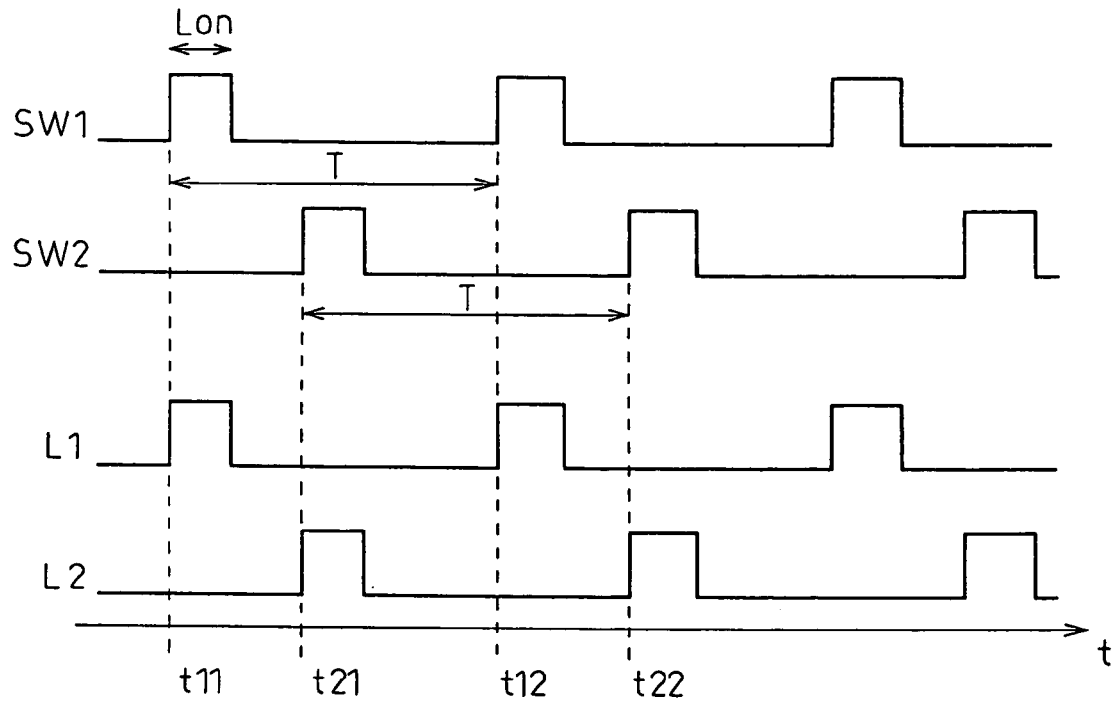
FIG. 55 is a time chart diagram for explaining how switches are controlled when turning on the light-emitting devices in a time-division fashion.

When the light radiating means is constructed to emit light at a plurality of specific wavelengths as shown in FIG. 28B, the on/off operation of each light-emitting device is controlled using the control circuit shown in FIG. 54 in a selective manner as previously described, or the light-emitting devices are turned on sequentially in a time-division fashion as shown in FIG. 55.

FIGS. 28A and 28B have shown the construction in which the light-emitting devices are mounted within the handpiece, but instead, the plurality of light-emitting devices L may be arranged exposed around the light exit face LG2 of the light guide member LG at the forward end of the handpiece body 1 of the dental laser treatment device in a manner similar to the 13th to 15th specific examples of the third embodiment and the 18th specific example of the fourth embodiment. Alternatively, the plurality of light-emitting devices L may be mounted on a detachable member which is detachable from the forward end of the handpiece body 1.

The light-emitting device L as the light source of the light radiating means may be mounted within the drive control apparatus for the dental laser treatment instrument. In that case, the light emitted from the light-emitting device L is guided through the light guide member G passed through the tube TU and reaches the forward end of the handpiece body 1, just like the treatment laser light.

In this case, if a plurality of light-emitting devices for emitting light at different specific wavelengths are mounted, the light may be guided to the forward end of the handpiece body 1 by using a single light guide member G, rather than using one light guide member G for each individual light-emitting device. The light-emitting devices may be turned on one at a time in a selective manner, or in a time-division fashion as shown in FIG. 55. Further, when turning on the plurality of light-emitting devices simultaneously, the lights from the respective light-emitting devices may be mixed together and guided through the light guide member G.

When a lamp for emitting white light is provided as the light source of the light radiating means in the drive control apparatus for the dental laser treatment instrument, an optical filter F for selecting a specific wavelength can be placed on the light entrance face G1 of the light guide member G for the lamp so that the light can be switched between the illumination light and the light of the specific wavelength. Further, provision may be made to switch between a plurality of optical filters, allowing selection between a plurality of specific wavelengths.

Usually, the laser handpiece is constructed so that a visible light beam that serves as a guide in locating the area being illuminated with the work light, i.e., the laser light, is radiated as guide light from the handpiece. The guide light propagates through the same path as the laser light, at least until the light emerges from the forward end of the laser handpiece; as a result, the light emerging from the forward end is mixed light WG containing both the work light and the guide light.

Figure 29:
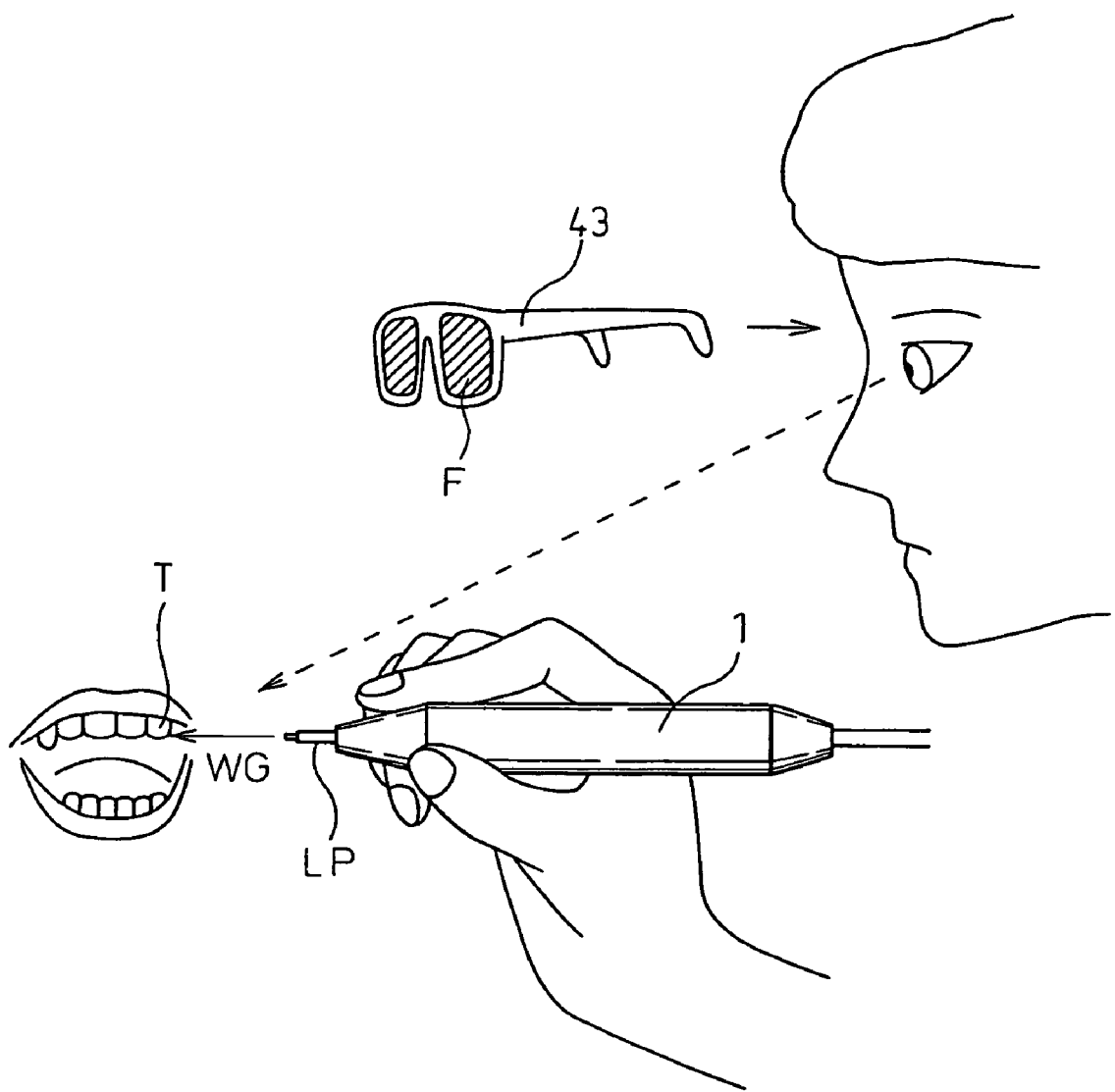
FIG. 29 is a diagram for explaining how dental treatment is performed using a laser handpiece to which the present invention is applied.

In view of this, a specific example according to the eighth embodiment will be described in which the laser handpiece capable of radiating such mixed light WG is constructed so that excitation light for distinctively detecting a lesion is radiated instead of the guide light contained in the mixed light WG. FIG. 29 shows how the laser handpiece which emits the mixed light WG containing the excitation light is used.

The mixed light WG consisting of the work light and the guide light is radiated toward a tooth T, the target area, from a laser probe (diagnostic/treatment tool) LP attached to the forward end of the laser handpiece body 1. The operator as the dentist holds the laser handpiece body 1 in his hand and performs treatment by illuminating the target area. If there is a lesion such as caries in the tooth T being illuminated, fluorescence, etc. is emitted from the tooth T when illuminated with the guide light which is also the excitation light; as a result, the operator can identify the location of the target area with the guide light contained in the mixed light WG and, at the same time, if a lesion such as caries is detected, the operator can illuminate the lesion with the work light contained in the mixed light WG while confirming the position of the lesion. The target area being illuminated may be viewed with the naked eye, but goggles 43 equipped with an optical filter F for cutting off the excitation light may be used to enhance the visibility of the fluorescence. In this way, the lesion can be observed clearly. As will be described hereinafter, in the case of a handpiece equipped with an image capturing means, the lesion may be observed using a display means such as a monitor.

Figure 30:
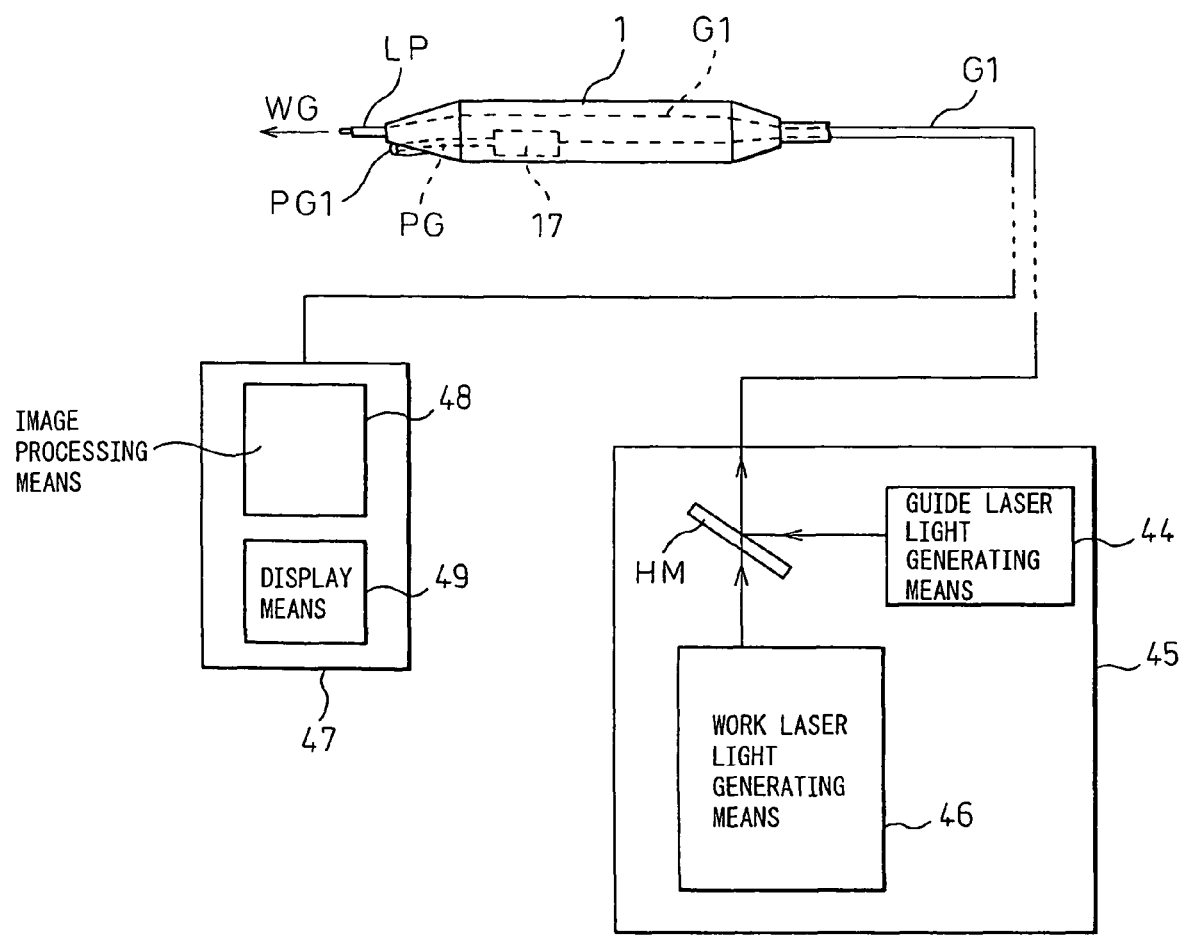
FIG. 30 is a diagram for explaining a 22nd specific example relating to the mounting of the light radiating unit according to the eighth embodiment in which the present invention is applied to the laser handpiece.

FIG. 30 shows a 22nd specific example as one example of the laser handpiece equipped with a built-in image capturing means. As shown in FIG. 30, a laser generating apparatus 45 comprises a work laser light generating means 46 and a guide laser light generating means 44, and a dichroic mirror HM is arranged within the laser generating apparatus 45 in the path of the laser light projected from the work laser light generating means 46. The guide light generated by the guide laser light generating means 44 is reflected by the dichroic mirror HM. The mixed light WG produced by mixing the work laser light with the guide light here is guided through the light guide member G1 to the laser probe LP fixed to the forward end of the laser handpiece body, and is radiated toward the target area.

Here, the excitation laser light may be generated within the guide laser light generating means 44, or the excitation laser light may be generated by a separately provided excitation laser light generating means and mixed with the work laser light at the dichroic mirror. Alternatively, rather than radiating the excitation light through the light guide member G1, a light source constructed from a light-emitting device such as an LED or LD may be mounted near the laser probe LP at the forward end of the laser handpiece body 1, and the excitation light produced by that light source may be radiated in the same direction as the work laser light being radiated from the laser probe LP.

On the other hand, an image capturing means comprising a CCD imaging device is mounted within the laser handpiece body 1. A light entrance part PG1 having an optic for receiving light reflected from the target area is mounted at the forward end of the handpiece body 1, and the reflected light incident on the light entrance part PG1 is guided through an image guide member PG to the image capturing means 17 where an image of the target area is captured. Electrical signals representing the image of the target area thus captured are transmitted to an image processing means 48 in an image processing apparatus 47 and, after image processing is done, the image of the target area is displayed on the monitor screen of a display means 49.

Figure 31:
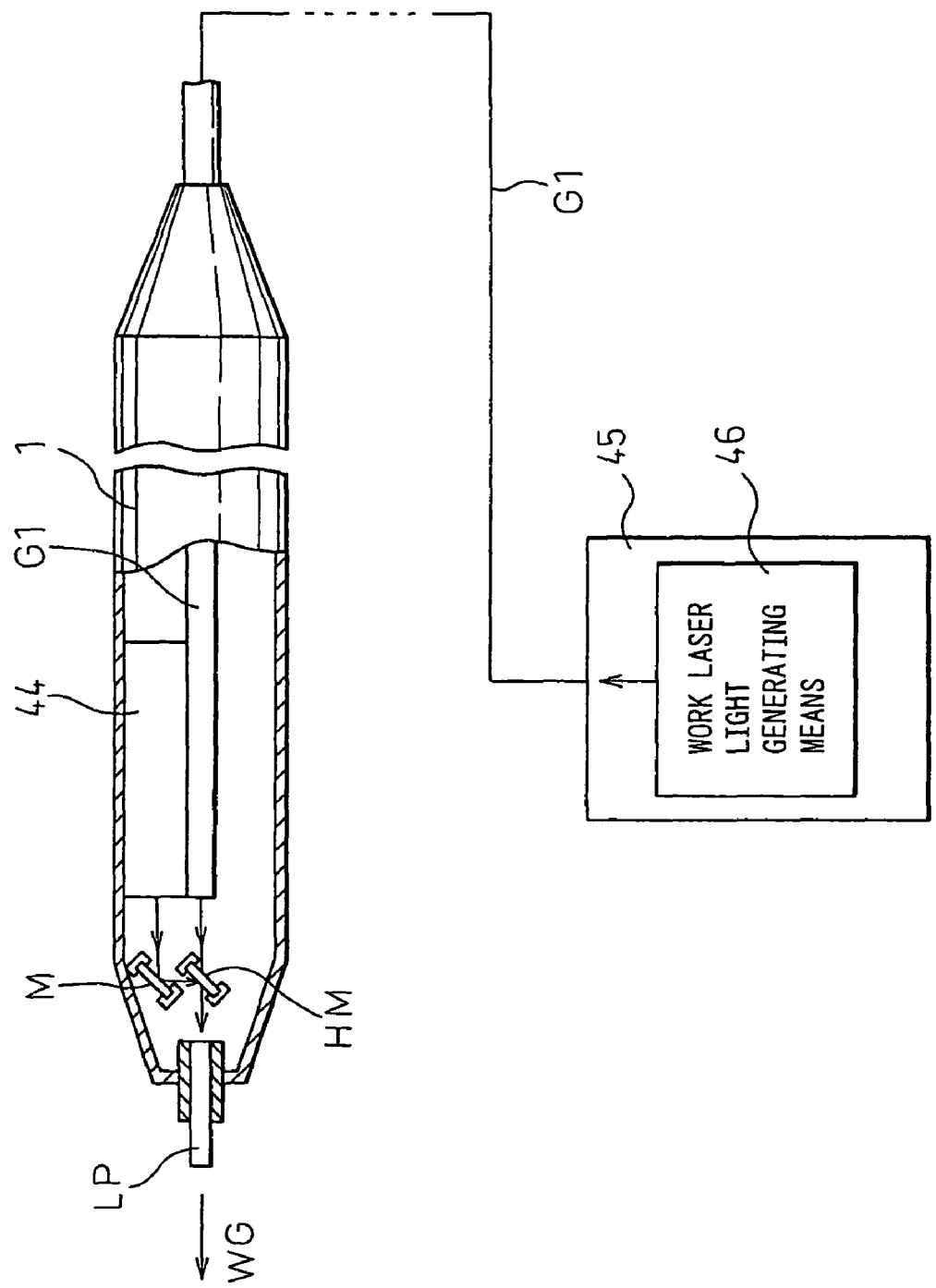
FIG. 31 is a diagram for explaining a 23rd specific example relating to the mounting of the light radiating unit according to the eighth embodiment in which the present invention is applied to the laser handpiece.

Next, FIG. 31 shows a laser handpiece according to a 23rd specific example which modifies the method of generating the guide light in the laser handpiece of the 22nd specific example shown in FIG. 30. In the 22nd specific example, the guide laser light generating means is provided within the laser generating apparatus 45, and the mixed light WG is produced using the dichroic mirror, but in the 23rd specific example, the guide laser light generating means is provided within the laser handpiece body. Accordingly, the mixed light WG is produced within the handpiece body.

As shown in FIG. 31, the work laser light is generated by the work laser light generating means 46 provided within the laser generating apparatus 45. The light is then guided through the light guide member G1 into the handpiece body 1 up to the laser probe LP from which the light is radiated toward the target area. On the other hand, the guide laser light is generated by the guide laser light generating means 44 provided within the handpiece body 1, and is mixed with the work laser light by using a mirror M and a dichroic mirror HM. The guide laser light generating means 44 can also generate the excitation laser light.

Figure 32A:
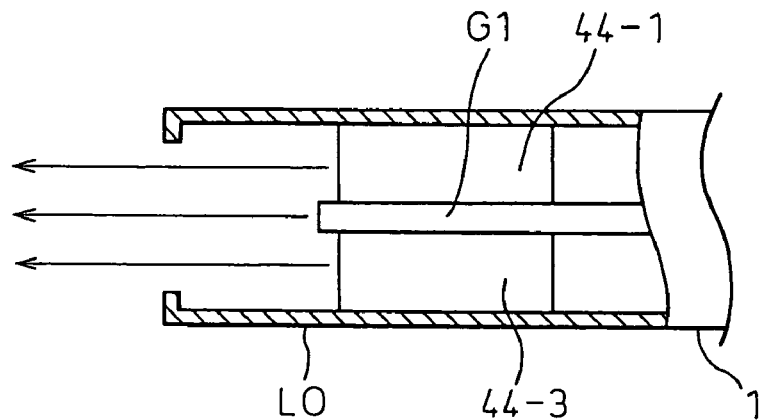
FIGS. 32A to 32C are diagrams for explaining a 24th specific example relating to the mounting of the light radiating unit according to the eighth embodiment in which the present invention is applied to the laser handpiece.
Figure 32B:
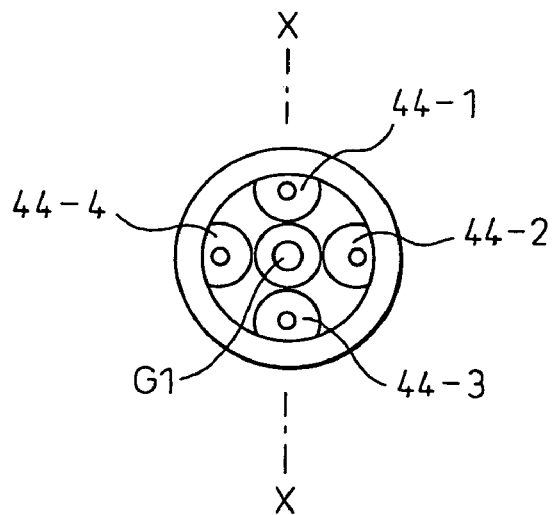
Figure 32C:
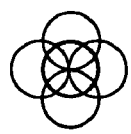

The laser handpieces according to the 22nd and 23rd specific examples described above are of the type that is equipped with the laser probe LP at the forward end of the handpiece body 1, i.e., at the laser light projection end, but a laser handpiece of the type that does not use such a laser probe LP is also possible, one example of which is shown as a 24th specific example in FIGS. 32A to 32C. In the 24th specific example, noting that the work laser light and the guide light do not necessarily need to be passed through the same path, but their light paths need only run in close proximity to each other, a plurality of guide laser light generating means 44-1 to 44-4 are arranged around the light guide member G1 through which the work laser light is guided, as shown in FIG. 32A. The cutaway view of the handpiece body 1 shown in FIG. 32A is a cross-sectional view taken along X-X in FIG. 32B which shows a front view of the handpiece body 1 as viewed facing the forward end thereof.

The work laser light emerging from the light guide member G1 is projected from the projection end LO (diagnostic/treatment tool) of the handpiece body 1 toward the target area, while the guide laser light is projected in parallel with the work laser light toward the target area. As shown in FIG. 32B, the plurality of guide laser light generating means 44-1 to 44-4 are arranged encircling the light guide member G1 in concentric fashion within the handpiece body 1; here, all of the plurality of guide laser light generating means 44-1 to 44-4 may be constructed to generate the excitation laser light, or alternatively, some of the guide laser light generating means may be constructed to generate the guide light, and the others to generate the excitation laser light. Further, the excitation laser light may be generated at the same wavelength or at different wavelengths. The excitation light is not limited to the laser generated light, but light generated by a light-emitting device such as an LED may be used.

FIG. 32C shows spots formed by the work laser light and the guide laser light projected onto the target area by using the laser handpiece according to the 24th specific example of FIGS. 32A and 32B. A thick-lined circle indicates the illumination spot of the work laser light, and four thin-lined circles formed around the illumination spot in partially overlapping fashion each indicate the spot of the guide light.

Next, a second mode of the dental diagnostic and treatment apparatus equipped with an intraoral illumination device according to the present invention will be described below with reference to ninth to twelfth embodiments by dealing with specific examples in which the light radiating means that can radiate light capable of distinctively detecting intraoral lesions is constructed so that it can be detachably mounted on an existing handpiece as described above.

Embodiment 9

The ninth embodiment concerns the case where the intraoral illumination device to be used in the dental diagnostic and treatment apparatus according to the present mode is of a power supply built-in type in which a power supply for supplying power for operating the light radiating means based on the above-described lesion detection principle is integrally built into an adapter that contains the light radiating means and that is designed to be detachably mounted on a dental instrument, and 25th to 27th specific examples relating to this type of intraoral illumination device mounted on the dental instrument are shown in FIGS. 33 to 38.

Figure 33A:
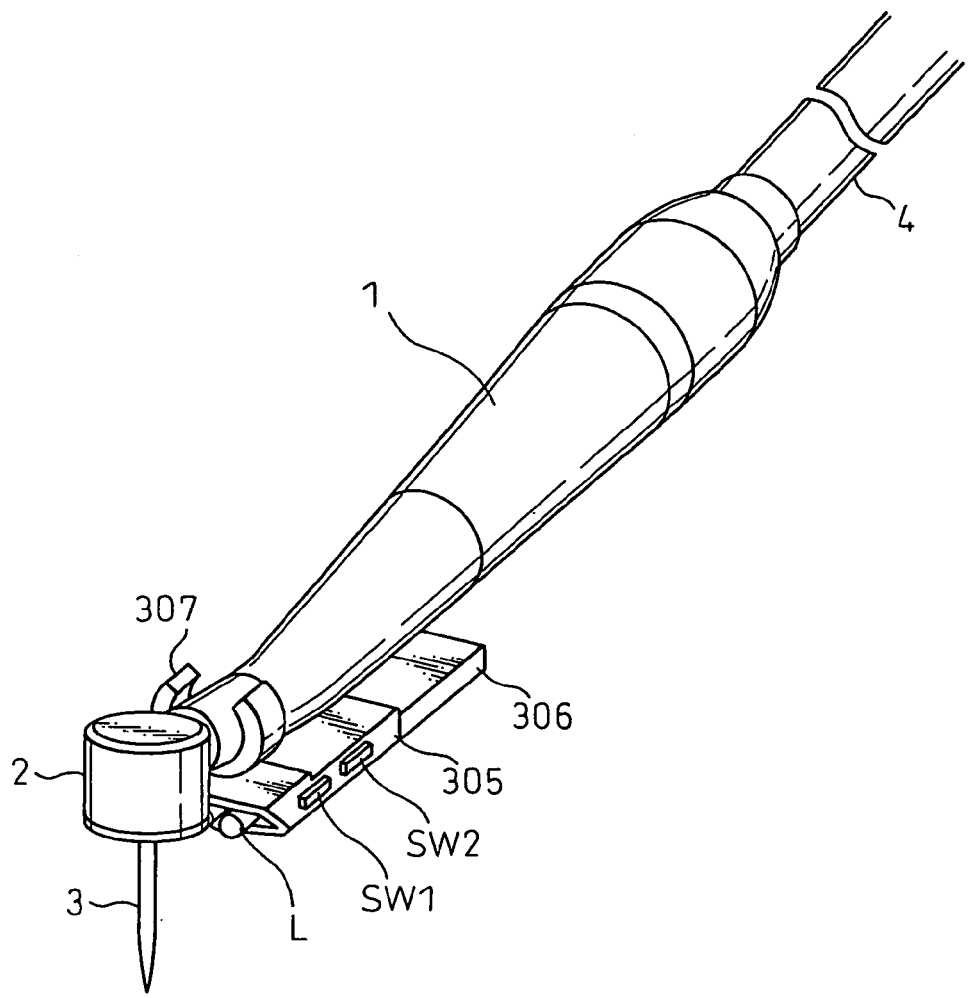
FIGS. 33A and 33B are diagrams for explaining a 25th specific example in which a power supply built-in type intraoral illumination device according to a ninth embodiment of the present invention is mounted on a handpiece body.

FIG. 33A shows the entire construction of the dental instrument, in which reference numeral 1 is the body of an air turbine handpiece as one example of the dental instrument, 2 is the head of the handpiece, and 3 is a treatment tool such as a bar (one example of a diagnostic/treatment tool) attached to the head. The handpiece body 1 is provided, at the end opposite from the head 2, with a joint which is detachable from the handpiece body 1 and which is connected via a tube 4 to a supply device such as an air supply device.

FIG. 33A shows the condition in which the intraoral illumination device according to the 25th specific example is mounted on the handpiece body 1. The intraoral illumination device of the 25th specific example comprises an adapter body 305, a power supply box 306, and a mounting member 307. The adapter body 305 is formed in a flat plate shape so as not to cause a problem in intraoral use when the head 2 is inserted in an oral cavity, and the light radiating means is mounted in one end of the body. Here, the adapter body 305 may be formed in a curved shape conforming with the shape of the outer circumference of the handpiece.

The light radiating means includes at least one light-emitting device L, and when a plurality of light-emitting devices L are provided, the plurality of light-emitting devices L are arranged side by side in a row conforming with the flat plate shape of the adapter body 305. Each of the plurality of light-emitting devices is provided with a converging lens, and the light projection direction of each light-emitting device is adjusted so that the projected light illuminates the area forward of the treatment tool 3 when the intraoral illumination device is mounted on the handpiece body 1. When the light radiating means comprises more than one light-emitting device L, all the light-emitting devices L may be constructed to emit light at the same wavelength, or the light-emitting devices L may be constructed to emit light at respectively different wavelengths. For example, a combination of illumination light and excitation light can be employed.

In the 25th specific example shown in FIG. 33A, since the dental instrument is an air turbine handpiece, the light projection direction of each light-emitting device is tilted by a certain angle relative to the center axis of the handpiece body 1. On the other hand, when the intraoral illumination device of the 25th specific example is used, for example, with a micromotor handpiece or a scaler handpiece to which the treatment tool 3 is attached along the center axis of the handpiece body 1, the plurality of light-emitting devices mounted in the adapter body 305 are oriented so that the light is projected in the direction parallel to the center axis.

The power supply box 306 containing the power supply for supplying power for operating the plurality of light-emitting devices is mounted on the end of the adapter body 305 opposite to the head-side end thereof. This power supply is a small-sized primary or secondary cell; in the case of a primary cell, a mercury button cell or the like is used, while in the case of a secondary cell, a lithium button or cylindrical cell or the like is used. Usually, the cell is inserted in the power supply box 306 in a replaceable fashion. In the case of a secondary cell, however, the cell may be permanently contained in the power supply box 306, and terminals for recharging the cell may be provided on a sidewall of the box.

When the plurality of light-emitting devices L as the light radiating means are mounted in the adapter body 5 as shown in FIG. 33A, a switch SW1 for switching the output of the built-in power supply in the power supply box 306 between the light-emitting devices L is provided on a sidewall of the adapter body 305. The switch SW1 may be constructed to be able to turn on and off the power supply, or alternatively, the power supply box 306 itself may be constructed to be able to be detachably connected to the adapter body 305 by means of pins so that power is turned on when the power supply box 306 is connected to the adapter body 305.

Another switch SW2 is provided side by side with the switch SW1 on the sidewall of the adapter body 305. The light output level of each light-emitting device can be adjusted by using the switch SW2. For example, by operating the switch SW2 on and off, the light output level can be adjusted between two levels. The switch SW2 may be replaced by a small variable resistor so that the output light level can be adjusted in a stepless manner.

Further, the adapter body 305 is provided with the mounting member 307 to enable the intraoral illumination device of the 25th specific example to be mounted detachably on the dental instrument. Consideration must be taken so that the intraoral illumination device, when mounted on the dental instrument, does not interfere with the intraoral operability of the instrument. In view of this, in the case shown in FIG. 33A, the mounting member 307 is provided on the upper side of the adapter body 305 and, when mounted, elastically holds the base of the air turbine handpiece head.

Figure 33B:
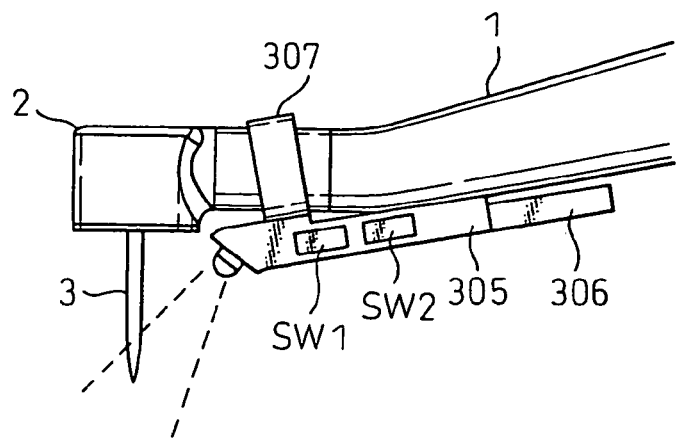

FIG. 33B shows the intraoral illumination device mounted for use according to the 25th specific example; the diagram shown here is an enlarged side view of the forward end portion of the air turbine handpiece shown in FIG. 33A. In FIG. 33B, light being emitted from the light-emitting device L is shown by dashed lines. As shown, the illumination light or excitation light emitted from the light-emitting device L illuminates the area forward of the treatment tool 3 in the axis direction thereof.

The 25th specific example has been described above for the power supply built-in type intraoral illumination device according to the ninth embodiment. In the 25th specific example, the intraoral illumination device is detachably mounted on the base of the head 2 of the air turbine handpiece; on the other hand, FIGS. 34A and 34B show as the 26th specific example an example of the power supply built-in type intraoral illumination device that can be detachably mounted on the forward end of the treatment tool mounting portion of the head 2.

Figure 34A:
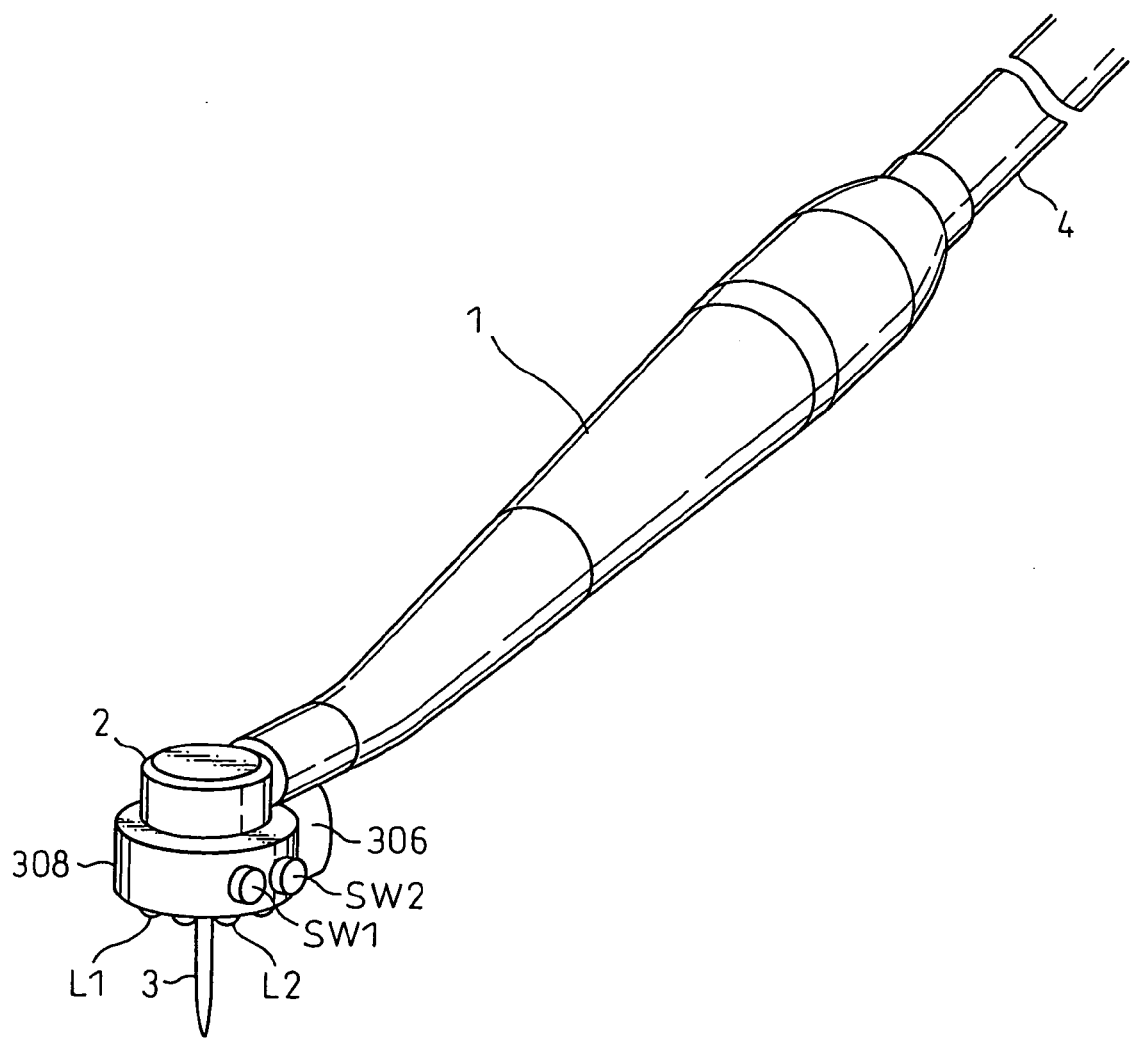
FIGS. 34A and 34B are diagrams for explaining a 26th specific example in which the intraoral illumination device according to the ninth embodiment is mounted on a handpiece head.

In FIG. 34A also, the dental instrument is an air turbine handpiece, and the same parts as those in FIG. 33A are designated by the same reference numerals. The intraoral illumination device of the 26th specific example shown in FIG. 34A is constructed so that it is mounted on the forward end of the head 2 by press fitting; therefore, the whole device structure is formed in a ring shape, not a flat plate shape, and the adapter body 308 is therefore ring-shaped.

Because of the ring shape, in the intraoral illumination device of the 26th specific example, the plurality of light-emitting devices L forming the light radiating means are arranged in a ring in such a manner as to encircle the treatment tool 3. The power supply box 306 for supplying power to the light-emitting devices L is mounted on an outer circumferential sidewall of the adapter body 308 so that when the device is mounted on the head 2, the power supply box 30 is positioned near the base of the head 2 and is thus kept out of the way. The switches SW1 and SW2 provided on the intraoral illumination device in the 26th specific example are the same as those shown in the 25th specific example, and the power supply box 306 is also the same.

Figure 34B:
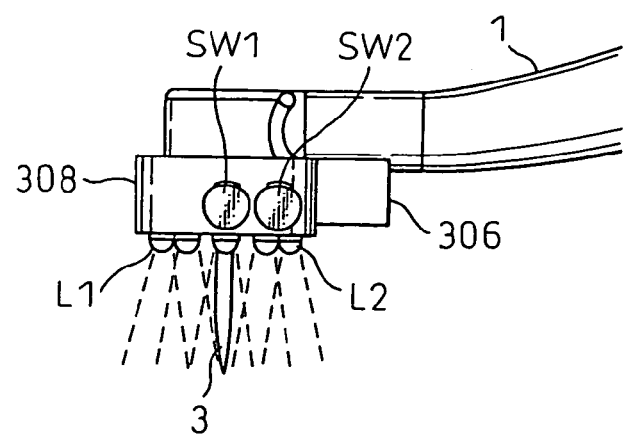

FIG. 34B shows the intraoral illumination device mounted for use according to the 26th specific example; the diagram shown here is an enlarged side view of the forward end portion of the air turbine handpiece shown in FIG. 34A. In FIG. 34B, lights being emitted from the light-emitting devices L1 and L2 at two different wavelengths are shown by dashed lines. As shown, for example, when illumination light is emitted from the light-emitting devices L1, and excitation light from the light-emitting devices L2, the light-emitting devices L1 and L2 are arranged alternately, and the light from each light-emitting device is projected in parallel to the axis direction of the treatment tool 3 and illuminates forward thereof. In this way, with the plurality of light-emitting devices arranged in a ring, the lights are radiated in such a manner as to encircle the axis of the treatment tool 3 and can thus provide shadowless illumination to the lesion located in the forward direction.

Figure 35A:
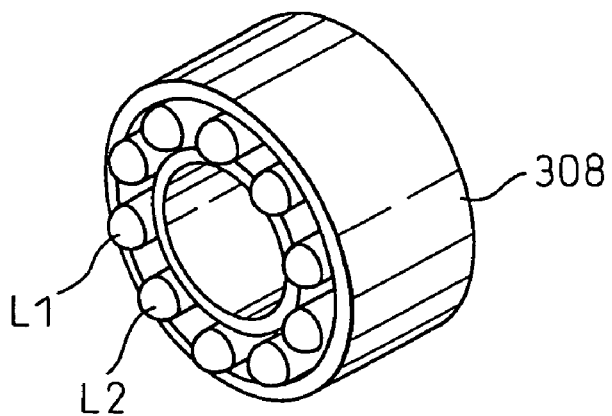
FIGS. 35A to 35C are diagrams for explaining a modified example of the intraoral illumination device of the 26th specific example.
Figure 35B:
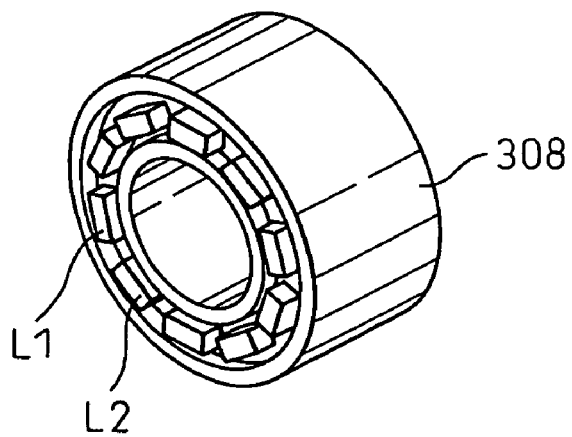
Figure 35C:
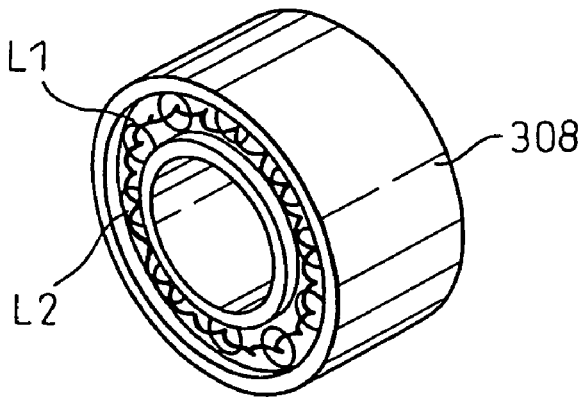

FIGS. 35A to 35C show examples of the arrangement of the plurality of light-emitting devices in the adapter body 308 of the intraoral illumination device according to the 26th specific example. FIG. 35A shows the case where the light-emitting devices are shell-shaped LEDs, FIG. 35B shows the case of chip LEDs, and FIG. 35C shows the case of bare chip LEDs; in each case, the plurality of light-emitting devices L1 and L2 are arranged around the periphery of the forward end of the ring-shaped adapter body 308, and are supplied with power from the power supply box 306 via a ring-shaped wiring substrate or the like. An opening allowing at least the treatment tool 3 to freely pass through is formed in the center portion encircled by the plurality of light-emitting devices L1 and L2 arranged in a ring.

Figure 36:
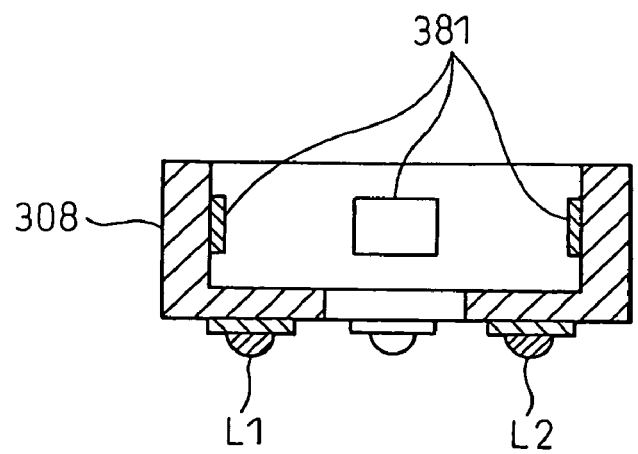
FIG. 36 is a diagram for explaining an example of the internal structure of a ring-shaped adapter in the intraoral illumination device.

FIG. 36 shows a cross-sectional view of the adapter body 308 of the intraoral illumination device according to the 26th specific example; the portion around the axis of the treatment tool 3 is shown here. A space in which the forward end of the head 2 is inserted is formed in the center of the adapter body 308, and the opening through which the treatment tool 3 is inserted is also formed. A plurality of non-slip members 381 are bonded to the inner circumferential surface of the adapter body 308 to prevent the adapter body 308 press-fitted on the forward end of the head 2 from coming off.

Instead of the non-slip members, engaging members using screws or pawls may be employed to prevent the adapter body 308 from coming off the head 2. While the 26th specific example has been described for the case of an air turbine handpiece as an example, the intraoral illumination device can also be mounted on such a dental instrument as a micromotor handpiece, a scaler handpiece, or a vacuum syringe to which the treatment tool (diagnostic tool) 3 is attached with its axis aligned with the center axis of the handpiece body 2.

The adapter body 308 of the intraoral illumination device according to the 26th specific example described above is integrally formed from a relatively rigid synthetic resin or the like. However, the diameter of the forward end of the dental instrument on which the intraoral illumination device is to be mounted often varies, depending on the kind of the instrument used, and if such varying diameters are to be supported, intraoral illumination devices that match the different diameters have to be prepared, which would be uneconomical. In view of this, the intraoral illumination device according to the 27th specific example shown in FIG. 37 is constructed so as to be able to flexibly accommodate different forward end diameters.

Figure 37:
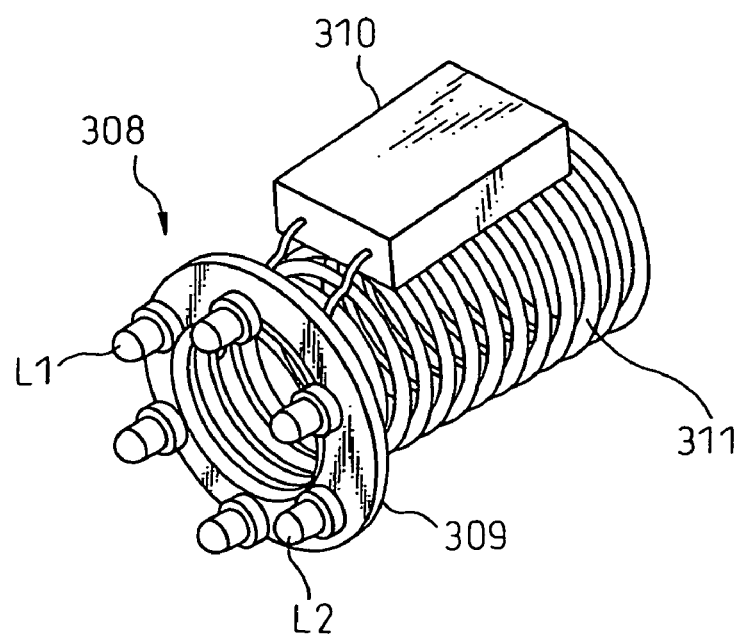
FIG. 37 is a diagram for explaining a 27th specific example of the intraoral illumination device according to the ninth embodiment which is mounted on another handpiece head.

The intraoral illumination device according to the 27th specific example shown in FIG. 37 comprises an adapter body 308, a power supply box 310, and a coiled mounting member 311. The adapter body 308 includes a plurality of light-emitting devices L1 and L2 and a light source mounting member 309; this mounting member 9 is formed in a ring shape and includes a wiring substrate on which the plurality of light-emitting devices L1 and L2 are arranged in a ring.

The method of arranging the light-emitting devices as the light radiating means is the same as that employed in the 26th specific example, but the selector switch is mounted on a sidewall of the power supply box 311. The light-emitting devices L1 and L2 mounted on the light source mounting member 308 are supplied with power via lead wires from the power supply box 310 containing a primary or secondary cell.

The light source mounting member 308 is attached to the coiled mounting member 311 whose inner diameter is the smallest at its end nearest to the light source mounting member 308 and becomes gradually larger toward the other end. The intraoral illumination device equipped with this coiled mounting member 311 is advantageous, among others, for such dental instruments as a straight micromotor handpiece, a scaler handpiece, and a vacuum syringe to which the treatment tool 3 is attached with its axis aligned with the center axis of the handpiece body 2.

Figure 38:
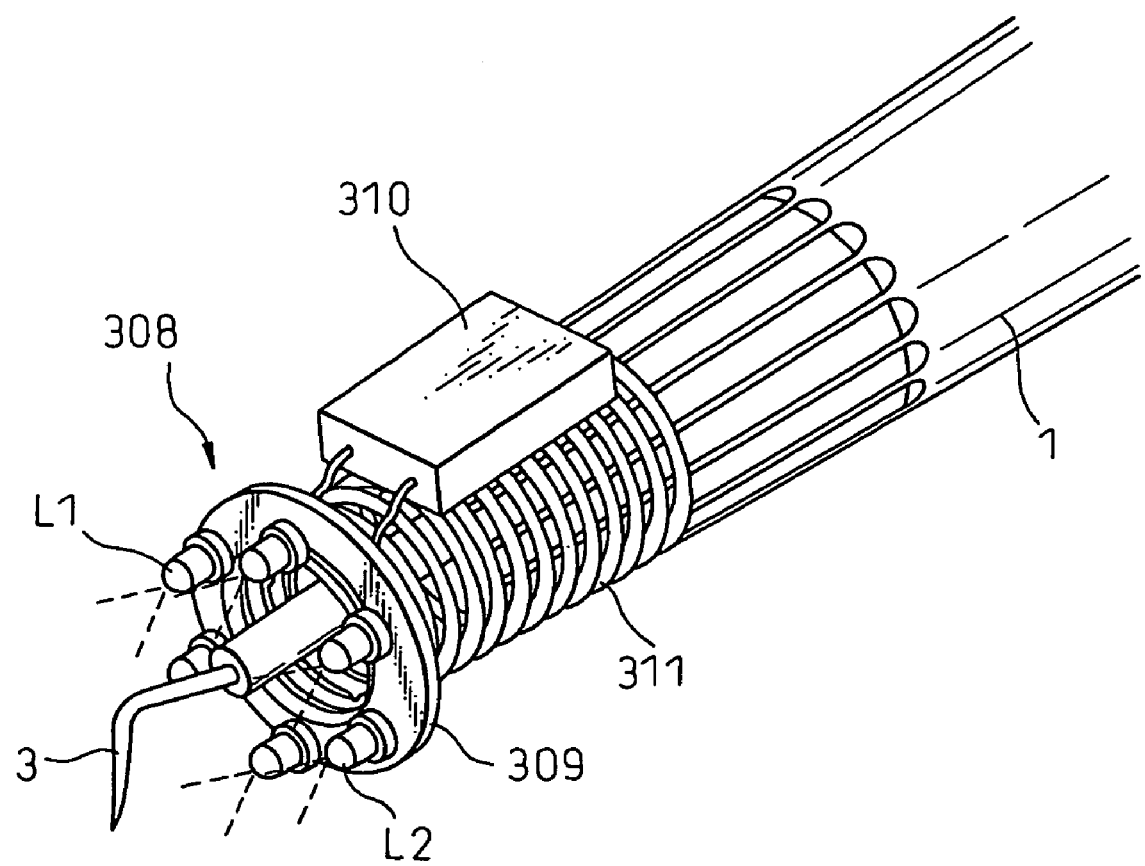
FIG. 38 is a diagram for explaining the condition in which the intraoral illumination device of the 27th specific example is mounted on the handpiece head.

FIG. 38 shows an example of use when the intraoral illumination device of the 27th specific example is mounted on the scaler handpiece. As can be seen from FIG. 38, the forward end of the handpiece body 1 is press-fitted into the coiled mounting member 311 whose coil then expands according to the diameter of the forward end while exerting a contracting force by the elasticity of the coil, and the intraoral illumination device is thus fitted onto the forward end of the scaler handpiece. At this time, the light projection direction of each light-emitting device is parallel to the center axis of the handpiece body 1, and the light is radiated in such a manner as to encircle the treatment tool 3 attached to the scaler, and thus provides shadowless illumination in the direction forward of the treatment tool 3.

Embodiment 10

While the ninth embodiment has shown the power supply built-in type intraoral illumination device in which the power supply for supplying power to the light radiating means mounted in the adapter is integrally built into the adapter, the 10th embodiment hereinafter described concerns a power supply separated type construction in which the power supply for supplying power for operating the light radiating means based on the above-described lesion detection principle is separated from the adapter that contains the light radiating means and that is designed to be detachably mounted on the dental instrument, and 28th to 34th specific examples relating to this type of intraoral illumination device mounted on the dental instrument are shown in FIGS. 39 to 47.

FIGS. 39A and 39B show the 28th specific example of the intraoral illumination device according to the 10th embodiment. The basic construction of the adapter body is the same as that of the power supply built-in type intraoral illumination device shown in the 25th specific example of the ninth embodiment, but the difference is that the power supply for supplying power to the light radiating means mounted in the adapter body is located away from the adapter and is connected to the adapter by a power supply line. In FIGS. 39A and 39B, the same parts as those in FIGS. 33A and 33B are designated by the same reference numerals.

In FIG. 39A also, the adapter body 305 of the intraoral illumination device is mounted on the air turbine handpiece body 1, which is one example of the dental instrument, by using the mounting member 307. FIG. 39B shows an example of use of the intraoral illumination device according to the 28th specific example in a manner similar to that of the 25th specific example shown in FIG. 33B.

The intraoral illumination device of the 28th specific example comprises the adapter body 305 with a plurality of light-emitting devices L as the light radiating means mounted at its forward end and a power supply box 312 containing the power supply for supplying power to the light-emitting devices L, and the power supply box 312 is connected to the adapter body 305 by the power supply line 313. The power supply box 312 may be of the type that contains a primary or secondary cell as the power supply or of the type that provides regulated DC power derived from AC commercial power. In FIG. 39A, the power supply box 312 is shown as being located near the handpiece body 1 for illustrative purposes, but actually, the power supply box 312 may be built, for example, into the air supply control apparatus for the dental instrument, or may be worn on the clinician.

As in the 25th specific example, the light radiating means in the intraoral illumination device of the 28th specific example includes at least one light-emitting device L, and the plurality of light-emitting devices L are arranged side by side in a row conforming with the flat plate shape of the adapter body 305. Each of the plurality of light-emitting devices is provided with a converging lens, and the light projection direction of each light-emitting device is adjusted so that the projected light illuminates the area forward of the treatment tool 3 when the intraoral illumination device is mounted on the handpiece body 1. When the light radiating means comprises more than one light-emitting device L, all the light-emitting devices L may be constructed to emit light at the same wavelength, or the light-emitting devices L may be constructed to emit light at respectively different wavelengths. For example, a combination of illumination light and excitation light can be employed.

In the example of use of the 28th specific example shown in FIG. 39B, since the dental instrument is an air turbine handpiece, the light projection direction of each light-emitting device is tilted by a certain angle relative to the center axis of the handpiece body 1. On the other hand, when the intraoral illumination device of the 28th specific example is used, for example, with a micromotor handpiece or a scaler handpiece to which the treatment tool 3 is attached along the center axis of the handpiece body 1, the plurality of light-emitting devices mounted on the adapter body 305 are oriented so that the light is projected in the direction parallel to the center axis.

The power supply line 313 extending from the power supply box 312 containing the power supply for supplying power for operating the plurality of light-emitting devices is connected to the end of the adapter body 305 opposite to the head-side end thereof. When the plurality of light-emitting devices L as the light radiating means are mounted in the adapter body 305, a switch SW for switching the connection of the power supplied via the power supply line 313 between the light-emitting devices L is provided on a sidewall of the adapter body 305. A power on/off switch may be provided on the adapter body 305 or on the power supply box 312 or at a suitable position along the power supply line.

Another switch SW2 may be provided side by side with the switch SW1 on the sidewall of the adapter body 305, and the light output level of each light-emitting device may be adjusted by using the switch SW2. For example, by operating the switch SW2 on and off, the light output level can be adjusted between two levels. The switch SW2 may be replaced by a small variable resistor so that the output light level can be adjusted in a stepless manner.

The 28th specific example has been described above for the power supply separated type intraoral illumination device according to the 10th embodiment. In the 28th specific example, the intraoral illumination device is detachably mounted on the base of the head 2 of the air turbine handpiece; on the other hand, FIGS. 40A and 40B show as the 29th specific example an example in which the detachable mounting structure of the intraoral illumination device is made compact by simplifying the structure of the adapter body of the intraoral illumination device of the 28th specific example.

Figures 40A, 40B:
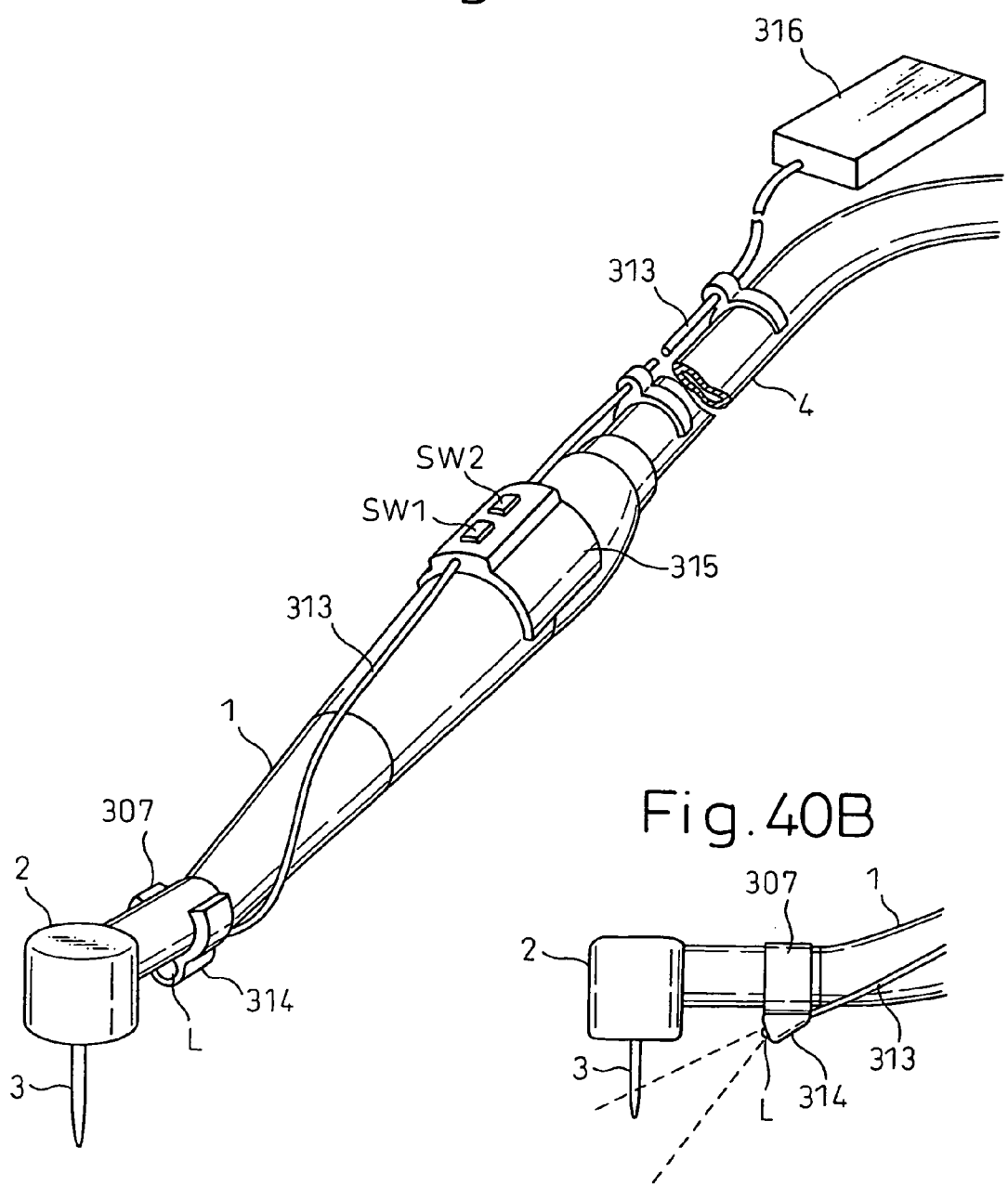
FIGS. 40A and 40B are diagrams for explaining a 29th specific example in which a switch operating part in the intraoral illumination device according to the 10th embodiment is mounted on the handpiece body.

In FIG. 40A also, the intraoral illumination device according to the 29th specific example is mounted on the air turbine handpiece body 1 which is one example of the dental instrument. FIG. 40B shows an example of use of the intraoral illumination device according to the 29th specific example in a manner similar to that of the 25th specific example shown in FIG. 33B, that is, an enlarged view only of the portion near the head 2 is shown.

The intraoral illumination device of the 29th specific example comprises a light-emitting device L as the light radiating means, a light source mounting member 314 for holding the light-emitting device L, a switch holding member 315, and a power supply box 316. The light source mounting member 314 is detachably held on the base of the head 2 of the handpiece body 1 by the elasticity of the mounting member 307 integrally formed with the mounting member 314. The switch holding member 315 also has an integrally molded elastic structure and detachably mounted on the barrel of the handpiece body 1.

The switch holding member 315 is formed with switch parts comprising switches SW1 and SW2, and power from the power supply box 316 is supplied via a power supply line 13 to the light-emitting device L, the on/off operation of which is controlled by the switch parts. Here, the light-emitting device L may be constructed from a device that emits light of only one wavelength or from an array of a plurality of devices that emit lights of different wavelengths. In the 28th specific example, the light-emitting device is constructed from an array of a plurality of devices.

Another switch SW2 is provided on the sidewall of the switch holding member 315 side by side with the switch SW1 for switching the light emission operation of the light-emitting device L, and the output light level of each light-emitting device L can be adjusted by using the switch SW2. For example, by operating the switch SW2 on and off, the light output level can be adjusted between two levels. The switch SW2 may be replaced by a small variable resistor so that the output light level can be adjusted in a stepless manner.

In the example of use of the 29th specific example shown in FIG. 40B, as in the example of use of the 28th specific example shown in FIG. 39B, since the dental instrument is an air turbine handpiece, the light projection direction of each light-emitting device is tilted by a certain angle relative to the center axis of the handpiece body 1. On the other hand, when the intraoral illumination device of the 29th specific example is used, for example, with a micromotor handpiece or a scaler handpiece to which the treatment tool 3 is attached along the center axis of the handpiece body 1, the light-emitting device is oriented so that the light is projected in the direction parallel to the center axis. The intraoral illumination device of the 29th specific example, which does not use a bulky adapter such as employed in the 28th specific example, requires the power supply line, but the entire construction can be made slim.

Figure 41:
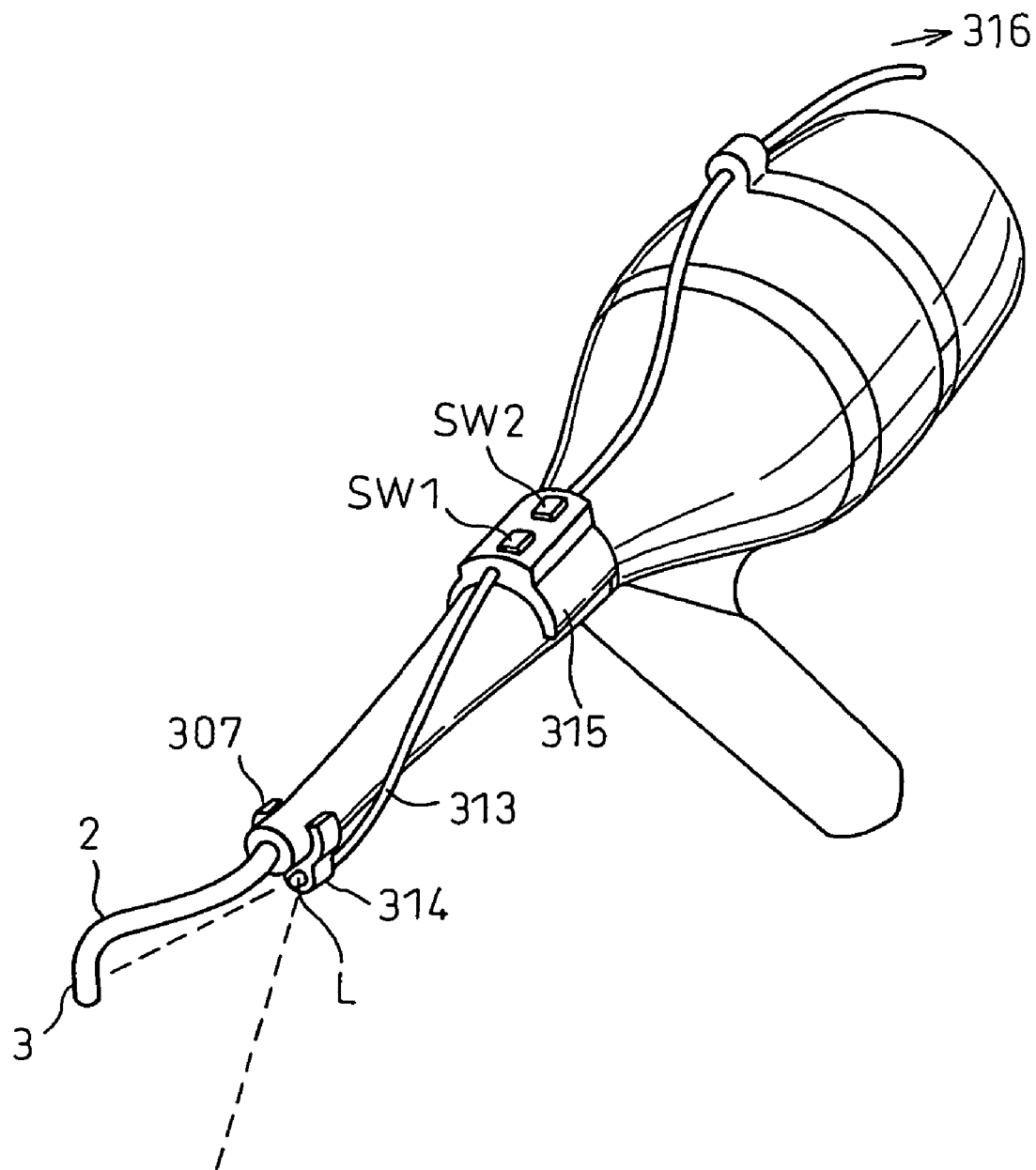
FIG. 41 is a diagram for explaining a 30th specific example in which the intraoral illumination device of the 29th specific example is mounted on another dental instrument.

Next, FIG. 41 shows the 30th specific example in which the detachable intraoral illumination device according to the 29th specific example is mounted, for example, on a tooth cleaning device which is one kind of dental instrument. The intraoral illumination device according to the 30th specific example is identical in construction to that of the 29th specific example, except that a tooth cleaning fluid is sprayed from the forward end (diagnostic/treatment tool) 3 of the nozzle 2 forming the handpiece head, and comprises the light-emitting device L as the light radiating means, the light source mounting member 314 for holding the light-emitting device L, the switch holding member 315, and the power supply box 316. In FIG. 41, the power supply box 316 is not shown.

Syringes and vacuums are instruments usually used by hygienists, and a three-way syringe is used to spray water and air to the treatment area, while a vacuum syringe is used to evacuate fluids and debris from the treatment area; therefore, the forward ends (diagnostic/treatment tools) of these instruments are pointed toward the treatment area. In this way, when the intraoral illumination device having an excitation light source is mounted on a three-way syringe or a vacuum syringe as shown in the 30th specific example, the lesion in the oral cavity can be made clearly visible without impairing the operability of other dental instruments such as a drilling instrument that the clinician uses for intraoral treatment. Accordingly, if the excitation light source can be mounted on the instrument that the hygienist uses, the excitation light source does not need to be mounted on the instrument that the dentist as the clinician uses, and therefore the operability is not degraded.

Figure 42A:
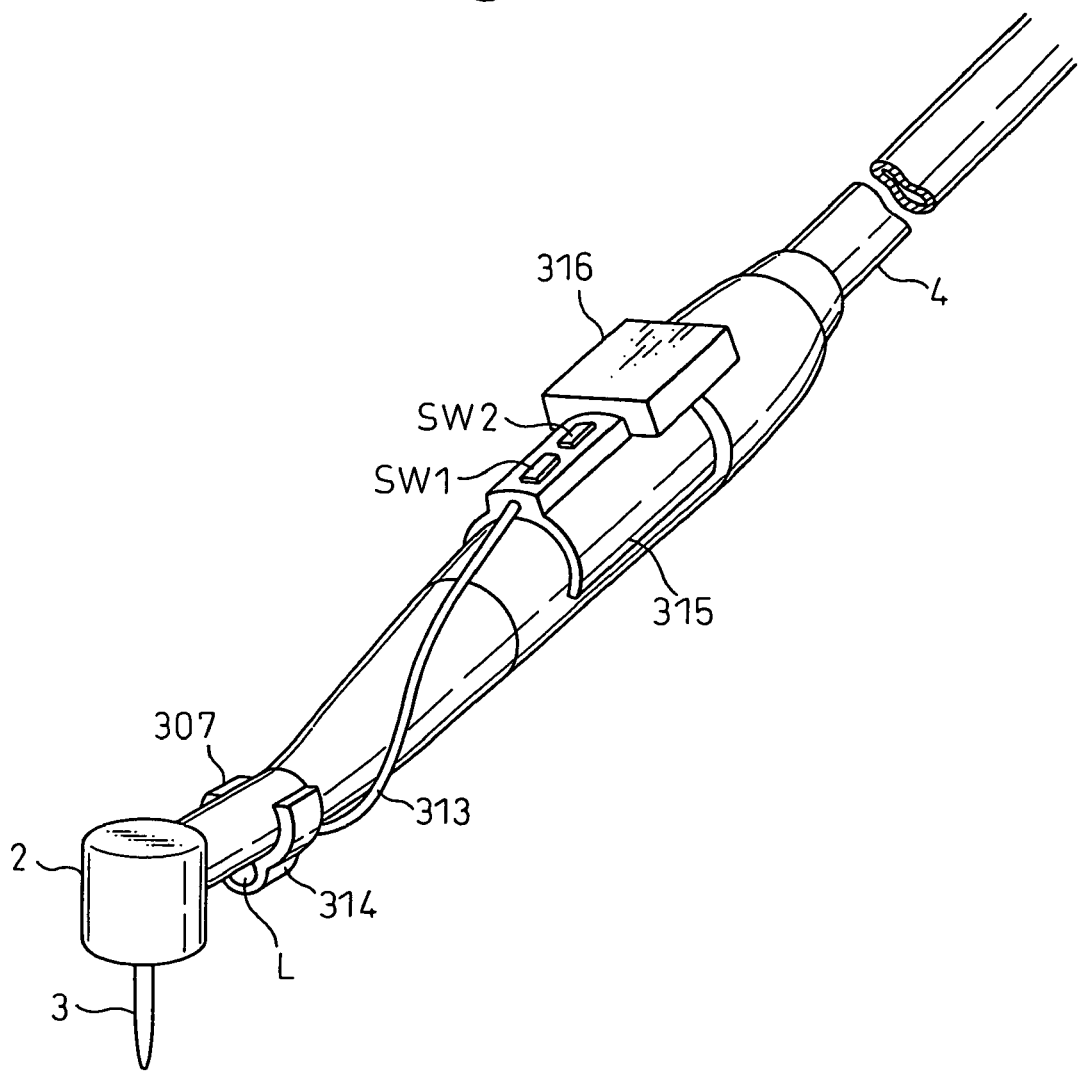
FIGS. 42A and 42B are diagrams for explaining a 31st specific example in which a power supply is integrated with the switch operating part in the intraoral illumination device of the 29th specific example.
Figure 42B:
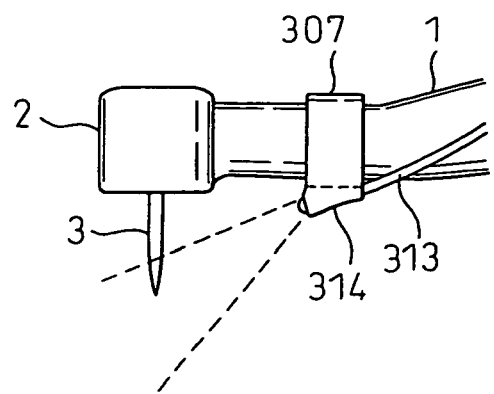

The intraoral illumination device according to the 31st specific example shown in FIGS. 42A and 42B is a modification of the intraoral illumination device of the 29th specific example shown in FIGS. 40A and 40B, and essentially comprises the light-emitting device L as the light radiating means, the light source mounting member 314 for holding the light-emitting device L, the switch holding member 315, the power supply line 313, and the power supply box 316.

However, while in the intraoral illumination device of the 29th specific example shown FIG. 40A, the power supply box 316 is placed at a remote location and connected to the switch parts via the power supply line 313, in the intraoral illumination device of the 31st specific example shown FIG. 42A the power supply box 316 is directly attached to the switch holding member 315 forming the switch parts, and the power supply line therebetween is thus eliminated. In this way, the intraoral illumination device of the 31st specific example is mounted on the side face of the handpiece body 1 in a clustered fashion and, despite its power supply separated construction, the entire construction is made compact. The function of the intraoral illumination device itself is the same as that of the 29th specific example.

Next, FIGS. 43A and 43B show the 32nd specific example in which the power supply built-in type intraoral illumination device shown as the 26th specific example of the ninth embodiment is converted to a power supply separated type intraoral illumination device. As in the 26th specific example, FIG. 43A shows an example in which the intraoral illumination device is mounted on an air turbine handpiece which is one example of the dental instrument, and FIG. 43B shows an enlarged view of the portion near the handpiece head with the intraoral illumination device mounted for use.

The structure of the adapter body 308 employed for the intraoral illumination device 8 of the 32nd specific example is exactly the same as that employed in the 26th specific example, and its light radiating function is the same as that of the 26th specific example. Therefore, the description thereof will not be repeated here. However, while in the power supply built-in type intraoral illumination device of the 26th specific example, the power supply box 306 is attached to the sidewall of the adapter body 308, in the 32nd specific example the power supply box 312 is located at a suitable distance away from the adapter body 308 and supplies power via the power supply line 313 to the light-emitting devices L mounted as the light radiating means in the adapter body 308. This arrangement of the power supply box 312 is the same as that shown in the 28th specific example.

Figure 44A:
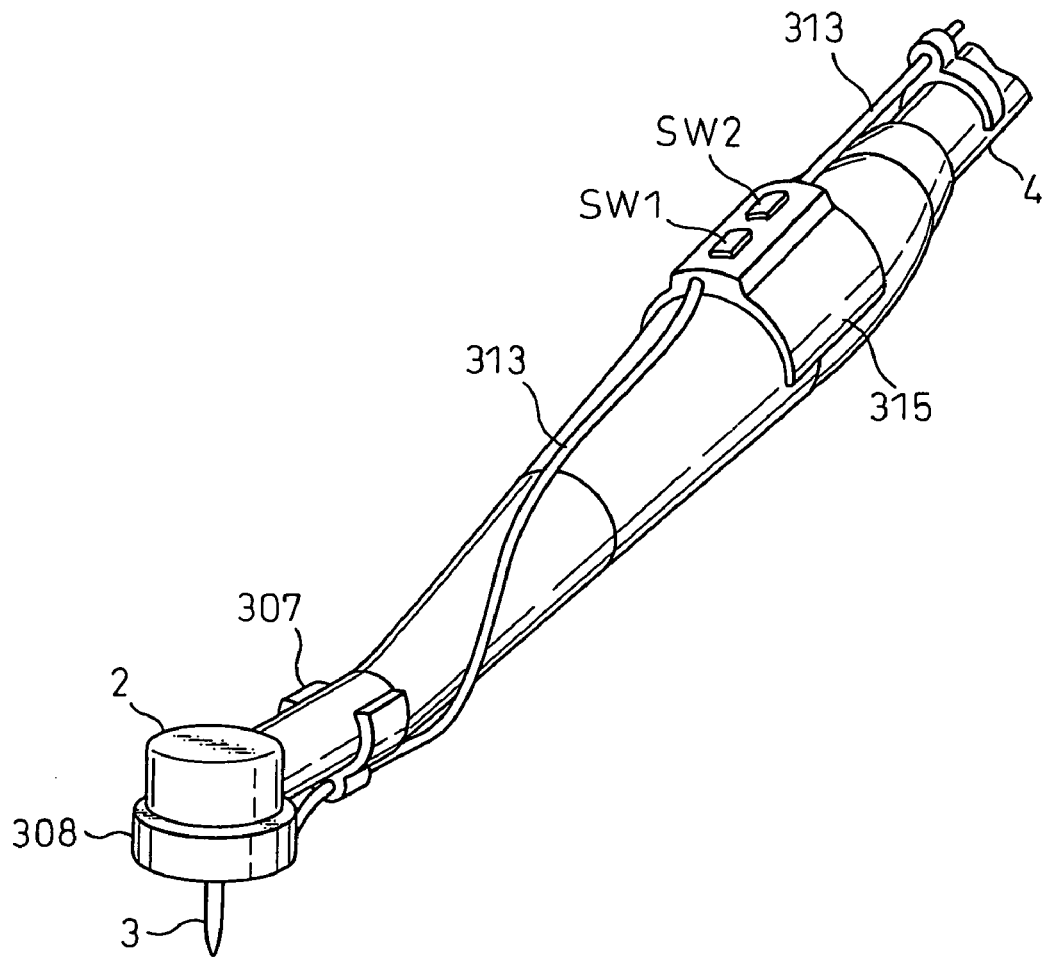
FIGS. 44A and 44B are diagrams for explaining a 33rd specific example in which the intraoral illumination device having a ring-shaped adapter is applied to the 29th specific example.
Figure 44B:
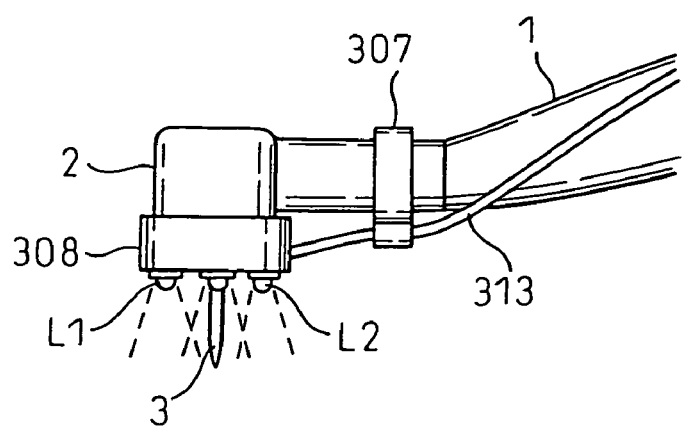

Next, the 33rd specific example of the intraoral illumination device shown in FIGS. 44A and 44B is based on the 32nd specific example of the intraoral illumination device shown in FIGS. 43A and 43B, but the difference is that the switches SW1 and SW2 for controlling the operation of the light radiating means are not provided on the sidewall of the adapter body 308 but are incorporated as switch parts in the switch holding member 315 which is detachable from the barrel of the handpiece body 1, as in the 29th or 30th specific example. This arrangement serves to prevent the switch parts from being operated unexpectedly by hitting a tooth or the like during intraoral treatment.

Figure 45A:
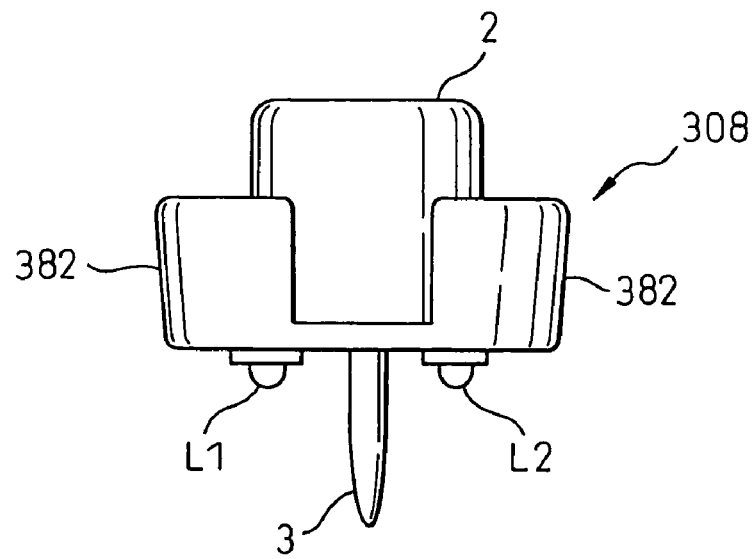
FIGS. 45A and 45B are diagrams for explaining another example of the internal structure of the ring-shaped adapter in the intraoral illumination device.
Figure 45B:
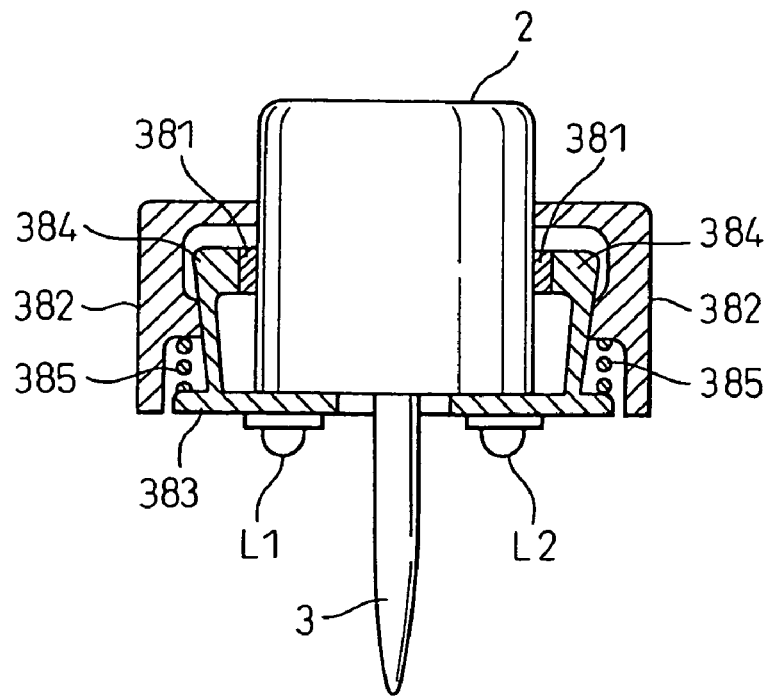

The mounting structure of the adapter body 308 employed in the intraoral illumination device of the 33rd specific example for mounting on the head 2 will be described below with reference to FIGS. 45A and 45B. FIG. 45A shows an external view of the adapter body 308 mounted on the head 2, and FIG. 45B shows the mounting structure, partly in cross section revealing the internal structure of the adapter body 308.

Here, the mounting structure of the adapter body 308 in the intraoral illumination device of the 26th specific example shown in FIG. 36 can be employed for mounting the adapter body 308 on the head 2, but the mounting structure shown in FIG. 36 may not be able to provide reliable mounting because of the use of the non-slip members 381.

In view of this, to ensure reliable mounting, a structure is employed that securely presses the plurality of non-slip members 381 against the sidewall of the head 2 when the adapter body 308 is mounted on the head 2. The adapter body 308 includes a case member 382, a ring-shaped light source mounting member 383 capable of-mounting a plurality of light-emitting devices L thereon, a plurality of engaging piece members 384 with the non-slip members attached to their ends, and a spring member 385. Each of these members can be formed from a synthetic resin.

The engaging piece members 384 are formed integrally with the light source mounting member 383 in such a manner as to protrude from it, and are tilted slightly outward. On the other hand, protrusions that slidably contact the sloped faces of the engaging piece members 384 are formed on the inner circumferential surface of the case member 382 along the entire circumference thereof or at positions corresponding to the positions of the respective engaging piece members 384. The spring member 385 is interposed between the light source mounting member 383 and the protrusions formed on the case member 82.

When mounting the thus constructed adapter body 308 on the head 2, first the case member 382 and the light source mounting member 383 are pressed together against the spring force of the spring member 385. This causes the protrusions to move downward, allowing the engaging piece members 384 to deflect outward and thus making ready to accommodate the head 2.

Then, the head 2 is inserted in the space formed inside the adapter body 308, and the pressing force is released; thereupon, the protrusions on the case member 382 are caused to slide upward along the sloped faces of the engaging piece members 384 due to the spring force of the spring member 385, and thus press the non-slip members 381 against the outer circumferential surface of the head 2. The mounting of the adapter body 308 on the head 2 is thus completed, and the adapter body 308 is securely held in place with the movements of the engaging piece members 384 restricted by the sliding faces of the protrusions.

Figure 46:
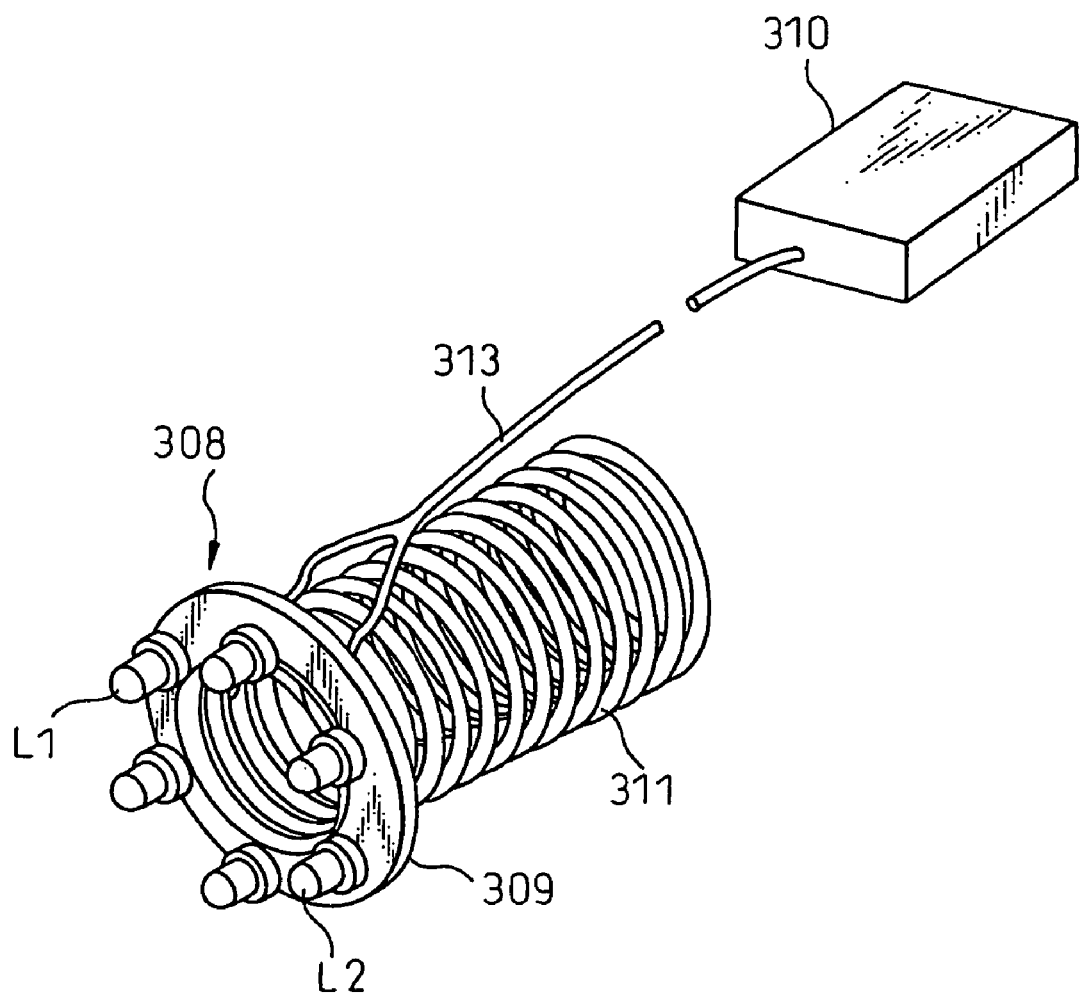
FIG. 46 is a diagram for explaining a 34th specific example in which the intraoral illumination device of the 27th specific example is converted to a power supply separated type.

Next, FIG. 46 show the 34th specific example in which the power supply built-in type intraoral illumination device shown as the 27th specific example of the ninth embodiment is converted to a power supply separated type intraoral illumination device. The structure of the adapter body 308 employed for the intraoral illumination device of the 34th specific example is exactly the same as that employed in the 27th specific example shown in FIG. 37, and its light radiating function is the same as that of the 27th specific example; therefore, the description thereof will not be repeated here.

However, while in the power supply built-in type intraoral illumination device of the 27th specific example, the power supply box 310 is attached via lead wires to the light source mounting member 309 of the adapter body, in the 34th specific example the power supply box 310 is located at a suitable distance away from the adapter body 308 and supplies power via the power supply line 313 to the light-emitting devices L mounted as the light radiating means on the light source mounting member 309 of the adapter body 308. This arrangement of the power supply box 310 is the same as that shown in the 28th specific example of FIG. 39A.

Figure 47:
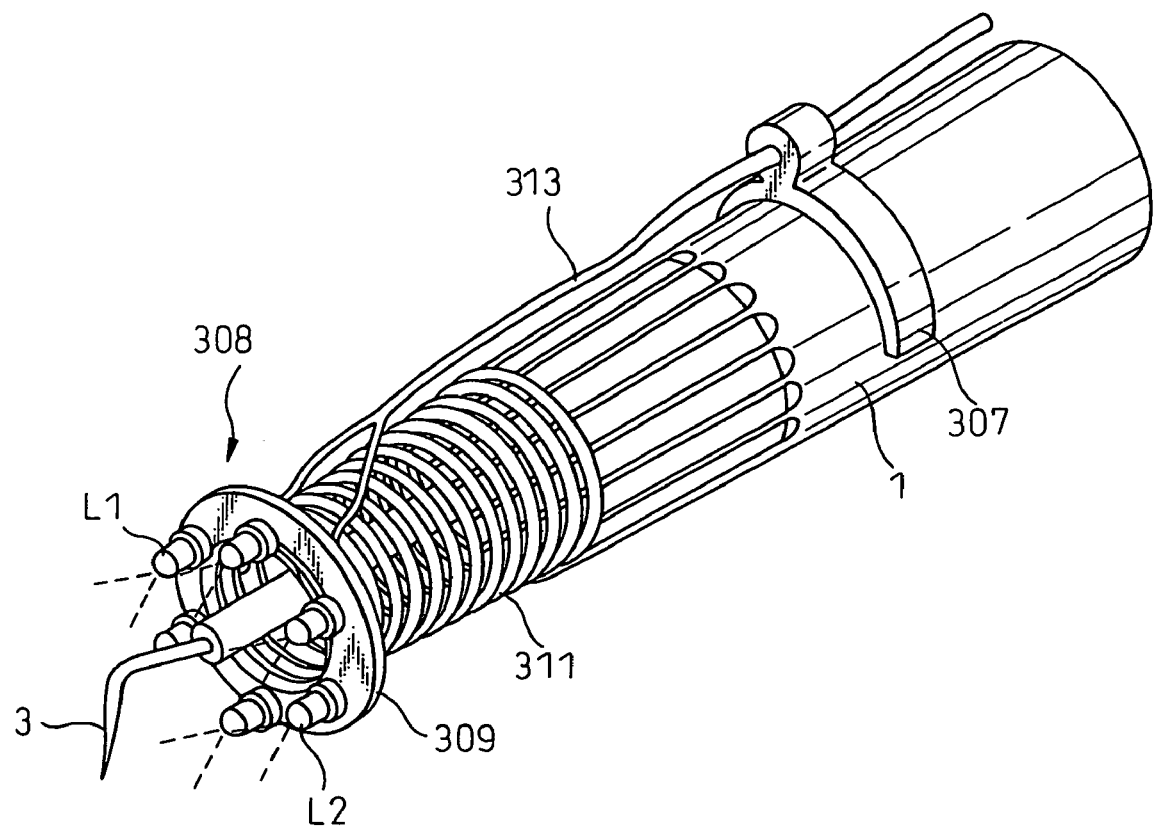
FIG. 47 is a diagram for explaining the condition in which the intraoral illumination device of the 34th specific example is mounted on a dental instrument.

FIG. 47 shows an example in which the power supply separated type intraoral illumination device of the 34th specific example shown in FIG. 46 is mounted on the scaler handpiece in a manner similar to that shown in FIG. 38 in which the power supply built-in type intraoral illumination device of the 27th specific example is mounted on the scaler handpiece. In the case of the power supply separated type, the presence of the power supply line 313 which extends from the adapter body 308 and is routed along the portion near the hand of the clinician may interfere with the treatment work; to avoid this, the power supply line 313 is supported by the mounting member 307 detachably mounted on the barrel of the handpiece body 1.

Embodiment 11

In the intraoral illumination devices according to the ninth and tenth embodiments so far described, the light radiating means containing the light-emitting device is mounted in the adapter body, and the light radiated from the light radiating means illuminates the area forward of the treatment tool in the axis direction thereof; in the 10th embodiment, the power supply is separated, and the power supply box is placed at a location remote from the adapter body. In the 11th embodiment hereinafter described, the light source of the light radiating means of the intraoral illumination device is also placed at a location remote from the adapter body, aiming to simplify the mounting structure for mounting the intraoral illumination device on the dental instrument.

Figure 48:
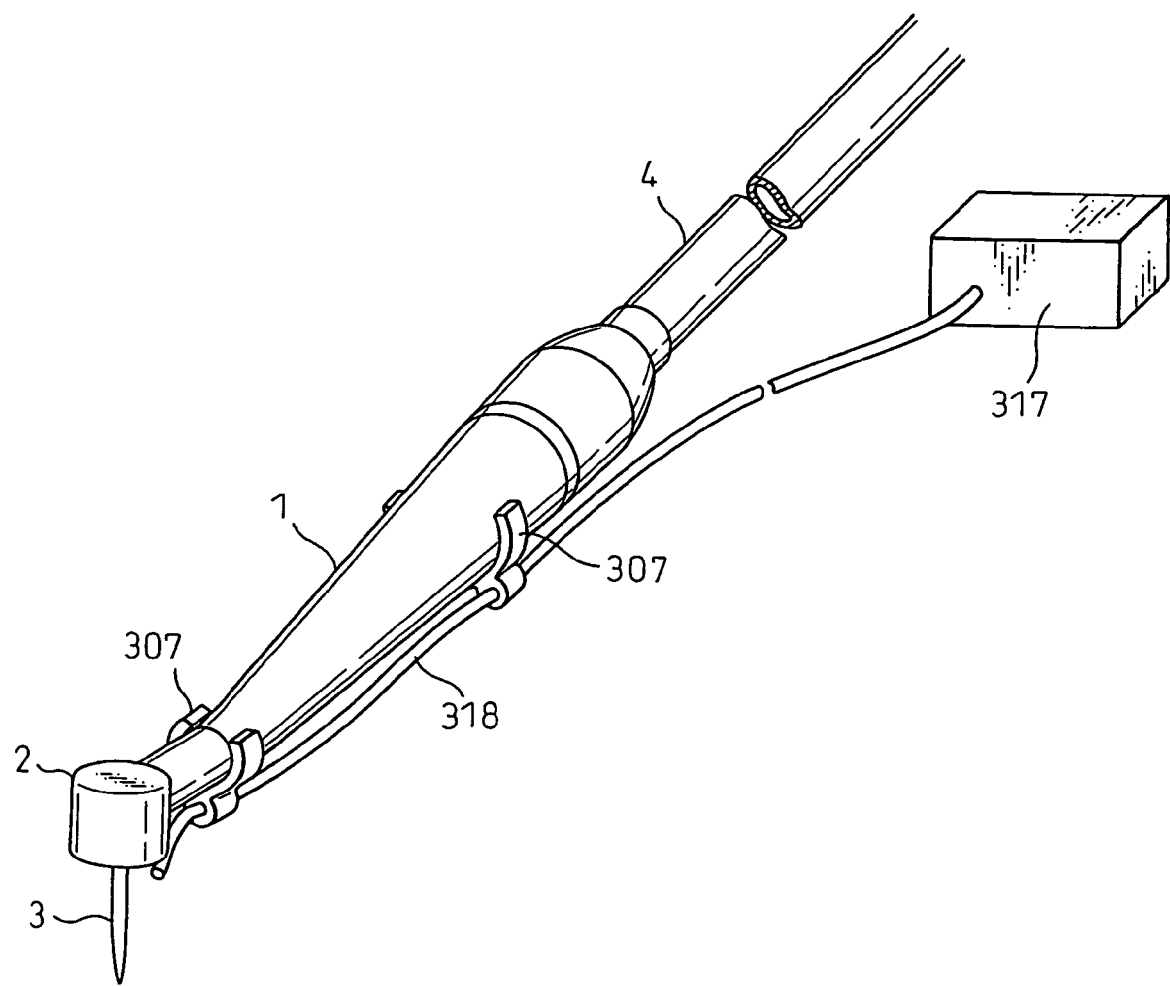
FIG. 48 is a diagram for explaining a 35th specific example in which a light guide type intraoral illumination device according to an 11th embodiment of the present invention is mounted on a handpiece body.

FIG. 48 shows a 35th specific example of the intraoral illumination device according to the 11th embodiment. FIG. 48 shows an example in which the intraoral illumination device is mounted on an air turbine handpiece which is one example of the dental instrument. The light source of the light radiating means of the intraoral illumination device is mounted within a light source box 317 placed at a location remote from the handpiece body 1. The light source box 317 only needs to be placed at a location that does not interfere with the treatment work.

An optical fiber 318 as a light guide member extends from the light source box 317 to the handpiece body 1, and this optical fiber 318 is detachably supported by mounting members 307 on the barrel of the handpiece 1 and at the base of the head 2, respectively.

The light source box 317 is provided with a switch for turning on and off the light source of the light radiating means; if the light source comprises a plurality of light-emitting devices for emitting lights of different wavelengths, a switch for controlling the selection of the light-emitting devices is also provided. Furthermore, a switch that can adjust the light output level of each light-emitting device may also be provided. The light emitted by being controlled using these switches is guided through the optical fiber 318 up to the handpiece body 1. A wavelength selecting switch and a light output level adjusting switch may also be provided on the light source box 317.

A light radiating part is formed at the forward end of the optical fiber 318; when the intraoral illumination device is mounted on the air turbine handpiece as shown in FIG. 48, the light radiating part is oriented so as to be able to illuminate the area forward of the treatment tool 3 in the axis direction thereof. When mounting it, for example, on a micromotor handpiece or a scaler handpiece, the light radiating part is held parallel to the center axis of the handpiece body 2 to illuminate the area forward of the treatment tool 3.

The light radiating function of the intraoral illumination device of the 35th specific example is the same as that of the 21st specific example shown in FIG. 42B, and therefore the description thereof will not be repeated here.

Figure 49:
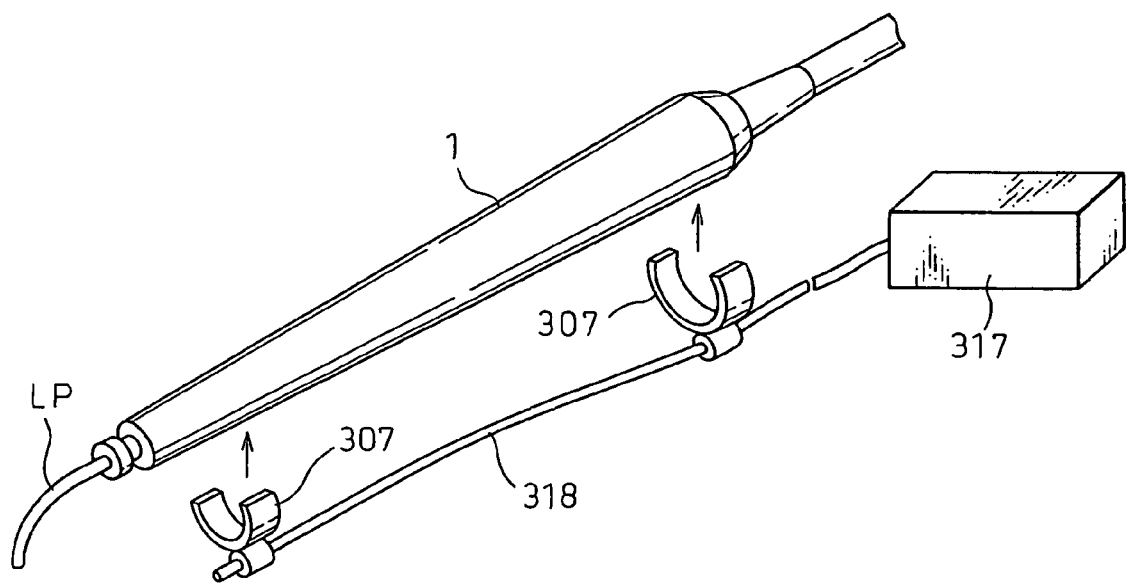
FIG. 49 is a diagram for explaining a 36th specific example in which the light guide type intraoral illumination device of the 35th specific example is mounted on a laser handpiece body.

FIG. 49 shows a 36th specific example in which the intraoral illumination device of the 35th specific example shown in FIG. 48 is mounted on a laser handpiece. The intraoral illumination device used in the 36th specific example is adjusted so that the forward end of the optical fiber 318, when mounted on the laser handpiece, points toward the tip of the laser probe LP.

Figure 50:
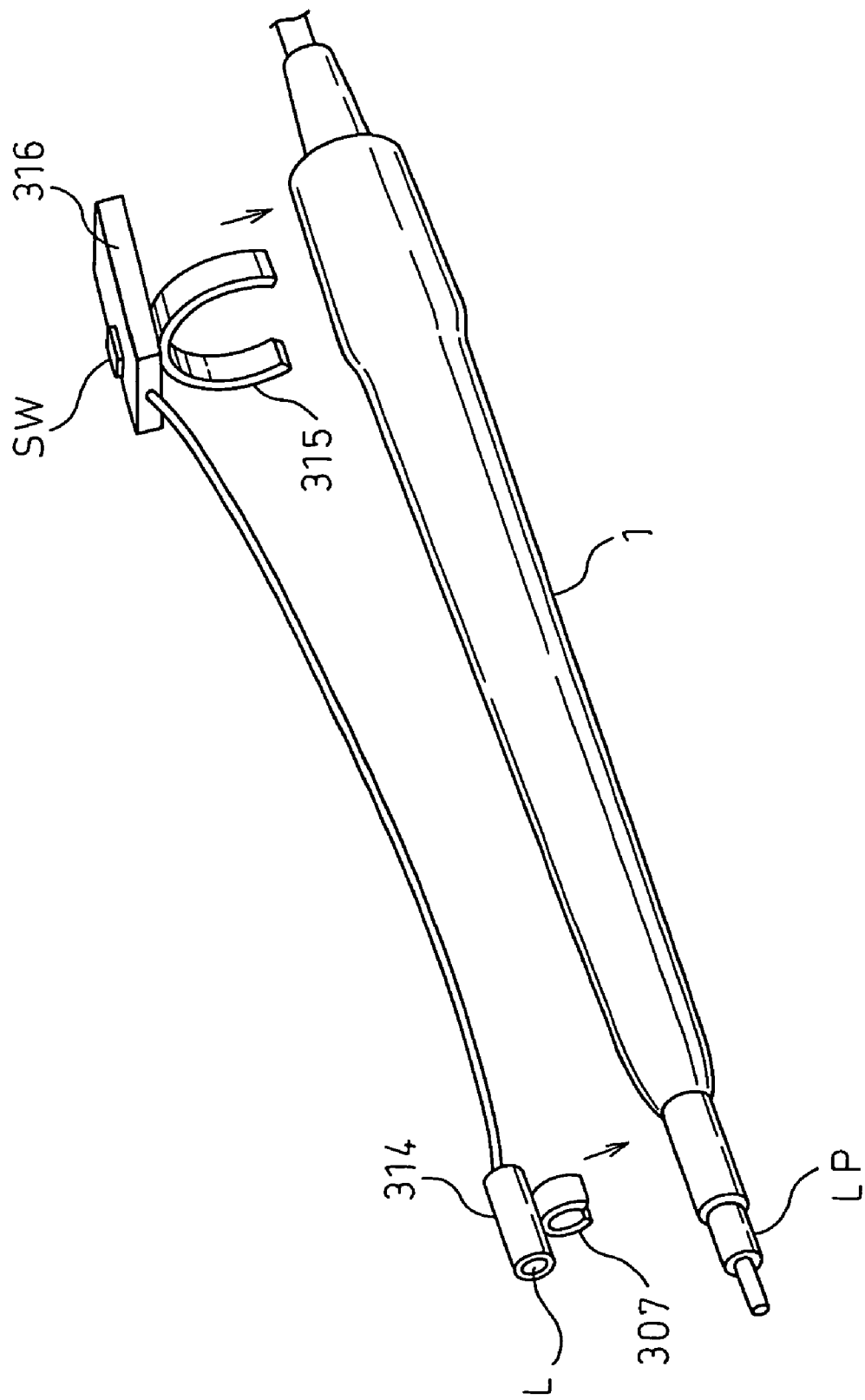
FIG. 50 is a diagram for explaining a 37th specific example in which the light guide type intraoral illumination device of the 35th specific example is modified and mounted on the laser handpiece body.

Next, FIG. 50 shows a 37th specific example in which an intraoral illumination device having a different structure from that of the 36th specific example is mounted on the laser handpiece. The structure of the intraoral illumination device according to the 37th specific example is basically the same as that of the intraoral illumination device according to the 31st specific example shown in FIG. 42A, but while in the 31st specific example, the light-emitting device L mounted on the light source mounting member 314 is oriented so as to illuminate the area forward of the tip of the treatment tool 3, the light source mounting member 314 in the 37th specific example is mounted on the laser handpiece body 1 so that the light-emitting device L projects light in a direction parallel to the axis of the laser probe LP. Since the projection direction of the excitation light from the light-emitting device L is parallel to the axis of the handpiece body 1, the light source mounting member 314 can be mounted on any position around the axis of the handpiece body 1.

Embodiment 12

The intraoral illumination devices according to the ninth to eleventh embodiments so far described are equipped with light radiating means for radiating excitation light that can detect intraoral lesions, but when a clinician actually performs treatment by attaching the light radiating means to a dental instrument, the clinician has to wear eyeglasses or goggles equipped with a filtering function that allows reflected fluorescent light occurring due to the radiation of the excitation light to pass through or that rejects only the excitation light.

However, when diagnosing lesions by observing the light passed through the eyeglasses or goggles worn over the eyes while radiating lights of different wavelengths by switching from one to another, the clinician has to select from among a plurality of pairs of eyeglasses or goggles the one having filtering characteristics that match the wavelength of the light being radiated, which is not only costly but troublesome, because the eyeglasses or goggles have to be changed each time the wavelength is switched from one to another.

In view of this, in the intraoral illumination device according to the 12th embodiment, the filtering function that can detect lesions is not accomplished by such means as the eyeglasses or goggles, but a flat filter plate having such a filtering function is placed near the dental instrument and the clinician observes the lesion through this filter plate.

Figure 51:
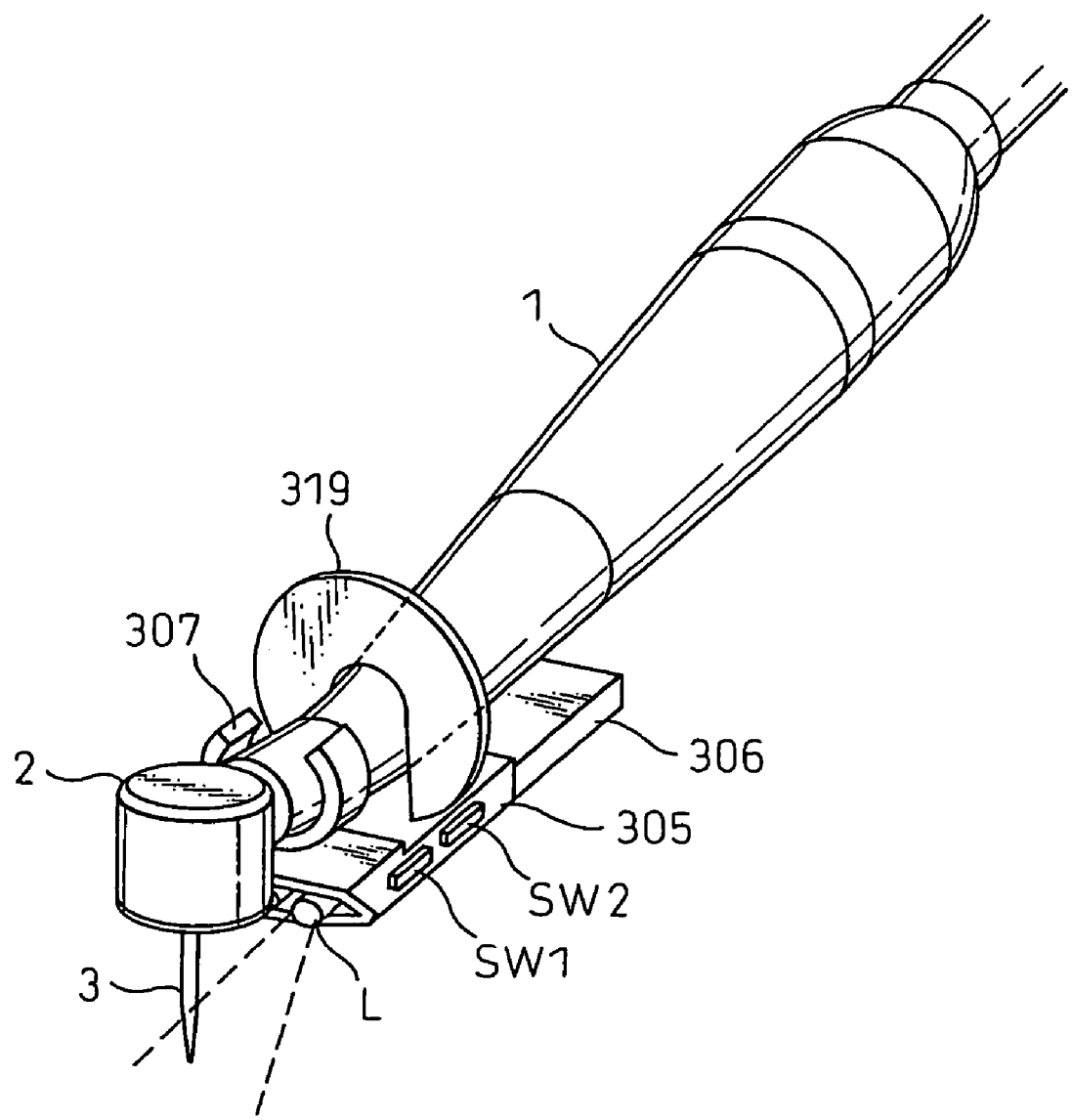
FIG. 51 is a diagram for explaining a 38th specific example in which the intraoral illumination device of the present invention equipped with an eye protector member according to a 12th embodiment is implemented as a power supply built-in type.
Figure 52:
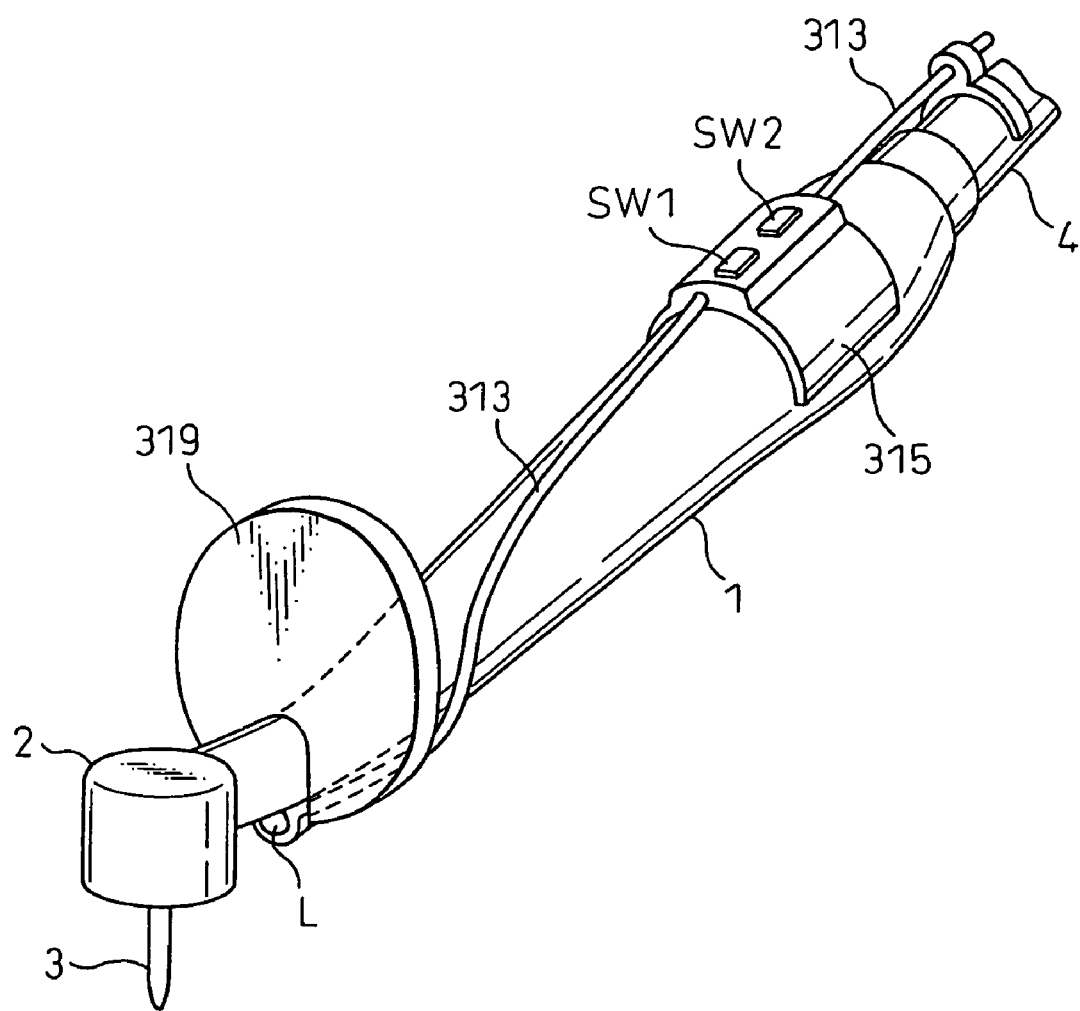
FIG. 52 is a diagram for explaining a 39th specific example in which the 12th embodiment is implemented as a power supply separated type.
Figure 53:
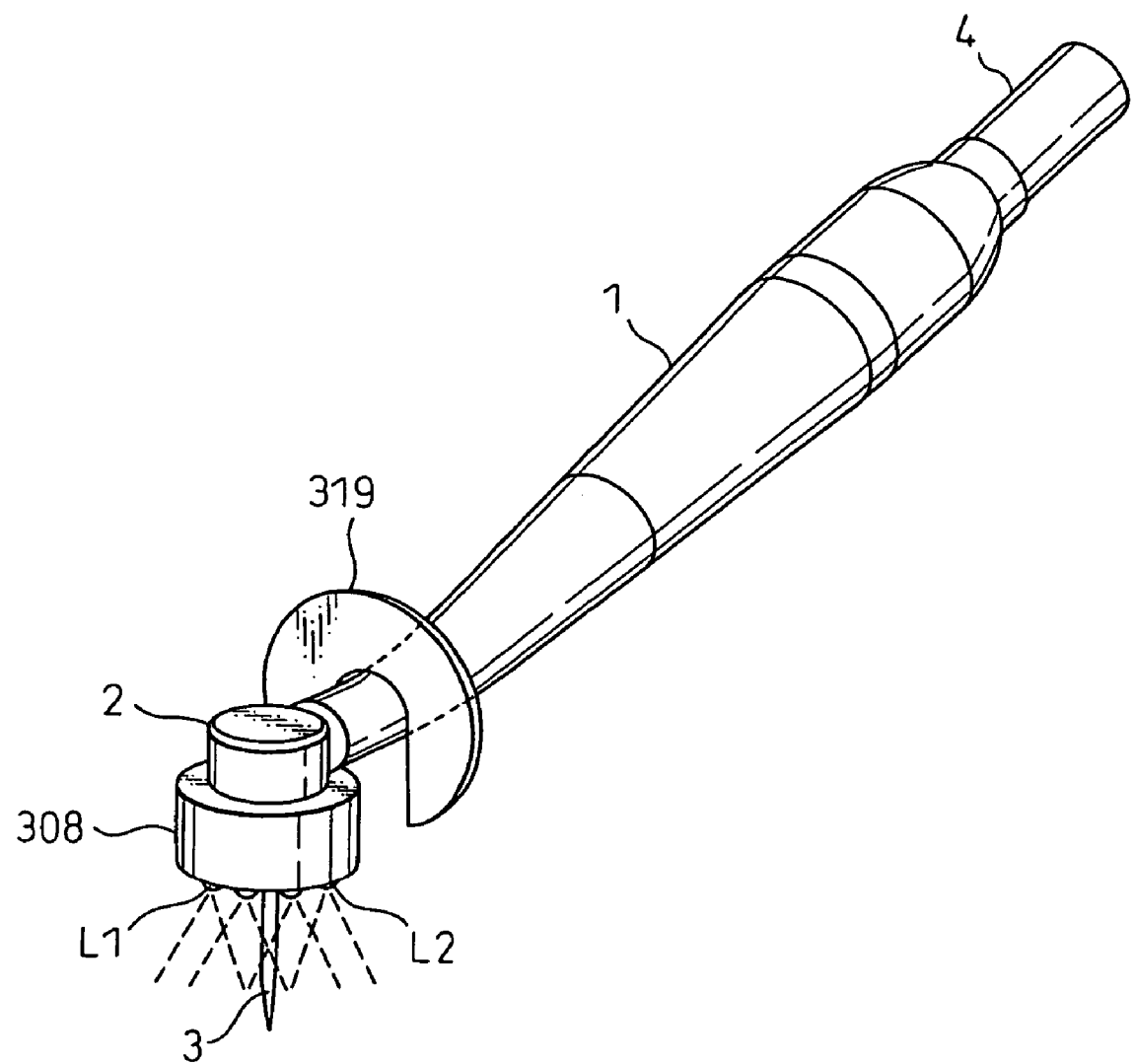
FIG. 53 is a diagram for explaining a 40th specific example in which the 12th embodiment is implemented as a power supply separated type provided with a switch operating part.

FIG. 51 shows a 38th specific example of the intraoral illumination device according to the 12th embodiment, in which the intraoral illumination device of the 25th specific example shown in FIGS. 33A and 33B is combined with such a filter plate 319. Likewise, FIG. 52 shows a 39th specific example of the intraoral illumination device according to the 12th embodiment, in which the intraoral illumination device of the 31st specific example shown in FIGS. 42A and 42B is combined with the filter plate 319, and FIG. 53 shows a 40th specific example of the intraoral illumination device according to the 12th embodiment, in which the intraoral illumination device of the 32nd specific example shown in FIGS. 43A and 43B is combined with the filter plate 319.

In each of the intraoral illumination devices of the 38th to 40th specific examples, the filter plate 319 is detachable, and is mounted so that its plane is perpendicular to the center axis of the handpiece body 1. The size of the filter plate 319 is chosen so as not to interfere with the intraoral treatment work performed using the dental instrument.

With the filter plate 319 thus mounted, the clinician can treat the intraoral lesion while observing the lesion. When the wavelength of the light to be radiated is changed, the clinician only needs to change the filter plate 19, which is simpler than changing the eyeglasses or the like. Employing such filter plates also offers the advantage of reducing the cost.

The specific examples according to the first to 12th embodiments have been described above by focusing on the structure of the light radiating means to be provided in the dental diagnostic and treatment apparatus. Next, the method of driving the light-emitting devices contained in the light radiating means will be described by referring to a circuit configuration that can be applied in common to the specific examples described above.

FIG. 54 is a diagram showing a driving circuit for controlling the on/off operation of a plurality of light-emitting devices. In the case of the 25th specific example shown in FIG. 33A, for example, this driving circuit can correspond to the switch SW1. The driving circuit includes a radiating means comprising a plurality of light-emitting devices L1 to L4 each for emitting light of a different wavelength; more specifically, the radiating means comprises an illumination light emitting part comprising the light-emitting device L1 constructed from an LED for emitting infrared light LE1 and the light-emitting device L2 constructed from an LED for emitting white light LE2, and an excitation light emitting part comprising the light-emitting devices L3 and L4 constructed from LEDs for emitting ultraviolet lights LE3 and LE4 of different wavelengths.

The driving circuit further comprises: a switch circuit SW connected between a power supply 60 and the light-emitting devices L1 and L4 and capable of controlling the on/off operation of each individual light-emitting device; a light emission selection instruction device 62 for selecting from among the plurality of light-emitting devices L1 and L4 one or more light-emitting devices to be turned on; and a control circuit 61 for controlling the operation of the switch SW in accordance with the instruction of the light emission selection instruction device 62.

For example, the light-emitting device L1 for emitting the infrared light can be turned on by turning on the first light source selection switch under the instruction of the light emission selection instruction device 62. Likewise, the light-emitting device L2 for emitting the white light can be turned on by operating the second light source selection switch, the light-emitting device L3 for emitting the first ultraviolet light can be turned on by operating the third light source selection switch, and the light-emitting device L4 for emitting the second ultraviolet light can be turned on by operating the fourth light source selection switch. In this way, the desired kind of light can be selected for radiation.

Furthermore, the white illumination light and the first or second ultraviolet light can be simultaneously radiated by simultaneously turning on the second light source selection switch for the light-emitting device L2 for emitting the white light and the third light source selection switch for the light-emitting device L3 for emitting the first ultraviolet light or the fourth light source selection switch for the light-emitting device L4 for emitting the second ultraviolet light. By radiating different kinds of lights simultaneously, the fluorescence image of the lesion, occurring due to the radiation of the excitation light, and the reflected image of the normal tissue around the lesion, occurring due to the radiation of the illumination light, can be made clearly visible, making it possible to accurately recognize the position and extent of the lesion.

Here, as shown in FIG. 55, time-division control can be performed, for example, between the switch SW1 for controlling the on/off operation of the light-emitting device L1 and the switch SW2 for controlling the on/off operation of the light-emitting device L2 in the switch circuit SW, thereby controlling the operation of the light-emitting devices L1 and L2 in a time-division fashion. The time-division control may be performed by dividing the time into small fractions, allocating, for example, a 1/60-second time slot for the radiation of the illumination light and a 1/60-second time slot for the radiation of the excitation light, or by allocating relatively long time slots, for example, two seconds for the radiation of the illumination light and 1/2 second for the radiation of the excitation light; the length of the radiation time in the time-division control can be changed according to the fluorescence emission condition of the lesion. Further, a sequence in which the illumination light and the excitation light are radiated in short pulses in a time-division fashion may be predetermined, and a special switch for that purpose may be provided in the light emission selection instruction device 62. Here, if each light is radiated for the desired length of time by operating the special switch, the same effect as that of the simultaneous radiation can be obtained when the observer directly views the radiation target area, because of the retinal persistence of the observer's eye. Further, this may be combined with the reflected light image obtained by the radiation of the infrared light, to produce diagnostic image information.

In the above-described embodiments, in particular, when the power supply box for controlling the operation of the light-emitting devices is separated from the adapter box, or when the light source box is located remotely from the adapter body, the on/off control of the radiating means may be performed using a foot pedal switch.

Figure 56:
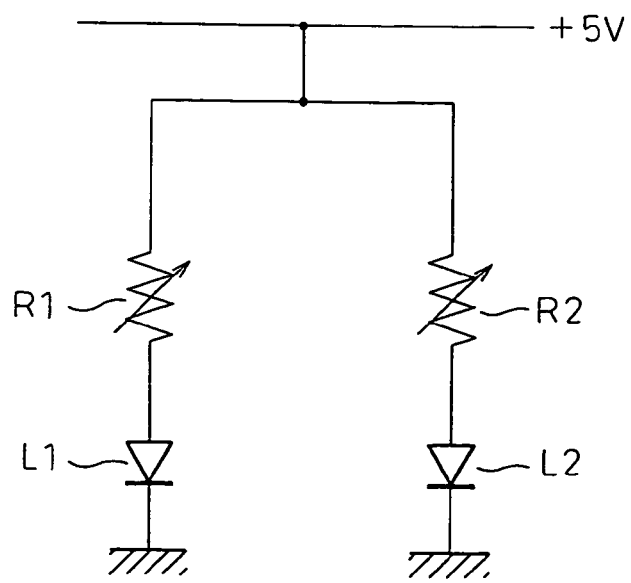
FIG. 56 is a diagram showing an example of an electrical circuit which can control the light output balance between excitation light and illumination light.

FIG. 56 shows an electrical circuit which is applicable to each of the above-described specific examples, and in which when simultaneously radiating the excitation light and the white light, the balance between the light output level of the excitation light and the light output level of the white light is controlled by adjusting variable resistors provided as light level adjusting means. R1 is a variable resistor for adjusting the light output level of the illumination light emitting device L1 comprising the LED for emitting the white light. R2 is a variable resistor for adjusting the light output level of the excitation light emitting device L2 comprising the LED for emitting the excitation light. Using these variable resistors, currents flowing in the respective LEDs are adjusted to adjust the light output levels of the respective light-emitting devices. Here, if the variable resistors R1 and R2 for adjusting the light output levels of the light-emitting devices L1 and L2 are operated, for example, in such a manner that the light output level of one or the other of the LEDs is set to zero, it becomes possible to select not only the above-described simultaneous radiation mode, but also the illumination light radiation mode, i.e., the white light only radiation mode, or the excitation light radiation mode, thus implementing a mode selecting means for selecting the radiation mode from among the simultaneous radiation mode, the illumination light radiation mode, and the excitation light radiation mode.

Furthermore, the light output level adjusting variable resistors R1 and R2 for the respective LEDs may be adjusted at the factory so as to provide a fixed radiation mode of optimum setting. It is desirable that the white light as the illumination light be set to a light output level lower than the light output level of the excitation light; with this setting, it becomes possible to prevent fluorescence from being buried in the illumination light, and the lesion and the tissue around the lesion can be observed simultaneously. It is desirable to make such light output level setting as the initial setting at the time of shipment from the factory.

When it is desired to observe mainly the tissue around the lesion while displaying the lesion just for reference, an adjustment should be made to increase the light output level of the white illumination light, though it may depend on the clinician's preference. Of course, an adjustment may also be made to increase the light output level of the white illumination light when it is desired to simply obtain a bright image. The above-described embodiments have shown examples in which white light is used as the illumination light, but instead, reddish light or yellowish light may be used as needed. In that case also, the degree of enhancement of the lesion due to the radiation of the excitation light can be adjusted by adjusting the light output level of the illumination light in addition to the light output level of the excitation light. The proportion of the red component or yellow component can also be adjusted by adjusting the illumination light.

Figure 57:
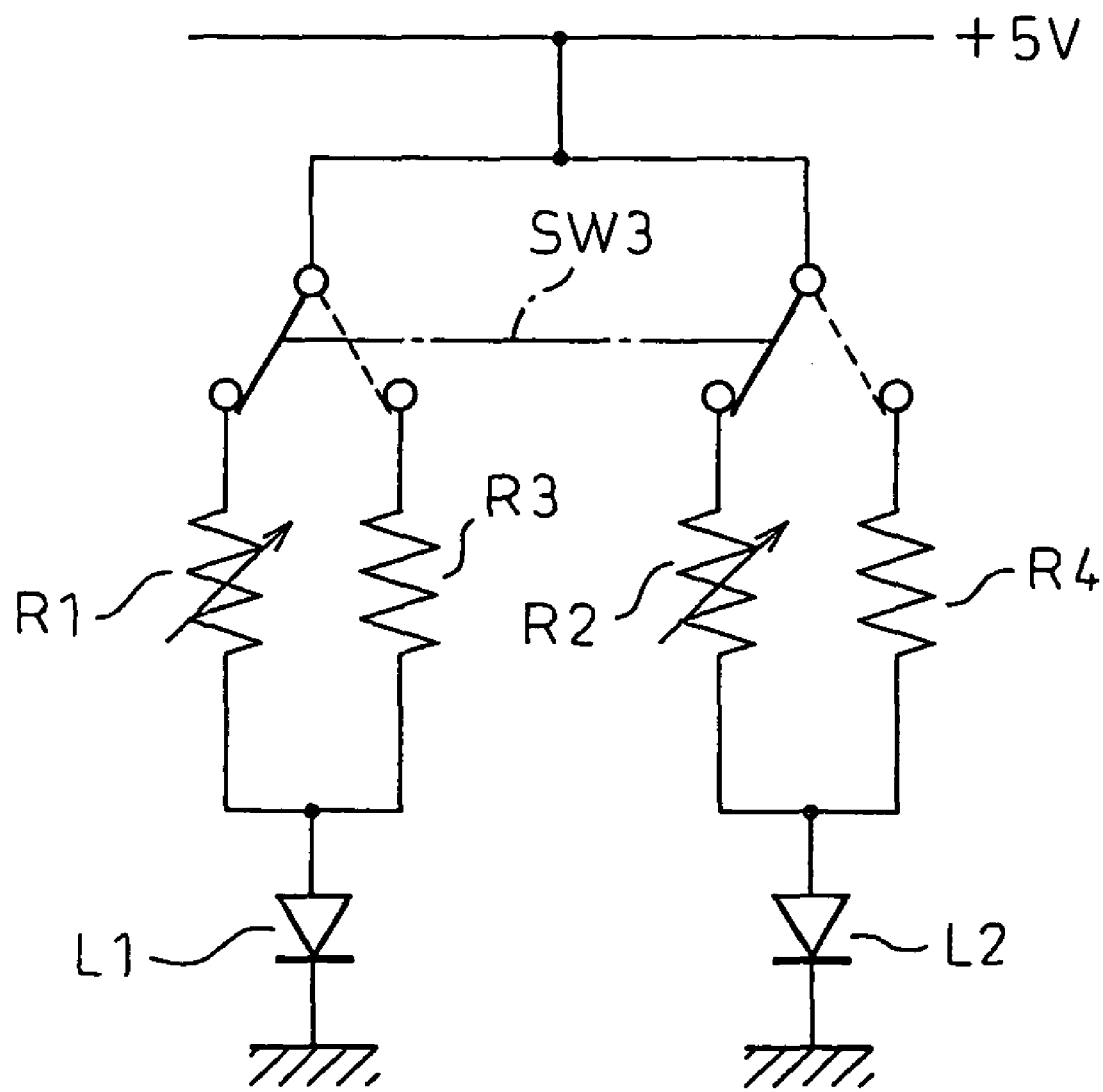
FIG. 57 is a diagram showing an electrical circuit which can switch the setting for the excitation light versus illumination light output balance between factory initial setting and user adjusted setting.

FIG. 57 shows a circuit diagram in which provisions are made so that, while the optimum initial setting is carried out at the time of shipment from the factory, the light output level of the illumination light emitting device L1 comprising the LED for emitting the white light and the light output level of the excitation light emitting device L2 comprising the LED for emitting the excitation light can be adjusted to desired levels by operating the light output level adjusting variable resistors at the user side. Selector switch SW3 are switchable between the factory initial setting position and the user setting position, as shown by solid and dashed lines in the figure.

When the selector switches SW3 are set to the user setting positions as shown by the solid lines, the white LED adjusting variable resistor R1 and the excitation light adjusting variable resistor R2 can be adjusted as desired independently of each other. For the factory-set optimum initial setting, the selector switches SW3 are operated to switch in the white LED adjusting fixed resistor R3 and the excitation light adjusting fixed resistor R4, and the setting can thus be switched to achieve the optimum balance between the excitation light and the white light. By thus operating the selector switches SW3, the user can switch the setting as desired between the factory initial setting and the user adjusted setting. These light output level adjusting means can be applied to any of the above-described embodiments.

Figure 58:
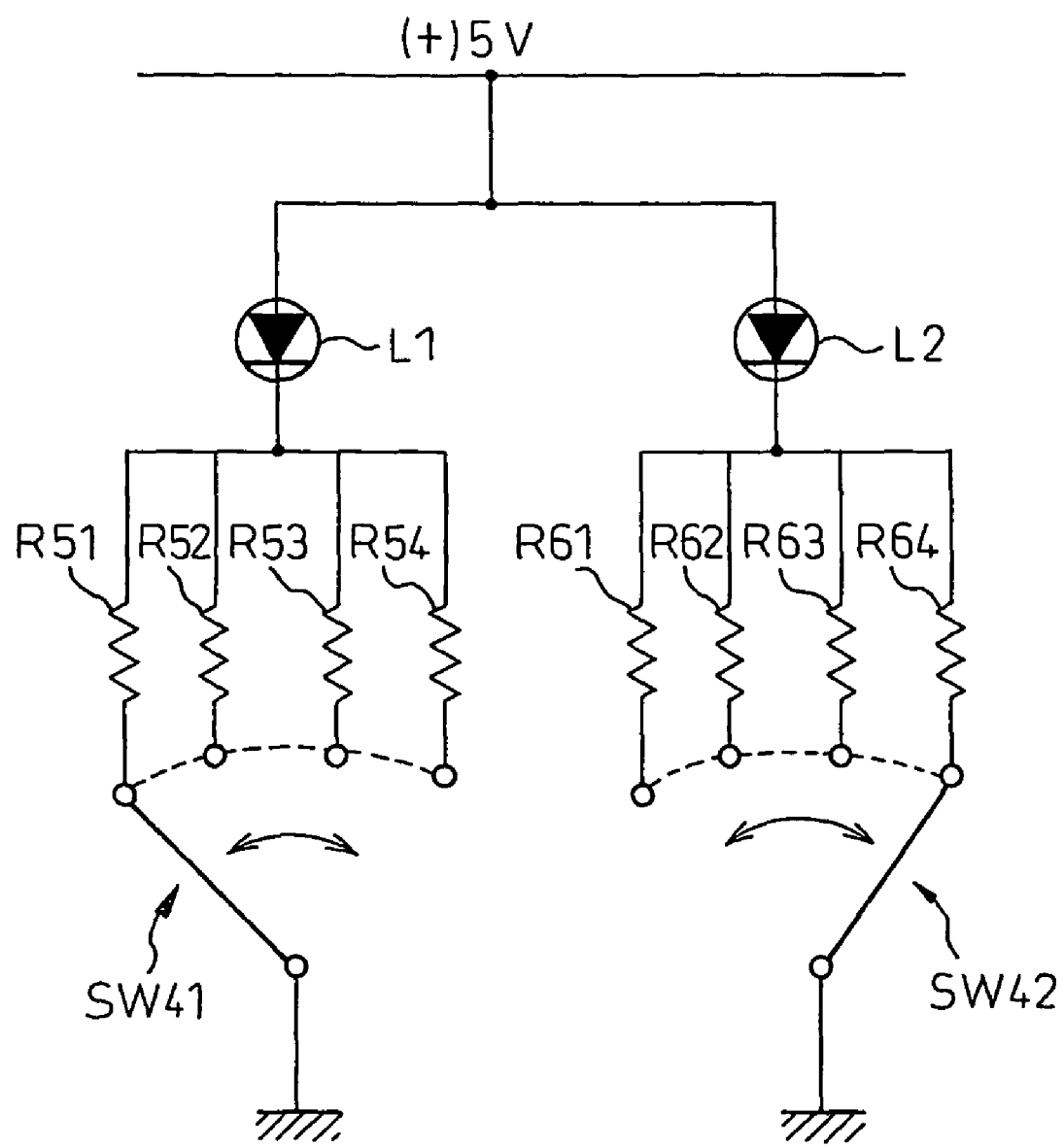
FIG. 58 is a diagram showing another example of the electrical circuit that can control the light output balance between the excitation light and the illumination light.

FIG. 58 shows another circuit configuration example of the light output level adjusting means. In this example, as the light output level adjusting means for the illumination light, fixed resistors R51 and R54 having different resistance values are connected in parallel between the light-emitting device L1 and ground via a rotary switch SW41 to adjust the light output level of the light-emitting device L1 such as a white LED that emits the illumination light. By operating the rotary switch SW41 to select a desired one of the resistors for connection to the light-emitting device L1, a current having the desired electric current is supplied to the light-emitting device L1. A similar circuit configuration is used for the light-emitting device L2 that emits the excitation light; that is, fixed resistors R61 and R64 having different resistance values for adjusting the light output level of the excitation light are selectively connected by a rotary switch SW42 to supply a current having the desired value to the light-emitting device L2.

For example, the fixed resistors R51 and R54 for adjusting the illumination light output level are chosen to have resistance values corresponding to the light output levels of 2%, 35%, 75%, and 100%, respectively, and likewise, the fixed resistors R61 and R64 for adjusting the excitation light output level are chosen to have resistance values corresponding to the light output levels of 2%, 35%, 75%, and 100%, respectively. With these resistance value settings, by suitably operating the rotary switches SW1 and SW42 according to the purpose, the output balance between the illumination light and the excitation light can be adjusted while radiating the illumination light and the excitation light simultaneously.

For example, when it is desired to observe, among others, the condition of the lesion such as caries, the output level of the excitation light is increased by selecting the fixed resistor R64 whose resistance value corresponds to the excitation light output level of 100%, while for the illumination light, the fixed resistor R51 whose resistance value corresponds to the light output level of 2% is selected. With this setting, it becomes possible to clearly observe the extent of the lesion emitting the fluorescence, though the normal tissue around the lesion appears dark.

On the other hand, when it is desired to focus attention on the normal tissue around the lesion, the fixed resistor R64 corresponding to the excitation light output level of 100% is selected by the rotary switch SW2, and the fixed resistor R52 corresponding to the illumination light output level of 35% is selected by the rotary switch SW41. With this setting, it becomes possible to observe the condition of the normal tissue while identifying the location of the lesion emitting the fluorescence. It also becomes possible to observe the lesion and the normal tissue around it with natural color tones. The above light output settings of 2%, 35%, 75%, and 100% are only examples, and other suitable light output settings can also be used.

In this way, the lesion and the normal tissue around it can be clearly observed simultaneously, without the fluorescence being buried in the illumination light. In the above example, the light output level adjusting means for adjusting the balance between the output level of the illumination light and the output level of the excitation light in the radiating means has been constructed using the rotary switches and fixed resistors; however, it will be recognized that the configuration is not limited to the illustrated one, and that various known circuits can be employed.

The embodiment shown in FIGS. 56 to 58 has been described by assuming that L1 is the light-emitting device for radiating the illumination light and L2 is the light-emitting device for radiating the excitation light; here, the variable resistors shown in FIG. 56, the variable resistors and fixed resistors shown in FIG. 57, or the rotary switches and fixed resistors shown in FIG. 58 may be connected to the respective light-emitting devices L1 to L4 in FIG. 54 so that the light output levels of L1 to L4 can be controlled independently of each other.

In that case, the light output level adjustment becomes possible between the LED that emits the white light and the LED that emits the excitation light, between the plurality of LEDs that emit the excitation lights of different wavelengths, and also between the LED that emits the white light and any one of the plurality of LEDs that emit the excitation lights of different wavelengths.

Further, various combinations of illumination light output levels and excitation light output levels may be set in advance in accordance with clinical cases and purposes of use, with provisions made to be able to select a suitable combination by operating a selector switch according to the clinical case or the purpose of use.

The light radiating means provided in the dental diagnostic and treatment apparatus can radiate illumination light and excitation light in various patterns, specific examples of which will be given below. In the following examples, it is assumed that white light is used as the illumination light.

a) When the white light source and one kind of excitation light source are provided, either the white light or the excitation light is radiated by selecting only the white light source or only the excitation light source.

b) When the white light source and one kind of excitation light source are provided, the white light and the excitation light are radiated by adjusting the light output level of only the white light source or only the excitation light source. In this case, only one of them may be selected and its light output level may be adjusted, or both may be radiated simultaneously by adjusting the output level of either one of them.

c) When the white light source and one kind of excitation light source are provided, the white light source and the excitation light source are simultaneously turned on, and the white light and the excitation light are radiated by adjusting the output levels of both of them. In this case, the output levels may be adjusted individually or in a proportional manner.

d) When more than one kind of excitation light source is provided, excitation light is radiated by selecting one of the excitation light sources.

e) When more than one kind of excitation light source is provided, a plurality of excitation lights are radiated by adjusting the light output level of only one of the excitation light sources. In this case, only one of them may be selected and its light output level may be adjusted, or both may be simultaneously radiated by adjusting the output level of either one of them.

f) When more than one kind of excitation light source is provided, a plurality of excitation lights are radiated by simultaneously turning on a plurality of excitation light sources, and the light output level of each light source is adjusted. In this case, the output levels may be adjusted individually or in a proportional manner.

g) When the white light source and more than one kind of excitation light source are provided, the radiation patterns a) to f) can be suitably combined.

What is claimed is:

1. A dental treatment apparatus comprising:
   an instrument having a forward end equipped with treatment tool for treating a lesion in an oral cavity; and
   a light radiating unit having a first light source for emitting an excitation light and a second light source for emitting a white light into said oral cavity, said first and second light sources being disposed at or near said forward end, wherein
   a wavelength of said excitation light is selected from within a near ultraviolet region of 405±50 nm, a red region of 700±100 nm, an infrared region, or a near infrared region, and wherein
   said light radiating unit is configured to radiate said excitation light or said white light by switching lighting between said first light source and said second light source, or configured to variably adjust a light emission level of at least one of said first light source and said second light source.

2. A dental treatment apparatus as claimed in claim 1, wherein said light radiating unit is configured to simultaneously radiate said excitation light and said white light.

3. A dental treatment apparatus as claimed in claim 1, wherein said light radiating unit is configured to selectively radiate said excitation light and said white light.

4. A dental treatment apparatus as claimed in claim 1, wherein each of said first light source for emitting excitation light and said second light source for emitting said white light include a light-emitting device constructed from a light-emitting diode or a semiconductor laser diode.

5. A dental treatment apparatus as claimed in claim 1, wherein said second light source for emitting said white light includes a light-emitting device for emitting a white light.

6. A dental treatment apparatus as claimed in claim 5, wherein said light radiating unit is configured to simultaneously radiate said excitation light and said white light.

7. A dental treatment apparatus as claimed in claim 4, wherein said light radiating unit is configured to variably adjust light emission levels of both said light sources.

8. A dental treatment apparatus as claimed in claim 4, wherein said light radiating unit includes a plurality of light sources for emitting said excitation light at different wavelengths, and is configured to radiate light at one wavelength by switching between said plurality of light sources.

9. A dental treatment apparatus as claimed in claim 8, wherein said light radiating unit includes a plurality of light sources for emitting said excitation light at different wavelengths, and is configured to radiate said excitation light at one wavelength by switching lighting between said plurality of light sources.

10. A dental treatment apparatus as claimed in claim 8, wherein said light radiating unit includes a plurality of excitation light sources for emitting said excitation light at different wavelengths and a white light source for emitting white light, and is configured to radiate said excitation light and said white light by switching lighting between said plurality of excitation light sources and said white light source, or is configured to variably adjust a light emission level of at least one light source selected from among said plurality of excitation light sources and said white light source.

11. A dental treatment apparatus as claimed in claim 1, wherein said second light source of said light radiating unit includes a type of lamp selected from a group consisting of a halogen lamp, a xenon lamp, a sodium lamp, a metal halide lamp, a mercury lamp, and a blacklight lamp.

12. A dental treatment apparatus as claimed in claim 11, wherein said light radiating unit includes an optical filter for selecting light of a designated wavelength from the light emitted from said first light source.

13. A dental treatment apparatus as claimed in claim 12, wherein the light of said designated wavelength is selected by said filter with a second filter having a different characteristic.

14. A dental treatment apparatus as claimed in claim 11, wherein said light radiating unit is configured to variably adjust a light emission level of said second light source.

15. A dental treatment apparatus as claimed in claim 1, wherein said light radiating unit includes a plurality of light sources for emitting said excitation light at different wavelengths, and is configured to select the excitation light to be emitted by sequentially switching between said plurality of light sources to sequentially radiate said excitation light at said different wavelengths in a time-division fashion.

16. A dental treatment apparatus as claimed in claim 1, wherein said light radiating unit includes a radiating part from which said excitation light and said white light are radiated toward said lesion, and wherein said radiating part is disposed in said treatment tool or near a mounting portion of said treatment tool.

17. A dental treatment apparatus as claimed in claim 16, wherein said excitation light and said white light are radiated from an area surrounding said treatment tool toward said lesion.

18. A dental treatment apparatus as claimed in claim 1, wherein said first and second light sources are mounted on a detachable member formed to be detachable from said forward end, and said detachable member includes a connecting member which is configured to detachably engage with said forward end and which, when placed into engagement with said forward end, to supply power to said light sources.

19. A dental treatment apparatus as claimed in claim 1, wherein said treatment tool is attached to said forward end, and said first and second light sources are disposed on said forward end.

20. A dental treatment apparatus as claimed in claim 19, wherein said light radiating unit radiates said excitation light and said white light onto said lesion in a time-division fashion.

21. A dental treatment apparatus as claimed in claim 1, wherein a radiating part, from which said excitation light or said white light are radiated toward said lesion, or each of said first and second light sources is provided in an adapter having a mounting member capable of being detachably mounted on the forward end of said instrument.

22. A dental treatment apparatus as claimed in claim 21, wherein said first light source for emitting said excitation light and said second light source for emitting said white light into said oral cavity each include a plurality of light-emitting devices, and wherein said plurality of light-emitting devices are arranged side by side in an end face portion of said adapter.

23. A dental treatment apparatus as claimed in claim 21, wherein said adapter has a ring-shaped structure which is detachably fitted onto the forward end of said instrument.

24. A dental treatment apparatus as claimed in claim 21, wherein said adapter includes an operating part for operating light illuminations of said first and second light sources.

25. A dental treatment apparatus as claimed in claim 24, wherein said adapter-includes a power supply for driving said light sources for lighting.

26. A dental treatment apparatus as claimed in claim 25, wherein said power supply is a primary cell or a secondary cell.

27. A dental treatment apparatus as claimed in claim 21, wherein a power supply for driving said first and second light sources is provided separately from said adapter.

28. A dental treatment apparatus as claimed in claim 27, wherein said power supply is detachably mounted on a body of said instrument.

29. A dental treatment apparatus as claimed in claim 21, wherein an operating part for operating lighting of said first and second light sources is detachably mounted on a body of said instrument.

30. A dental treatment apparatus as claimed in claim 21, wherein said mounting member is configured to elastically hold said adapter on the forward end of said instrument.

31. A dental treatment apparatus as claimed in claim 21, wherein said adapter includes a filter plate having a plane surface perpendicular to an axis direction of a body of said instrument, and said plane surface spreading to encircle said body.

32. A dental treatment apparatus as claimed in claim 21, wherein when said instrument includes an illuminating unit for illuminating said oral cavity, said adapter is mounted at a position that interrupts an illumination light emitted from said illuminating unit.

33. A dental treatment apparatus as claimed in claim 1, wherein said instrument is a laser handpiece configured to radiate a treatment laser light into said oral cavity together with a guide light-to locate an area being illuminated by said treatment laser light, and wherein said excitation light is contained in said guide light.

34. A dental treatment apparatus as claimed in claim 4, wherein said light source includes said light-emitting device mounted near a mounting portion of said treatment tool.

35. A dental treatment apparatus as claimed in claim 34, wherein said light-emitting device is mounted in such a manner as to encircle said treatment tool.

36. A dental treatment apparatus as claimed in claim 34, wherein said light-emitting device is accommodated in a position near the mounting portion of said treatment tool.

37. A dental treatment apparatus as claimed in claim 1, wherein said light radiating unit includes a plurality of light sources each for emitting excitation light of a different wavelength, and an operating part configured to switch lighting between said plurality of light sources or configured to variably adjust a light emission level of at least one of said light sources is mounted on said instrument.

* * * * *